US007611867B2

(12) United States Patent
Proudfoot et al.

(10) Patent No.: US 7,611,867 B2
(45) Date of Patent: Nov. 3, 2009

(54) CC-CHEMOKINE BINDING TICK PROTEINS

(75) Inventors: Amanda Proudfoot, Chens sur Leman (FR); Christine Power, Thoiry (FR); Maud Deruaz, Carouge (CH)

(73) Assignee: Merck Serono SA, Coinsins, Vaud (CH)

( * ) Notice: Subject to any disclaimer, the term of this patent is extended or adjusted under 35 U.S.C. 154(b) by 0 days.

(21) Appl. No.: 12/096,107

(22) PCT Filed: Feb. 16, 2007

(86) PCT No.: PCT/EP2007/001361

§ 371 (c)(1),
(2), (4) Date: Jun. 4, 2008

(87) PCT Pub. No.: WO2007/093432

PCT Pub. Date: Aug. 23, 2007

(65) Prior Publication Data

US 2008/0287363 A1    Nov. 20, 2008

Related U.S. Application Data

(60) Provisional application No. 60/774,090, filed on Feb. 16, 2006.

(30) Foreign Application Priority Data

Feb. 16, 2006    (EP)    ................................ 06110029

(51) Int. Cl.
*C12N 15/62* (2006.01)
*C12N 15/63* (2006.01)
*A61K 38/00* (2006.01)
*C07K 14/00* (2006.01)
*C07H 21/04* (2006.01)

(52) U.S. Cl. .................. 435/69.1; 435/71.1; 435/252.3; 435/320.1; 435/69.5; 514/2; 514/12; 530/350; 536/23.4; 536/23.5

(58) Field of Classification Search ........................ None
See application file for complete search history.

(56) References Cited

U.S. PATENT DOCUMENTS

2003/0050244 A1    3/2003    Fuchsberger et al.
2007/0224125 A1    9/2007    Power et al.

FOREIGN PATENT DOCUMENTS

WO    WO 2005/063812    7/2005

OTHER PUBLICATIONS

Aljamali, M. N. et al. "RNA interference in ticks: a study using histamine binding protein dsRNA in the female tick *Amblyomma americanum*", *Insect Molecular Biology*, 2003, pp. 299-305, vol. 12, No. 3.
Baggiolini, M. "Chemokines in Pathology and Medicine", *Journal of Internal Medicine*, 2001, pp. 91-104, vol. 250.
Baggiolini, M. et al. "Human Chemokines: An Update", *Annu. Rev. Immunol.*, 1997, pp. 675-705, vol. 15.
Brown, A. R. et al. "The Total Chemical Synthesis of Monocyte Chemotactic Protein-1 (MCP-1)", *Journal of Peptide Science*, 1996, pp. 40-46, vol. 2.
Chuang, V. et al. "Pharmaceutical Strategies Utilizing Recombinant Human Serum Albumin", *Pharmaceutical Research*, May 2002, pp. 569-577, vol. 19, No. 5.
Clackson, T. et al. "Making antibody fragments using phage display libraries", *Nature*, Aug. 15, 1991, pp. 624-628, vol. 352.
Dougherty, D. A. et al. "Unnatural amino acids as probes of protein structure and function", *Current Opinion in Chemical Biology*, 2000, pp. 645-652, vol. 4.
Ferreira, B. R. et al. "Saliva of *Rhipicephalus sanguineus* tick impairs T cell proliferation and IFN-γ-induced macrophage microbicidal activity", *Veterinary Immunology and Immunopathology*, 1998, pp. 279-293, vol. 64.
Gendel, S. M. "Sequence Analysis for Assessing Potential Allergenicity", *Ann N.Y. Acad. Sci.*, 2002, pp. 87-98, vol. 964.
Gillespie, R. D. et al. "Identification of an IL-2 Binding Protein in the Saliva of the Lyme Disease Vector Tick, *Ixodes scapularis*", *The Journal of Immunology*, 2001, pp. 4319-4327, vol. 166.
Goding, J.W. "Production of Monoclonal Antibodies", Chapter 3 in *Monoclonal Antibodies: Principles and Practice*, 1986, pp. 59-103, Second Edition, Harcourt Brace Jovanovich, Publishers.
Hajnicka, V. et al. "Manipulation of host cytokine network by ticks: a potential gateway for pathogen transmission", *Parasitology*, 2005, pp. 333-342, vol. 130.
Harris, J. M. et al. "Effect of Pegylation on Pharmaceuticals", *Nature Review Drug Discovery*, Mar. 2003, pp. 214-221, vol. 2.
Hill, C.A. et al. "A method for extraction and analysis of high quality genomic DNA from ixodid ticks", *Medical and Veterinary Entomology*, 2003, pp. 224-227, vol. 17.
Hoogenboom, H. R. et al. "By-passing Immunisation Human Antibodies from Synthetic Repertoires of Germline $V_H$ Gene Segments Rearranged in Vitro", *J. Mol. Biol.*, 1992, pp. 381-388, vol. 227.
Hruby, V. J. et al. "Conformational and Topographical Considerations in Designing Agonist Peptidomimetics from Peptide Leads", *Current Medicinal Chemistry*, 2000, pp. 945-970, vol. 7.
Jensen, K. K. et al. "Disruption of CCL21-Induced Chemotaxis In Vitro and In Vivo by M3, a Chemokine-Binding Protein Encoded by Murine Gammaherpesvirus 68", *Journal of Virology*, Jan. 2003, pp. 624-630, vol. 77, No. 1.
Jones, P. T. et al. "Replacing the complementarity-determining regions in a human antibody with those from a mouse", *Nature*, May 29, 1986, pp. 522-525, vol. 321.
Kocakova, P. et al. "Effect of fast protein liquid chromatography fractionated salivary gland extracts from different ixodid tick species on interleukin-8 binding to its cell receptors", *Folia parasitologica*, 2003, pp. 79-84, vol. 50.
Luo, Y. et al. "Novel biomaterials for drug delivery", *Expert Opin. Ther. Patents*, 2001, pp. 1395-1410, vol. 11, No. 9.

(Continued)

*Primary Examiner*—Christine J Saoud
*Assistant Examiner*—Jon M Lockard
(74) *Attorney, Agent, or Firm*—Saliwanchik, Lloyd & Saliwanchik

(57) ABSTRACT

A novel CC-chemokine binding protein is isolated from the saliva of *Rhipicephalus sanguineus*. Compounds prepared in accordance with the present invention can be used as anti-inflammatory and immunomodulatory compounds and in the treatment or prevention of CC-chemokine-related diseases.

31 Claims, 28 Drawing Sheets

OTHER PUBLICATIONS

Madden, R. D. et al. "A proteomics approach to characterizing tick salivary secretions", *Experimental and Applied Acarology*, 2002, pp. 77-87, vol. 28.

Marshall, S. A. et al. "Rational design and engineering of therapeutic proteins", *Drug Discovery Today*, Mar. 5, 2003, pp. 212-221, vol. 8, No. 5.

Mulenga, A. et al. "Issues in tick vaccine development: identification and characterization of potential candidate vaccine antigens", *Microbes and Infection*, 2000, pp. 1353-1361, vol. 2.

Murphy, L. R. et al. "Simplified amino acid alphabets for protein fold recognition and implications for folding", *Protein Engineering*, 2000, pp. 149-152, vol. 13, No. 3.

Murrell, A. et al. "A Total-Evidence Phylogeny of Ticks Provides Insight into the Evolution of Life Cycles and Biogeography", *Molecular Phylogenetics and Evolution*, Nov. 2001, pp. 244-258, vol. 21, No. 2.

Nilsson, J. et al. "Affinity Fusion Strategies for Detection, Purification, and Immobilization of Recombinant Proteins", *Protein Expression and Purification*, 1997, pp. 1-16, vol. 11.

Pearson, W. R. "Flexible Sequence Similarity Searching with the FASTA3 Program Package", *Methods in Molecular Biology*, 2000, pp. 185-219, vol. 132.

Pillai, O. et al. "Polymers in Drug Delivery", *Current Opinion in Chemical Biology*, 2001, pp. 447-451, vol. 5.

Rapoport, T.A. et al. "Protein transport across the eukaryotic endoplasmic reticulum and bacterial inner membranes", *Annu. Rev. Biochem.*, 1996, pp. 271-303, vol. 65.

Rogov, S. I. et al. "A numerical measure of amino acid residues similarity based on the analysis of their surroundings in natural protein sequences", *Protein Engineering*, 2001, pp. 459-463, vol. 14, No. 7.

Scatchard, G. "The Attractions of Proteins for Small Molecules and Ions", *Ann NY Acad. Sci.*, 1949, pp. 660-672, vol. 51.

Schellekens, H. "Bioequivalence and the Immunogenicity of Biopharmaceuticals", *Nature Reviews Drug Discovery*, Jun. 2002, pp. 457-462, vol. 1.

Ullmann, A. J. et al. "A preliminary linkage map of the tick, *Ixodes scapularis*", *Experimental and Applied Acarology*, 2002, pp. 107-126, vol. 28.

Vaitukaitis, J. et al. "A Method for Producing Specific Antisera with Small Doses of Immunogen", *J Clin Endocr*, 1971, pp. 988-991, vol. 33.

Valenzuela, J. G. "Editorial: Exploring the Messages of the Salivary Glands of *Ixodes ricinus*", *Am. J. Trop. Med. Hyg.*, 2002, pp. 223-224, vol. 66, No. 3.

Van Valkenburgh, H. A. et al. "Coexpression of Proteins with Methionine Aminopeptidase and/or N-Myristoyltransferase in *Escherichia coli* to Increase Acylation and Homogeneity of Protein Preparations", *Methods in Enzymology*, 2002, pp. 186-183, vol. 344.

Vasserot, A. P. et al. "Optimization of protein therapeutics by directed evolution", *Drug Discovery Today*, Feb. 2003, pp. 118-126, vol. 8, No. 3.

Villain, M. et al. "Covalent capture: a new tool for the purification of synthetic and recombinant polypeptides", *Chemistry & Biology*, 2001, pp. 673-679, vol. 8.

Wang, H. "Molecular individuality: polymorphism of salivary gland proteins in three species of ixodid tick", *Experimental and Applied Acarology*, 1999, pp. 969-975, vol. 23.

Ward, E. S. et al. "Binding activities of a repertoire of single immunoglobulin variable domains secreted from *Escherichia coli*", *Nature*, Oct. 12, 1989, pp. 544-546, vol. 341.

Kohler, G. et al. "Continuous cultures of fused cells secreting antibody of predefined specificity", *Nature*, Aug. 7, 1975, pp. 495-497, vol. 256.

Figure 1

```
  1      CGGCCGGGGA CTATACTGAT CAGTTGAGTG GCAACTGGGC AGGTATATCC A ATG GCT
                                                                 Met Ala

58      TTT AAA TAT TGG TTC GTT TTT GCG GCC GTC CTG TAT GCT CGA CAA TGG CTC
         Phe Lys Tyr Trp Phe Val Phe Ala Ala Val Leu Tyr Ala Arg Gln Trp Leu

109      AGC ACT AAA TGC GAA GTG CCA CAA ATG ACT TCG TCC TCC GCG CCG GAT CTT
         Ser Thr Lys Cys Glu Val Pro Gln Met Thr Ser Ser Ser Ala Pro Asp Leu

160      GAA GAG GAG GAC GAT TAC ACA GCA TAT GCA CCG CTG ACG TGC TAT TTT ACA
         Glu Glu Glu Asp Asp Tyr Thr Ala Tyr Ala Pro Leu Thr Cys Tyr Phe Thr

211      AAT TCC ACG CTT GGT CTG CTG GCC CCC CCA AAT TGC TCC GTG CTT TGC AAC
         Asn Ser Thr Leu Gly Leu Leu Ala Pro Pro Asn Cys Ser Val Leu Cys Asn

262      AGT ACC ACA ACT TGG TTT AAT GAA ACT TCG CCA AAC AAT GCT TCG TGT TTG
         Ser Thr Thr Thr Trp Phe Asn Glu Thr Ser Pro Asn Asn Ala Ser Cys Leu

313      CTG ACT GTG GAT TTT CTT ACA CAG GAC GCC ATT CTA CAA GAA AAC CAA CCG
         Leu Thr Val Asp Phe Leu Thr Gln Asp Ala Ile Leu Gln Glu Asn Gln Pro

364      TAC AAC TGC AGT GTG GGA CAC TGT GAT AAT GGG ACT TGC GCC GGG CCC CCT
         Tyr Asn Cys Ser Val Gly His Cys Asp Asn Gly Thr Cys Ala Gly Pro Pro

415      CGA CAC GCT CAG TGC TGG TAG AGGACACGGA ACCAGGAATG ATGCACCTCG
         Arg His Ala Gln Cys Trp

466      CAGCTGCTCA CACTATGTAT AATAAAAAT GGAGCATTTT GAGCCGAAAA AAAAAAAAA
526      AAAAAAAAAA AAAAACATGT CGGCCGCCT
```

Figure 3

```
                    Evasin-4 PCR2F
     ─────────────────────────────────────────────▶
                                            spupa PCR1F
                                     ──────────────────────────▶
  1  ggggacaagt ttgtacaaaa aagcaggctt cgccacc atg aga gcc ctg ctg gcg cgc
                                             M   R   A   L   L   A   R
                                                                        ──▶
 59  ctg ctt ctc tgc gtc ctg gtc gtg agc gac agt aaa ggc gga tcc ccg aat
      L   L   L   C   V   L ◀ V    V   S   D   S   K   G   G   S   P   N
                                         Spupa-GSPNS R
                       6H-GSPNS-Evasin-4F
     ──────────────────────────────────────────────────────────▶
110  tcc cat cac cat cac cat cac gga tcc ccg aat tcc ctg gag acc gat gaa
      S   H   H   H   H   H   H   G   S   P   N   S   L   E   T   D   E
     ◀─────────────────

SPNS-LETD-Evasin-4F
     ──────────────────────▶
161  gtg cca caa atg act tcg tcc tcc gcg ccg gat ctt gaa gag gag gac gat
      V   P   Q   M   T   S   S   S   A   P   D   L   E   E   E   D   D 212  tac aca gca tat gca ccg ctg acg tgc tat ttt aca aat tcc acg ctt ggt
      Y   T   A   Y   A   P   L   T   C   Y   F   T   N   S   T   L   G 263  ctg ctg gcc ccc cca aat tgc tcc gtg ctt tgc aac agt acc aca act tgg
      L   L   A   P   P   N   C   S   V   L   C   N   S   T   T   T   W 314  ttt aat gaa act tcg cca aac aat gct tcg tgt ttg ctg act gtg gat ttt
      F   N   E   T   S   P   N   N   A   S   C   L   L   T   V   D   F 365  ctt aca cag gac gcc att cta caa gaa aac caa ccg tac aac tgc agt gtg
      L   T   Q   D   A   I   L   Q   E   N   Q   P   Y   N   C   S   V 416  gga cac tgt gat aat ggg act tgc gcc ggg ccc cct cga cac gct cag tgc
      G   H   C   D   N   G   T   C   A   G   P   P   R   H   A   Q   C
                                                      ◀────────────────
                                                         Evasin-4 PCR1R
467  tgg tga aacccagctt tcttgtacaa agtggtcccc
      W   -
     ◀──────────────────
       ◀────────────────────────────────────────
              Evasin-4 PCR2R
```

Figure 4    pEAK12d-PAC_upa-SP-hIL18BP-6His-V1
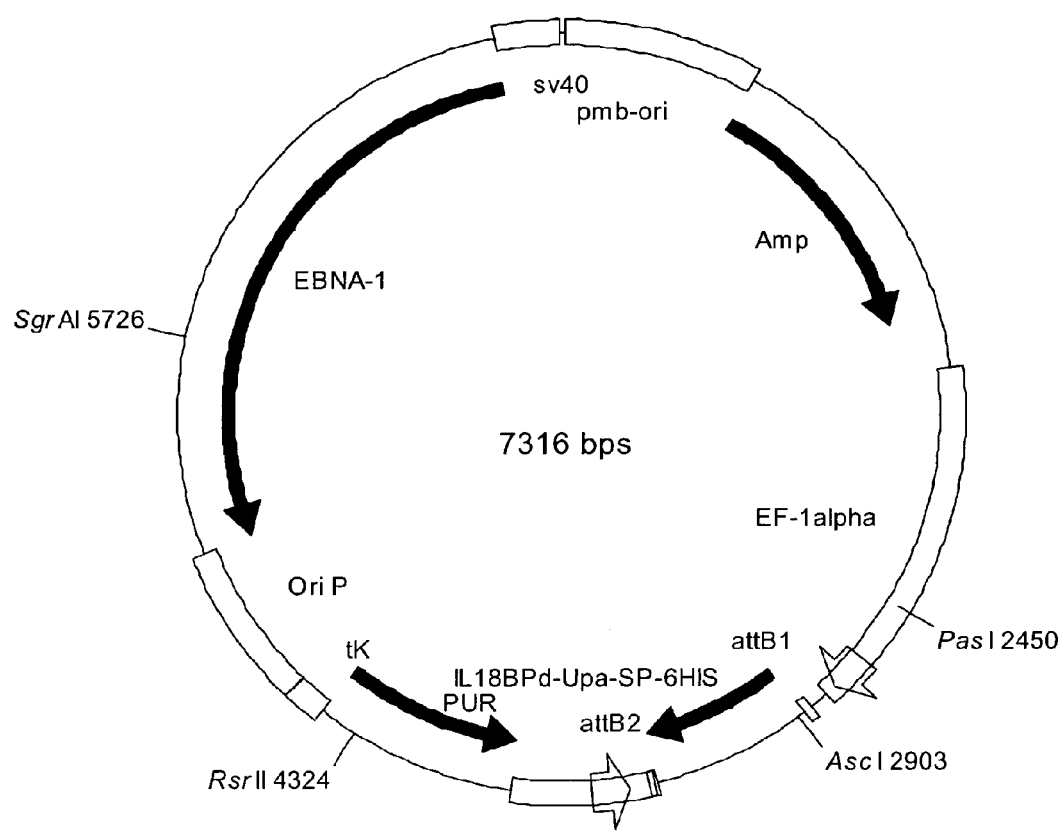

Figure 5  pEXP-Lib-Evasin-4
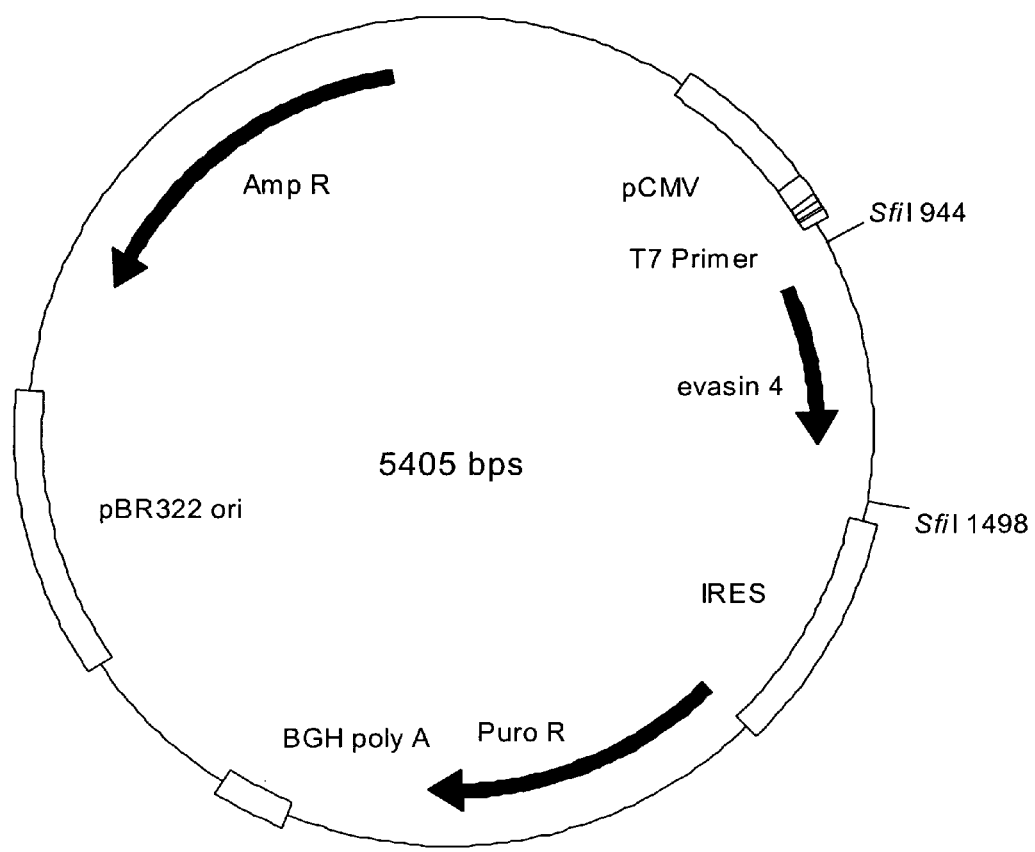

Figure 6    pDONR221-spUPA-6His-Evasin-4
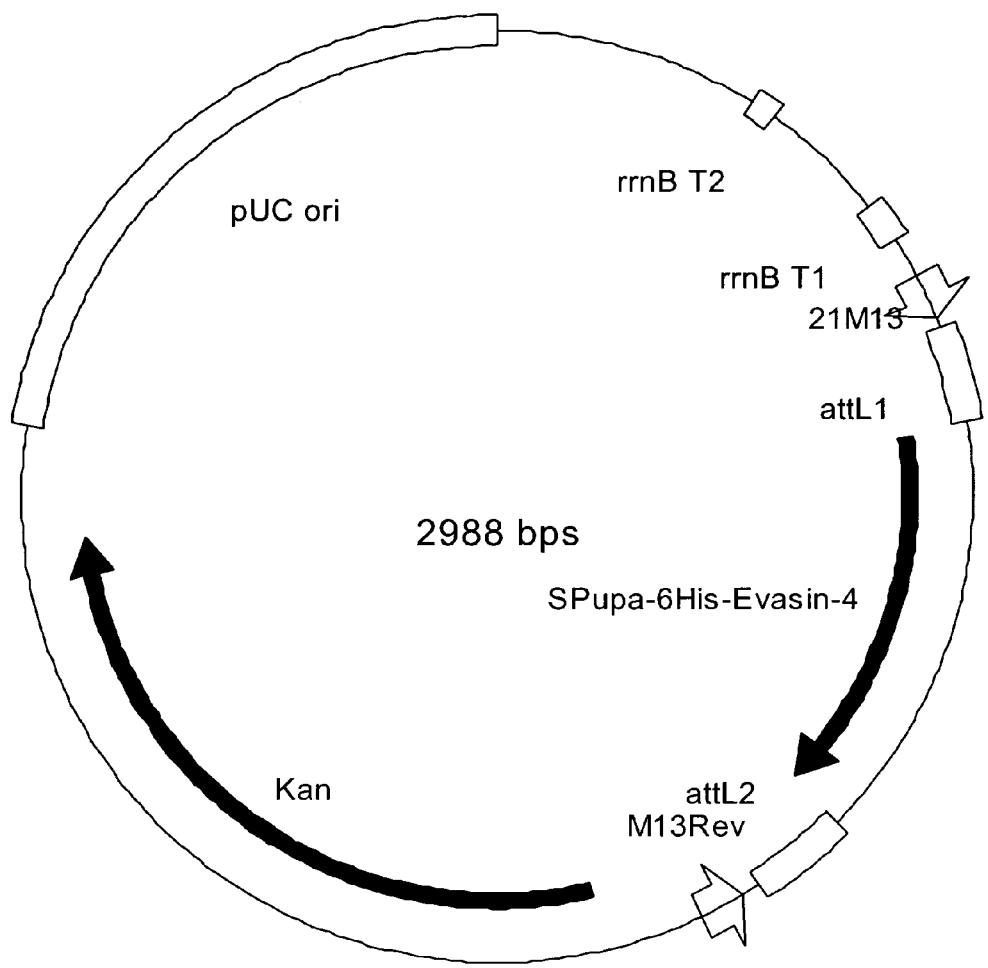

Figure 7          pEAK12d-spUPA-6His-Evasin-4
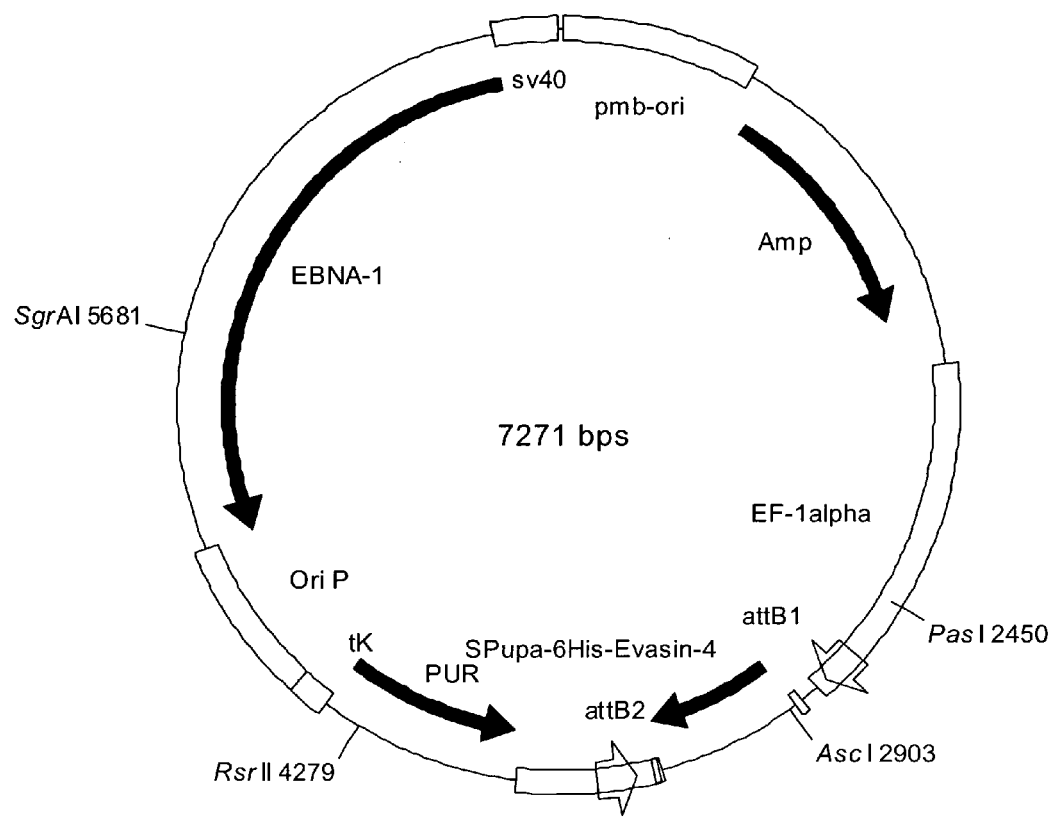

Figure 8    pDEST8-spUPA-6His-Evasin-4
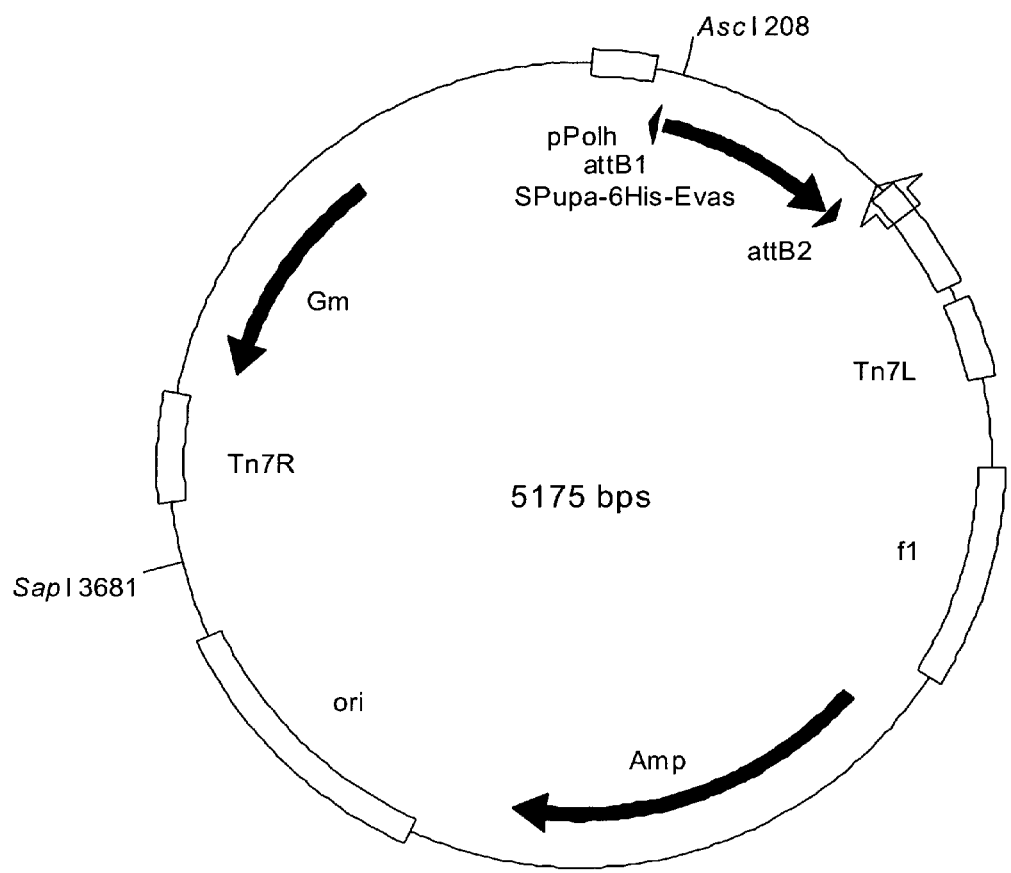

Figure 9
A
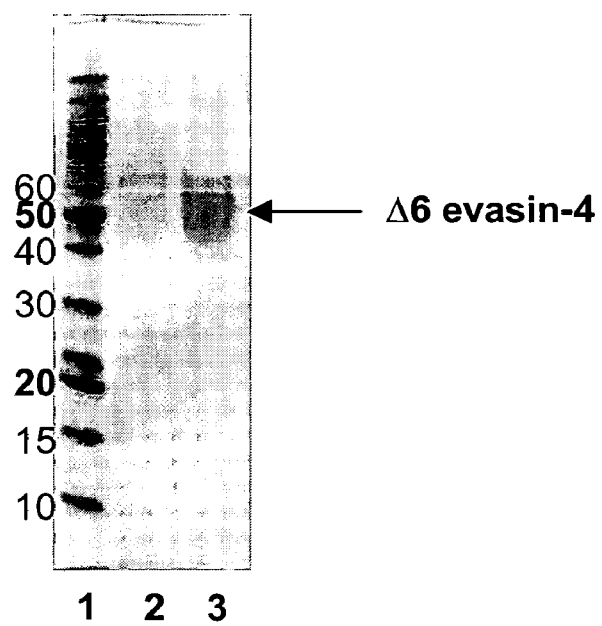
B
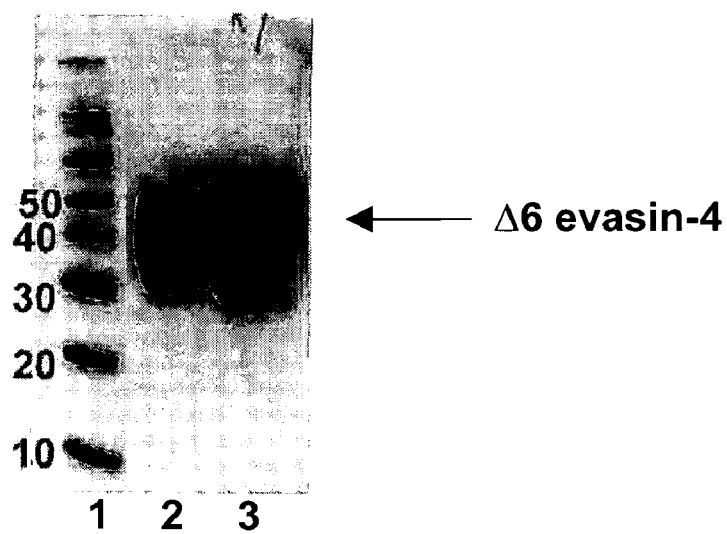

Figure 10
A
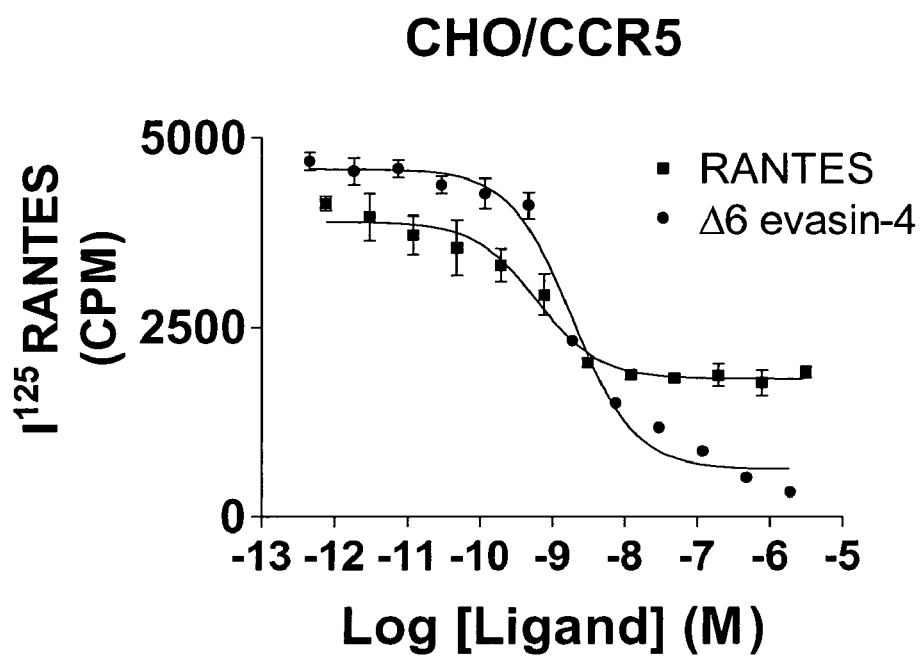
B
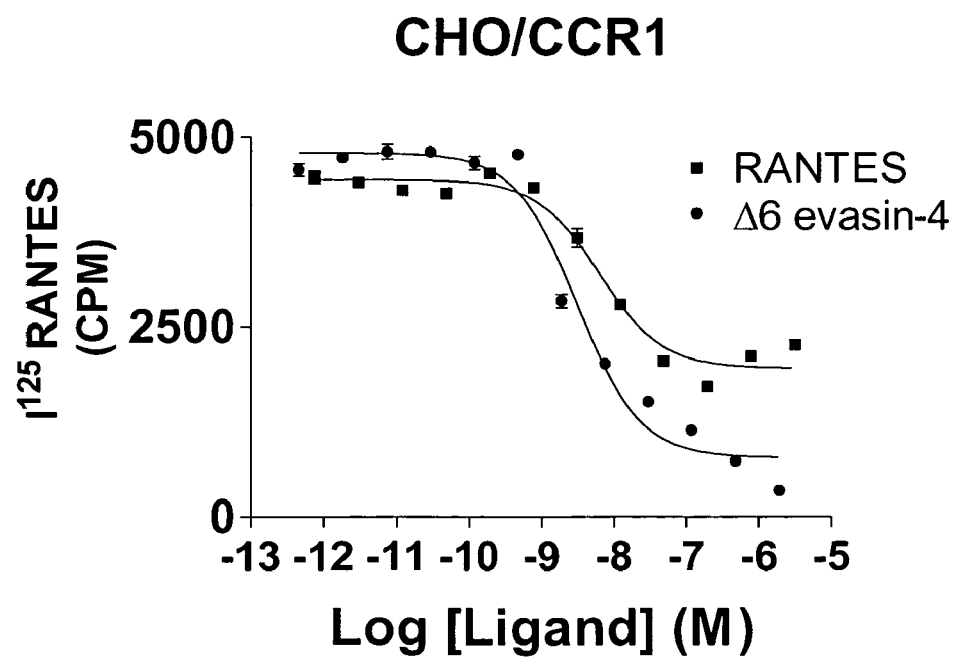

A

B

C

D

E

F

G

H

I

J

K

L

Figure 12
A
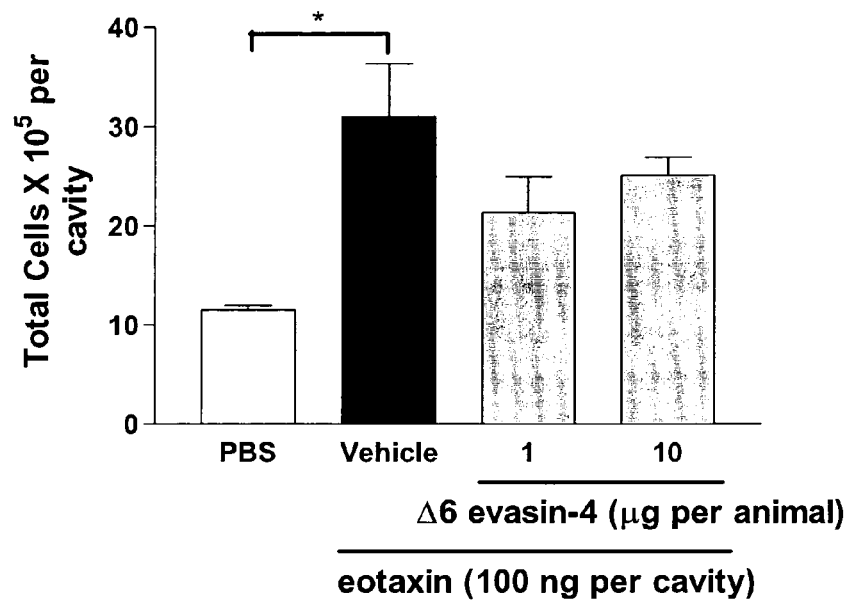
B
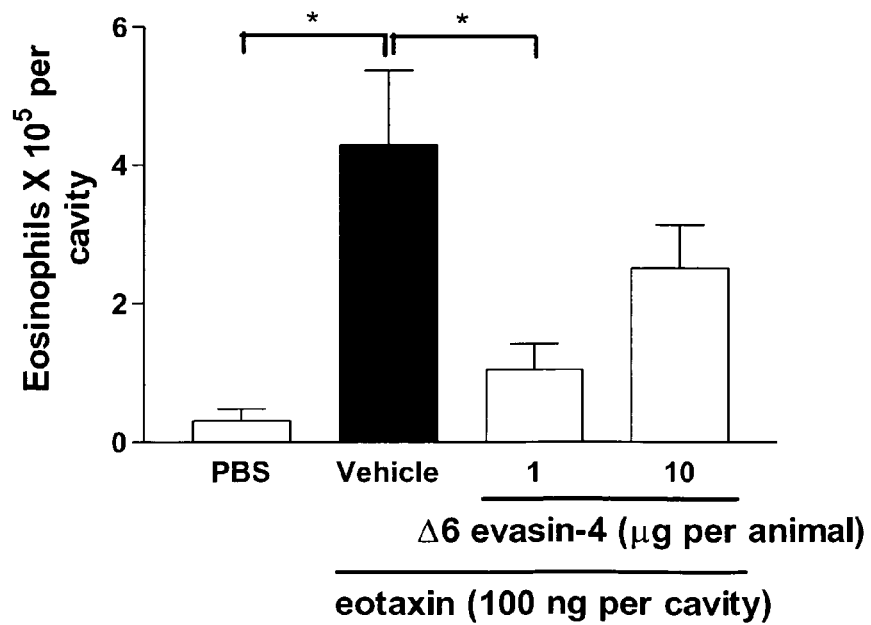

```
  1  ATG AGA GCC CTG CTG GCG CGC CTG CTT CTC TGC GTC CTG GTC GTG AGC GAC AGT
      M   R   A   L   L   A   R   L   L   L   C   V   L   V   V   S   D   S

→
 55  AAA GGC GGA TCC CCG AAT TCC CAT CAC CAT CAC CAT CAC GGA TCC CCG AAT TCC
      K   G   G   S   P   N   S   H   H   H   H   H   H   G   S   P   N   S
             6His-WLSTK-Evasin-4 F                                         ◄
     ──────────────────────────────────────────►
109  CTG GAG ACC GAT TGG CTC AGC ACT AAA TGC GAA GTG CCA CAA ATG ACT TCG TCC
      L   E   T   D   W   L   S   T   K   C   E   V   P   Q   M   T   S   S
     ◄-----------------------------------------
             6His-WLSTK-Evasin-4 R
163  TCC GCG CCG GAT CTT GAA GAG GAG GAC GAT TAC ACA GCA TAT GCA CCG CTG ACG
      S   A   P   D   L   E   E   E   D   D   Y   T   A   Y   A   P   L   T 217  TGC TAT TTT ACA AAT TCC ACG CTT GGT CTG CTG GCC CCC CCA AAT TGC TCC GTG
      C   Y   F   T   N   S   T   L   G   L   L   A   P   P   N   C   S   V 271  CTT TGC AAC AGT ACC ACA ACT TGG TTT AAT GAA ACT TCG CCA AAC AAT GCT TCG
      L   C   N   S   T   T   T   W   F   N   E   T   S   P   N   N   A   S 325  TGT TTG CTG ACT GTG GAT TTT CTT ACA CAG GAC GCC ATT CTA CAA GAA AAC CAA
      C   L   L   T   V   D   F   L   T   Q   D   A   I   L   Q   E   N   Q 379  CCG TAC AAC TGC AGT GTG GGA CAC TGT GAT AAT GGG ACT TGC GCC GGG CCC CCT
      P   Y   N   C   S   V   G   H   C   D   N   G   T   C   A   G   P   P

433  CGA CAC GCT CAG TGC TGG
      R   H   A   Q   C   W
```

CC-CHEMOKINE BINDING TICK PROTEINS

CROSS-REFERENCE TO RELATED APPLICATION

This application is the U.S. national stage application of International Patent Application No. PCT/EP2007/001361, filed Feb. 16, 2007, which claims the benefit of U.S. Provisional Patent Application No. 60/774,090, filed Feb. 16, 2006, the disclosures of which are hereby incorporated by reference in their entireties, including all figures, tables and amino acid or nucleic acid sequences.

FIELD OF THE INVENTION

The invention relates to novel antagonists of CC-chemokines, particularly antagonists of CCL5 and CCL11, and their uses, particularly as anti-inflammatory or immuno-modulatory compounds and in the treatment or prevention of CC-chemokine-related diseases.

BACKGROUND OF THE INVENTION

Chemokines are small, secreted pro-inflammatory proteins, which mediate directional migration of leukocytes from the blood to the site of injury. Depending on the position of the conserved cysteines characterizing this family of proteins, the chemokine family can be divided structurally into C, CC, CXC and $CX_3C$ chemokines that bind to a series of membrane receptors (Baggiolini M et al., 1997). These membrane receptors, all heptahelical G-protein coupled receptors, allow chemokines to exert their biological activity on the target cells, which may present specific combinations of receptors according to their state and/or type. The physiological effects of chemokines result from a complex and integrated system of concurrent interactions: the receptors often have overlapping ligand specificity, so that a single receptor can bind different chemokines. A single chemokine can bind to different receptors as well.

Studies on structure-activity relationships indicate that chemokines have two main sites of interaction with their receptors, the flexible amino-terminal region and the conformationally rigid loop that follows the second cysteine. Chemokines are thought to dock onto receptors by means of the loop region, and this contact is believed to facilitate the binding of the amino-terminal region that results in receptor activation.

Usually, chemokines are produced at the site of injury and cause leukocyte migration and activation, playing a fundamental role in inflammatory, immune, homeostatic, hematopoietic, and angiogenic processes. Thus, these molecules are considered good target candidates for therapeutic intervention in diseases associated with such processes. The inhibition of chemokines, or of their receptors, can reduce leukocyte differentiation, maturation, recruitment and activation, as well as other pathological processes related to angiogenesis or arteriosclerosis (Baggiolini M, 2001).

In addition to mutant inhibitory chemokines, antibodies and peptide and small molecule inhibitors blocking the receptors, the search for effective chemokine antagonists has also been extended to a series of viruses and other organisms that, when entering into contact with human or mammal hosts, produce potent immuno-modulatory activities affecting the host.

The viral mimicry of cytokines, chemokines, and their receptors may indicate strategies of immune modulation for developing therapeutic products. Recently, immuno-modulatory factors expressed by haematophagous arthropods (such as mosquitoes, sandflies and ticks) have been reviewed (Gillespie, R D et al, 2001).

In particular, the salivary glands of ticks produce a complex mixture of bioactive molecules having, anti-inflammatory, anti-haemostatic and anti-immune activities. These include bioactive proteins that control histamine, bind immunoglobulins, or inhibit the alternative complement cascade or other proteases.

Despite the large amount of literature, only a few articles list cDNA sequences identified by random sequencing and differential screens of libraries generated from various tick tissues and/or species. However, the large majority of these sequences have not been characterized biochemically or functionally, and many annotations are entered only on the basis of sequence similarity with known proteins involved in basic cellular functions, such as those previously characterised in tick salivary glands for enzymatic activities or inducing an antibody response. In particular, there is no indication of tick proteins acting as CC-chemokine binding proteins and/or functioning as CC-chemokine antagonists.

SUMMARY OF THE INVENTION

Surprisingly, it has been found that the saliva of *Rhipicephalus sanguineus* (common brown dog tick) contains a novel protein termed herein evasin-4, which binds CC-chemokines and inhibits their activity. Evasin-4 was cloned from a *Rhipicephalus sanguineus* cDNA library, and expressed in mammalian cells. This protein, as well as derivatives, fragments or mimetics thereof, can be used therapeutically, e.g., as antagonists of CC-chemokines in mammalian organisms, or as targets for vaccination and for the control of ticks and of tick-borne pathogens.

A first aspect of the invention thus relates to a polypeptide comprising the amino acid sequence of evasin-4 or of a fragment or analog thereof. Preferred polypeptides of this invention bind a CC-chemokine, and inhibit its biological activity. A specific example of such a polypeptide is evasin-4 or a fragment thereof.

A second aspect of the invention relates to nucleic acid molecules encoding a polypeptide as defined above. Such nucleic acids also include oligonucleotides isolated from them and vectors containing said molecules, in particular expression vectors.

A third aspect of this invention resides in antibodies that selectively bind the polypeptides as defined above.

A fourth aspect of this invention relates to host cells and transgenic non-human animals expressing a polypeptide as defined above, as well as methods of producing such cells and transgenic non-human animals.

A fifth aspect of this invention is a process for preparing a polypeptide as defined above, typically using recombinant technologies.

A sixth aspect of the invention is a pharmaceutical (including a vaccine or immunogenic) composition comprising a polypeptide or nucleic acid molecule as defined above and a pharmaceutically acceptable carrier or vehicle.

A seventh aspect of the invention relates to the use of a polypeptide or nucleic acid molecule as defined above as a medicament, in particular for the preparation of a medicament for regulating an immune or inflammatory response in a mammal, as well as to corresponding methods for treatment.

Other features and advantages of the invention will be apparent from the following detailed description.

DESCRIPTION OF THE FIGURES

FIG. 1: Nucleotide sequence of evasin-4 cDNA sequence (SEQ ID NO: 3) with translation (SEQ ID NO: 5) of the open reading frame (ORF). The signal sequence (amino acids 1-17, predicted by the SIGNALJ algorithm is underlined. The predicted polyadenylation site is boxed. The cysteine residues present in the mature protein are highlighted. The potential N-linked glycosylation sites are in bold type.

FIG. 3: Nucleotide sequence (SEQ ID NO: 25) and translation (SEQ:ID NO: 29)8) of a Gateway cloning system compatible cDNA encoding amino acids 24-127 of the evasin-4 ORF (Δ6 evasin-4) flanked at the 5' end by the uPA signal peptide sequence (amino acids 1-20), a 5 amino acid linker sequence (GSPNS) and a 6 histidine tag and flanked at the 3' end by a stop codon. The arrows indicate the position and sense of PCR primers used to generate the cDNA (primer sequences are listed in Table III). Start and stop codons are in bold. The predicted signal peptide sequence is shown in italics.

FIG. 4: Map of pEAK12d-PAC_upa-SP-hIL18BP-6His-V1 vector used as a template to amplify the signal peptide sequence of urokinase plasminogen activator (UPA)

FIG. 5: Map of pEXP-Lib-Evasin-4 vector used as a template to amplify the cDNA of evasin-4.

FIG. 6: Map of pDONR221-spUPA-6His-Evasin-4 (Gateway entry vector).

FIG. 7: Map of pEAK12d-spUPA-6His-Evasin-4. Gateway expression vector for production of Δ6 evasin-4 in human embryonic kidney (HEK293/EBNA) cells.

FIG. 8: Map of pDEST8-spUPA-6His-Evasin-4. Gateway expression vector for expression of Δ6 evasin-4 in TN5 (insect) cells.

FIG. 9: A) 10% SDS-polyacrylamide gel (SDS-PAGE) stained with Coomassie blue showing Δ6 evasin-4 purified from HEK293 cells using Ni$^{2+}$ affinity chromatography. Lane 1, Molecular weight markers; Lanes 2 and 3, Recombinant Δ6 evasin-4 fractions after elution from the Ni$^{2+}$ affinity column. B) Western blot analysis after transfer from the SDS-PAGE gel to a nitrocellulose membrane using a mouse anti-6H is antibody as the first antibody and a rabbit anti-mouse antibody as the second antibody and detection by chemi-luminescence.

FIG. 10: Inhibition of binding of CCL5/RANTES to CCR5 (A) and CCR1 (B) by Δ6 evasin-4 in equilibrium competition binding assays. The IC$_{50}$ values are 3 nM for CCR5 and 7 nM for CCR1.

FIG. 13: Nucleotide sequence SEQ ID NO: 25) and translation (SEQ ID NO: 29) of a Gateway cloning system compatible cDNA encoding amino acids 18-127 of the evasin-4 ORF (FL evasin-4) flanked at the 5' end by the uPA signal peptide sequence (amino acids 1 20), a 5 amino acid linker sequence (GSPNS), a 6 histidine tag, a second 5 amino acid linker sequence, and a caspase 8 cleavage site sequence (LETD); and flanked at the 3' end by a stop codon. The arrows indicate the position and sense of PCR primers used to generate the cDNA (primer sequences are listed in Table III). Start and stop codons are in bold. The predicted signal peptide sequence is shown in italics.

DETAILED DESCRIPTION OF THE INVENTION

Figure 2:
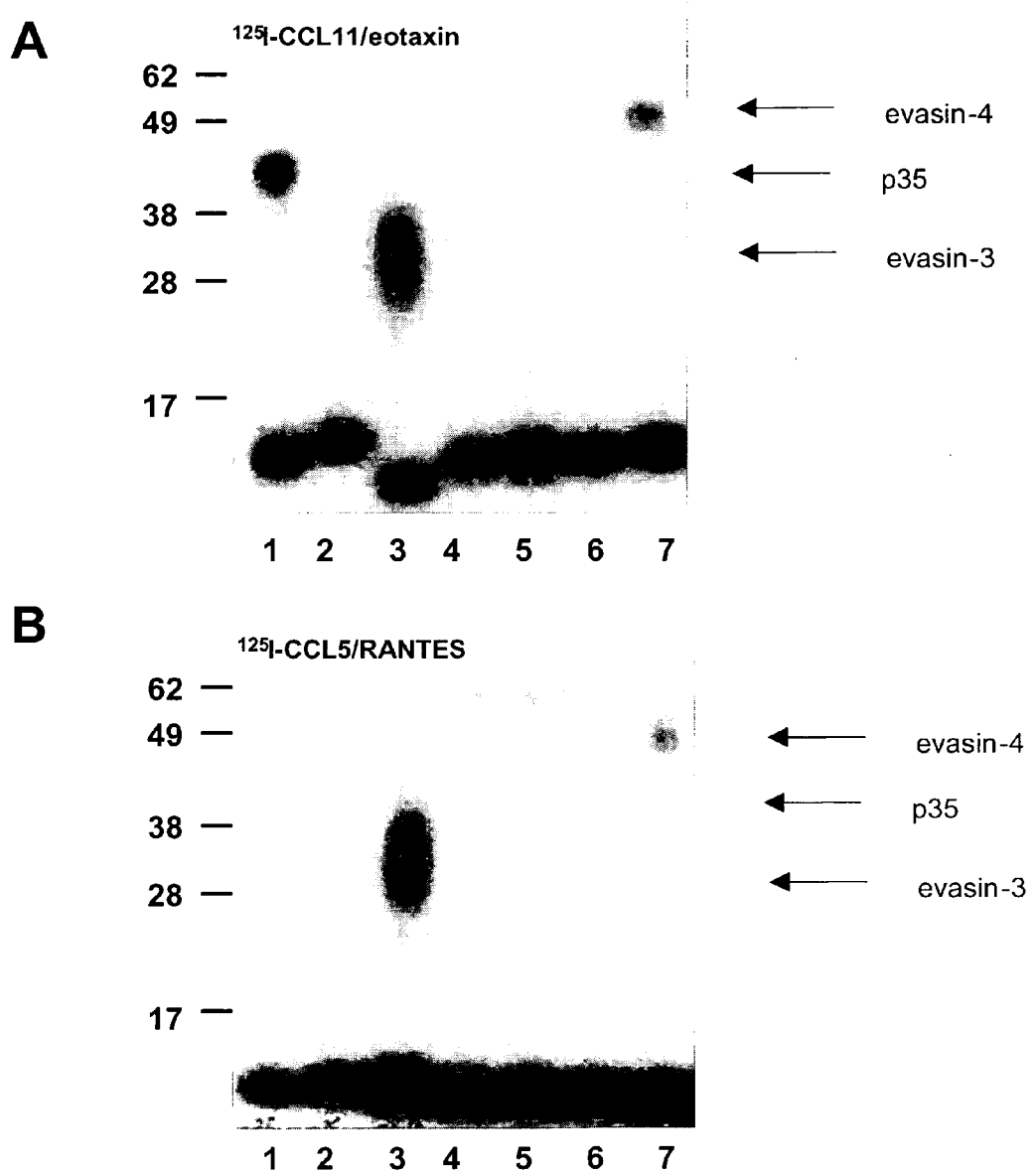
FIG. 2:
(A) Auto-radiograph of the SDS-PAGE gel showing the complex formed by cross-linking of $^{125}$I-labeled CC-chemokine CCL11/eotaxin with supernatants from HEK293 cells transfected with recombinant evasin-4, using the cross-linker BS3. Lane 1, the viral CC-chemokine binding protein (p35) cross-linked to $^{125}$I-CCL11/eotaxin (positive control); Lane 2, the viral CC-chemokine binding protein (p35) incubated with $^{125}$I-eotaxin in the absence of BS3; Lane 3, HEK293 cell culture supernatant from evasin-3 transfectants cross-linked with $^{125}$I-CXCL8/IL-8 (positive control); Lane 4, non-transfected HEK293 cell culture supernatant cross-linked with $^{125}$I-CCL11/eotaxin and BS3 (negative control); Lanes 5 and 6, HEK 293 cell culture supernatant from negative pools incubated with CCL11/eotaxin and BS3; Lane 7, HEK293 cell culture supernatant from pool 10.7 incubated with $^{125}$I-CCL11/eotaxin and BS3.
(B) Auto-radiograph of the SDS-PAGE gel showing the complex formed by cross-linking of $^{125}$I-labeled CC-chemokine CCL5/RANTES with supernatants from HEK293 cells transfected with recombinant evasin-4, using the crosslinker BS3. Lane 1, the viral CC-chemokine binding protein (p35) cross-linked to $^{125}$I-CCL5/RANTES (positive control); Lane 2, the viral CC-chemokine binding protein (p35) incubated with $^{125}$I-RANTES in the absence of BS3; Lane 3, HEK293 cell culture supernatant from evasin-3 transfectants cross-linked with $^{125}$I-CXCL8/IL-8 (positive control); Lane 4, non-transfected HEK293 cell culture supernatant cross-linked with $^{125}$I-CCL5/RANTES and BS3 (negative control); Lanes 5 and 6, HEK 293 cell culture supernatant from negative pools incubated with CCL5/RANTES and BS3; Lane 7, HEK293 cell culture supernatant from pool 10.7 incubated with $^{125}$I-CCL5/RANTES and BS3.

The present invention provides novel compositions and methods for regulating chemokine activity. More particularly, the present invention discloses a novel protein having CC-chemokine binding properties, that can be used to inhibit chemokine action. The examples show that this protein, derived from tick saliva, can be expressed and purified in recombinant form, and effectively binds CC-chemokines and will thus inhibit their action, e.g., the specific chemotactic response of cells induced by a CC-chemokine.

A first aspect of the invention thus resides in an evasin-4 polypeptide, i.e., any polypeptide comprising the amino acid sequence of evasin-4 or of a fragment or analog thereof. Preferred polypeptides of this invention bind a CC-chemokine, in particular CCL5 (also referred to as RANTES) and CCL-11 (also referred to as eotaxin), and inhibit the activity of said chemokine. Particular polypeptides of this invention are selected from the group consisting of:

a) a protein comprising an amino acid sequence of evasin-4 identified by SEQ ID NO: 5;

b) a protein comprising an amino acid sequence of mature evasin-4 identified by SEQ ID NO: 6;

c) a protein encoded by a nucleic acid molecule capable of hybridization to a nucleic acid sequence encoding a protein of a) or b) under stringent conditions, said nucleic acid molecule encoding a protein that binds a CC-chemokine and inhibits the activity of said chemokine;

d) a protein at least about 70% identical in amino acid sequence to a protein of a), b), or c), and that binds a CC-chemokine and inhibits the activity of said chemokine;

e) a protein comprising a fragment of a protein of a), b), c), or d), which fragment retains the ability to bind a CC-chemokine and inhibit the activity of said chemokine; and f) a protein comprising a fragment of a protein of a), b), c), d), or e), which fragment has an immunomodulatory activity.

In a preferred embodiment, the protein is selected from the group consisting of:

a) a protein having an amino acid sequence of evasin-4 identified by SEQ ID NO: 5;

b) a protein having an amino acid sequence of mature evasin-4 identified by SEQ ID NO 6;

c) a protein comprising a fragment of a protein of a), or b), which fragment binds a CC-chemokine and inhibits the activity of said chemokine;

d) a protein comprising a fragment of a protein of a), or b) which fragment has an immunomodulatory activity.

In another aspect, the invention relates to an active mutant of a protein defined above, in which mutant one or more amino acid residues have been added, deleted, or substituted and which mutant binds a CC-chemokine and inhibits the activity of said chemokine.

The polypeptides of the invention can be in a mature form, resulting from one or more post-translational modifications (glycosylation, phosphorylation, modification with endo-/exopeptidases for eliminating the signal peptide, for example) or from the in-frame addition of sequence encoding heterologous sequences (such as tags or domains that improve the detection and/or the purification). For example, evasin-4 can be expressed as a recombinant histidine-tagged protein in the complete and mature form in both a mammalian and an insect cell line.

The polypeptides of this invention or their corresponding nucleic acids may be in isolated form (e.g., not in their natural environment), including recombinant or synthetic polypeptides and nucleic acids.

The examples show that evasin-4 polypeptides bind CC-chemokines, in particular CCL5 (also called RANTES) and CCL11 (also called Eotaxin) and it can be used to inhibit (e.g., reduce) their activity. This characterization was performed by making use of biochemical assays, including the use of radio-labelled CC-chemokines. Such activity confers a broad range of therapeutic utility to the evasin-4 polypeptides of this invention, as discussed below.

Within the context of the present invention, a fragment of a polypeptide designates any fragment comprising at least 5, 6, 7, 8, 9 or 10 consecutive amino acid residues of said polypeptide sequence. Particular fragments of this invention comprise 15, 20, 25 or more amino acid residues of an evasin-4 protein as disclosed therein. Preferred fragments retain at least one biological activity of a full-length protein, e.g., an immunogenic activity or an immuno-modulatory activity.

In this regard, within the context of the present invention, an "immuno-modulatory activity" designates any activity detected in vitro or in vivo that affects the immune response in either a positive or negative manner. Examples of such activities are immunizing activities, immuno-suppressive activities, anti-inflammatory activities, pro-/anti-apoptotic activities, or anti-tumor activities.

Alternatively the fragment can be identified as providing an immunizing activity when administered to a mammal. These fragments should have appropriate antigenic or immunogenic properties for raising an immune response when needed (for example, against ticks or tick-borne pathogenic organisms). The literature provides many examples on how such functional sequences can be identified as candidate vaccine antigens, and eventually administered with adjuvants and/or cross-linked to a carrier. (Mulenga A et al. 2000; WO 01/80881; WO 03/030931; WO 01/87270). A specific antigen or group of antigens identified in evasin-4 can be used for preventing or reducing ectoparasite infection or disease in an animal, so that the immunity of the animal to the ectoparasite is boosted by natural challenge of the animal with the ectoparasite (WO 95/22603). Finally, the fragment can be also used for raising antibodies directed to the entire protein for screening or diagnostic applications.

The properties of evasin-4 defined above, and exemplified herein using recombinant variants of this sequence, can be maintained, or even potentiated, in the active mutants. This category of molecules includes natural or synthetic analogs of said sequence, wherein one or more amino acid residues have been added, deleted, or substituted, provided they display the same biological activity characterized in the present invention at comparable or higher levels, as determined by means disclosed in the Examples below.

In particular, the term "active" means that such alternative compounds should maintain, or even potentiate, the CC-chemokine binding and immuno-modulatory properties of evasin-4.

Active mutant molecules can be generated by site-directed mutagenesis techniques, combinatorial technologies at the level of encoding DNA sequence (such as DNA shuffling, phage display/selection), or by computer-aided design studies, or any other known technique suitable thereof, which provide a finite set of substantially corresponding mutated or shortened peptides or polypeptides. These alternative molecules can be routinely obtained and tested by one of ordinary skill in the art using the teachings presented in the prior art and in the Examples below.

In accordance with the present invention, preferred changes in these active mutants are commonly known as "conservative" or "safe" substitutions, and involve non-basic residues. Conservative amino acid substitutions are those with amino acids having sufficiently similar chemical properties, in order to preserve the structure and the biological function of the molecule. It is clear that insertions and deletions of amino acids may also be made in the above defined sequences without altering their function, particularly if the insertions or deletions only involve a few amino acids, e.g., under ten, and preferably under three, and do not remove or displace amino acids which are critical to the functional conformation of a protein or a peptide.

The literature provides many models on which the selection of conservative amino acids substitutions can be performed on the basis of statistical and physicochemical studies on the sequence and/or the structure of natural protein (Rogov S I and Nekrasov A N, 2001). Protein design experiments have shown that the use of specific subsets of amino acids can produce foldable and active proteins, helping in the classification of amino acid "synonymous" substitutions which can be more easily accommodated in the protein structure, and which can be used to detect functional and structural evasin-4 homologs and paralogs (Murphy L R et al., 2000). The synonymous amino acid groups and more preferred synonymous groups for the substitutions are those defined in Table I.

However, in the context of evasin-4 sequence, specific residues may have a particular importance. For example, evasin-4 is not significantly homologous to any known proteins. Further features of evasin-4 are 7 potential N-linked glycosylation sites and 9 cysteine residues. These residues may be important for the correct folding and/or activity and should be preferably conserved in the corresponding positions of these alternative polypeptides. Alternatively, the deleted or substituted cysteines or glycosylation sites can be re-established in a different position of the protein.

Alternatively, active mutants of evasin-4 may result from sequence alterations reducing the immunogenicity of said CC-chemokine binding protein when administered to a mammal. The literature provides many examples of these sequence alterations that can be designed and introduced at this scope or for other functional optimizations that allow a safe and effective administration of a therapeutic protein, especially when it is a non-human, non-mammalian, or non-natural protein (Schellekens H, 2002). Examples of technical approaches for achieving these molecules are directed evolution (Vasserot A P et al., 2003), rational design (Marshall S A et al., 2003), bioinformatics (Gendel S M, 2002), the identification and the neutralization of CD4+ T-cell epitopes (WO 03/104263; WO 03/006047; WO 02/98454; WO 98/52976; WO 01/40281), fusion with other protein sequences (WO 02/79415; WO 94/11028), or conjugation with other compounds (WO 96/40792).

Active evasin-4-derived sequences can be natural analogs or orthologs of evasin-4 that may be isolated from, in particular, other tick species, in particular those belonging to the Ixodidae family, and more in particular to the subfamiliy Rhipicephalinae, to which *Rhipicephalus sanguineus* belongs, as well to other subfamilies like Ixodinae (including *Ixodes scapularis* and *Ixodes ricinus*) or Amblyomminae (including *Amblyomma variegatum* and *Amblyomma americanum*). Alternatively, orthologs may be identified in mammalians, such as man and mouse.

Limited information is available on the genome and the transcriptome of haematophagous arthropods, and is mostly associated with ribosomal and mitochondrial sequences, which were studied to determine the phylogenetic relationships on the basis of their conservation (Murrell A et al., 2001). Tick genomic data are available only in partial and preliminary formats (Ullmann A J et al., 2002), but further analysis of the tick genes encoding CC-chemokine binding proteins can be performed by using genomic DNA that can be extracted from ixodid ticks by applying specific methods and conditions (Hill C A and Gutierrez, J A 2003), in particular for detecting any significant polymorphism in salivary gland proteins, as already demonstrated (Wang H et al., 1999). The genomic and protein sequences of these organisms are important for understanding their physiology and biology, therefore providing information useful for understanding the role of the proteins of the invention in host, parasite, and parasite-born pathogens relationships (Valenzuela J G, 2002b).

The biochemical and physiological characterization of the CC-chemokine binding activities described for proteins homologous to evasin-4 in the present invention can be performed by applying any of the technologies recently improved for the study of tick and tick-borne pathogens, such as two-dimensional gel electrophoresis (Madden R D et al., 2004) or RNA interference (Aljamali M N et al., 2003). Moreover, further studies can be performed to map the CC-chemokine recognition site on these proteins and the mechanisms of CC-chemokine antagonism or to identify relevant post-translational modifications.

Another aspect of the invention are fusion proteins comprising an evasin-4 polypeptide as defined above operably linked to a heterologous domain, e.g., one or more amino acid sequences which may be chosen amongst the following: an extracellular domain of a membrane-bound protein, immunoglobulin constant regions (Fc region), multimerization domains, export signals, and tag sequences (such as the ones helping the purification by affinity: HA tag, Histidine tag, GST, FLAAG peptides, or MBP).

In the context of a fusion protein, the expression "operably linked" indicates that the evasin-4 polypeptide and additional amino acid sequences are associated through peptide linkage(s), either directly or via spacer residues (e.g., a linker). In this manner, the fusion protein can be produced recombinantly, by direct expression in a host cell of a nucleic acid molecule encoding the same, as will be discussed below. Also, if needed, the additional amino acid sequences included in the fusion protein can be eliminated, either at the end of the production/purification process or in vivo, e.g., by means of an appropriate endo-/exopeptidase, as will be discussed below. The heterologous moiety may be operably linked to either the N- or the C-terminal portion of the evasin-4 polypeptide.

The design of the moieties and/or linkers, as well as methods and strategies for the construction, purification, detection, maturation, and use of fusion proteins are widely discussed in the literature (Nilsson J et al., 1997; "Applications of chimeric genes and hybrid proteins" Methods Enzymol. Vol. 326-328, Academic Press, 2000). In general, the heterologous sequences are intended to provide additional properties without impairing the therapeutic activity of the original protein (CC-chemokine binding, for example) in a significant manner. Examples of such additional properties are an easier purification procedure, a longer lasting half-life in body fluids, an additional binding moiety, the maturation by means of an endoproteolytic digestion, the stability during recombinant production, or extracellular localization. This latter feature is of particular importance for defining a specific group of fusion or chimeric proteins included in the above definition since it allows the polypeptides to be localized in the space where the isolation and purification of these polypeptides is facilitated, and where CC-chemokines are normally active.

The choice of one or more of these sequences to be fused to a evasin-4 polypeptide is dependent on the specific use and/or purification protocol of said protein as recombinant protein. For example, the activity of evasin-4 can be tested by means of a fusion protein including a histidine tag sequence facilitating both detection and purification of evasin-4. These sequences can be chosen amongst the following three basic groups of heterologous sequences.

A first group of such sequences consists of sequences helping the secretion and the purification of the protein using recombinant DNA technologies, such as a signal peptide and export signals (Rapoport T A et al., 1996), or tag sequences helping the purification by affinity (HA tag, Histidine tag, GST, FLAG, or MBP).

A second group of heterologous sequences is represented by those allowing a better stability and bioactivity of the proteins.

A typical example of a strategy allowing a prolonged half-life of a protein is the fusion with human serum albumin, or with peptides and other modified sequences (e.g. by myristoylation) that allow the binding to circulating human serum albumin (Chuang V T et al., 2002; WO 01/77137). Alternatively, the additional sequence may help the targeting to specific localization, such as in the brain (WO 03/32913).

Another way to improve the stability of a recombinant protein when administered to a subject is to generate multimers of the protein by fusing domains isolated from other proteins that allows the formation or dimers, trimers, etc. Example protein sequences allowing the multimerization of the polypeptides of the Invention are domains isolated from proteins such hCG (WO 97/30161), collagen X (WO 04/33486), C4BP (WO 04/20639), Erb proteins (WO 98/02540), or coiled coil peptides (WO 01/00814).

A well-known example of such fusion proteins is represented by the constant/Fc region of human immunoglobulin proteins, allowing the dimerization common to human immunoglobulins. Different strategies for generating fusion proteins comprising a therapeutic protein and an immunoglobulin fragment are disclosed in the literature (WO 91/08298; WO 96/08570; WO 93/22332; WO 04/085478; WO 01/03737, WO 02/66514). For example, the nucleic acid sequence encoding the mature evasin-4 can be cloned in an expression vector fused to a nucleic acid sequence encoding the original evasin-4 signal sequence (or any other appropriate signal /export sequence) at its 5' end, and the nucleic acid sequence encoding the constant region of human immunoglobulin lambda heavy chain IgG1 (NCBI Acc. No. CAA75302; segment 246-477) at its 3' end. The resulting vector can be used to transform a CHO or HEK293 host cell line and the clones stably expressing and secreting the recombinant fusion protein having evasin-4 at the N-terminus and the IgG1 sequence at the C-terminus can be selected. This clone then can be used for scaling up the production and for purifying the recombinant fusion protein from the culture medium. Alternatively, the position of the nucleic acid encoding the constant region of human immunoglobulin lambda heavy chain IgG1 and evasin-4 can be inversed, and the resulting protein can be expressed and secreted using still the original signal sequence of evasin-4, or any other appropriate signal/export sequence. Using this technology it can be also possible to generate heterodimers if two different constructs expressing one evasin-4-Fc fusion protein and the other a different Fc-based fusion protein (for example another CC-chemokine antagonist) are co-expressed in the same host cell (WO 00/18932).

A further group of heterologous sequences is represented by those adding a further functional activity that can synergise or amplify the ones shown by evasin-4. These sequences, which are expected to be either isolated from an extracellular domain of a membrane-bound protein (such as a CC-chemokine receptor) or to be present in a secreted protein, can be active as well as a CC-chemokine antagonist, and in general should have an immuno-modulatory activity.

As mentioned above, the additional sequence included in the fusion proteins may be eliminated, e.g., at the end of the production or purification process, or in vivo, if needed, e.g., by means of an appropriate endo-/exopeptidase. For example, the linker sequence included in the recombinant protein may present a recognition site for an endopeptidase (such as a caspase) that can be used to enzymatically detach the desired protein from the heterologous sequence either in vivo or in vitro. Alternatively, if the protein sequence to be expressed does not contain a starting methionine (for example, if the sequence encodes for only the mature sequence of the protein, without the signal peptide), a protein of the Invention can be expressed correctly in a host cell with a starting methionine. This additional amino acid may be then either maintained in the resulting recombinant protein, or eliminated by means of an exopeptidase, such as methionine aminopeptidase, according to methods disclosed in the literature (Van Valkenburgh H A and Kahn R A, 2002).

Further variants or analogs of the polypeptides of the invention can be obtained in the form of peptide mimetics (also called peptidomimetics), in which the nature of peptide or polypeptide has been chemically modified at the level of amino acid side chains, of amino acid chirality, and/or of the peptide backbone. These alterations are intended to provide antagonists with improved purification, potency and/or pharmacokinetics features. For example, when peptide susceptibility to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4-dinitrophenyl. Many other modifications providing increased potency, prolonged activity, ease of purification, and/or increased half-life are known in the art (WO 02/10195; Villain M et al., 2001). Preferred alternative, "synonymous" groups for amino acid derivatives included in peptide mimetics are those defined in Table II. By "amino acid derivative" is intended an amino acid or amino acid-like chemical entity other than one of the 20 genetically encoded naturally occurring amino acids. In particular, the amino acid derivative may contain substituted or non-substituted alkyl moieties that can be linear, branched, or cyclic, and may include one or more heteroatoms. The amino acid derivatives can be made de novo or obtained from commercial sources (Calbiochem-Novabiochem AG, Switzerland; Bachem, USA). The techniques for the synthesis and the development of peptide mimetics, as well as non-peptide mimetics, are well known in the art (Hruby V J and Balse P M, 2000). Various methodologies for incorporating unnatural amino acids into proteins, using both in vitro and in vivo translation systems, to probe and/or improve protein structure and function are also disclosed in the literature (Dougherty D A, 2000).

As will be discussed below, the polypeptides of the invention may be prepared by any procedure known in the art, including recombinant technologies and chemical synthesis technologies.

In a further aspect the invention resides in a nucleic acid molecule encoding a polypeptide as defined above, i.e., a polypeptide comprising the amino acid sequence of evasin-4 or of a fragment or analog thereof. Particular nucleic acid molecules of this invention are selected from the group consisting of:

a) a nucleic acid molecule encoding a protein comprising an amino acid sequence of evasin-4 identified by SEQ ID NO: 5;

b) a nucleic acid molecule encoding a protein comprising an amino acid sequence of mature evasin-4 identified by SEQ ID NO: 6;
c) a nucleic acid molecule capable of hybridization to a nucleic acid molecule of a), or b), under stringent conditions, and which encodes a protein that binds a CC-chemokine;
d) a nucleic acid molecule encoding a protein at least about 70% identical in amino acid sequence to a protein encoded by a nucleic acid molecule of a), b), or c), and that binds a CC-chemokine;
e) a nucleic acid molecule encoding a protein comprising a fragment of a protein encoded by a nucleic acid molecule of a), b), c), or d), which fragment binds a CC-chemokine; and
f) a degenerate variant of a nucleic acid molecule of a), b), c), d), or e).

In particular, the nucleic acid molecule encodes a protein selected from the group consisting of:
a) a protein having an amino acid sequence of evasin-4 identified by SEQ ID NO: 5;
b) a protein having an amino acid sequence of mature evasin-4 identified by SEQ ID NO: 6;
c) a protein comprising a fragment of a protein of a), or b), which fragment binds a CC-chemokine;
d) a protein comprising a fragment of a protein of a), or b), which fragment has an immunomodulatory activity;
e) an active mutant of a protein of a) or b), in which mutant one or more amino acid residues have been added, deleted, or substituted and which mutant binds a CC-chemokine; and
f) a fusion protein, which fusion protein comprises a protein of a), b), c), d), or e), operably linked to one or more amino acid sequences chosen amongst the following: an extracellular domain of a membrane-bound protein, an immunoglobulin constant region, a multimerization domain, a signal peptide, an export signal, and a tag sequence.

Within the context of the present invention, a "degenerate variant" designates all nucleic acid sequences that, by virtue of the degeneracy of the genetic code, code for the same amino acid sequence as a reference nucleic acid.

Furthermore, the term "nucleic acid molecule" encompasses all different types of nucleic acids, including without limitation deoxyribonucleic acids (e.g., DNA, cDNA, gDNA, synthetic DNA, etc.), ribonucleic acids (e.g., RNA, mRNA, etc.) and peptide nucleic acids (PNA). In a preferred embodiment, the nucleic acid molecule is a DNA molecule, such as a double-stranded DNA molecule, typically a cDNA.

If the main aspects are directed to the DNA and protein sequences of evasin-4 disclosed in the examples, specific embodiments include a series of evasin-4-related sequences, such as DNA or RNA sequences capable of hybridizing under moderately stringent conditions (prewashing solution of 5×SSC, 0.5% SDS, 1.0 mM EDTA (pH 8.0) and hybridization conditions of 50° C., 5×SSC, overnight) to the DNA sequences encoding evasin-4, and that code for a CC-chemokine binding protein.

For example, the Invention provides the sequence of the cDNA of *Rhipicephalus sanguineus* expressing evasin-4 (SEQ ID NO: 3), and the associated Open Reading Frame (ORF; SEQ ID NO: 4).

In other preferred embodiments the evasin-4 sequences are DNA molecules encoding proteins that are at least about 70%, preferably 80%, and most preferably 90% identical in amino acid sequence to evasin-4. This value can be calculated with any of the dedicated programs, such as FASTA (Pearson W R, 2000), and, for fragment or partial sequences, it is calculated on that portion of evasin-4 that is present in the fragment.

Another preferred embodiment is an oligonucleotide that comprises a fragment of, or that hybridizes specifically to a region of the sequence of a nucleic acid molecule as defined above. Such oligonucleotides typically contain between 5 and 100 nucleotides in length, and can be selected e.g., from the group consisting of oligonucleotides of at least about 20 nucleotides in length, oligonucleotides of at least about 30 nucleotides in length, and oligonucleotides of at least about 50 nucleotides in length. These oligonucleotides can be used for detecting (by PCR or Southern blot, for example) the non-/coding sequences in transcripts encoding evasin-4 and related sequences in a sample, or for generating and subcloning recombinant variants of evasin-4.

In a further aspect, the nucleic acid molecules defined above can be comprised in a cloning or expression vector. In this regard, a particular embodiment of this invention resides in an expression vector comprising a promoter operably associated to a nucleic acid molecule as defined above, in particular a tissue specific, constitutive promoter or regulated (e.g., inducible) promoter. The vector may comprise any additional regulatory element, such as a terminator, enhancer, origin of replication, selection marker, etc. The vector may be a plasmid, cosmid, viral vector, phage, artificial chromosome, and the like.

In a particular embodiment, this vector can comprise:
a) a DNA of the invention; and
b) an expression cassette;
wherein said DNA (a) is operably associated with a tissue specific, a constitutive, or an inducible promoter included in sequence (b).

Optionally, if the coding nucleic acid (i.e., sequence (a)) does not contain a codon for a starting methionine (for example, if this sequence encodes for only the mature sequence of the protein, without the signal peptide) the vector or expression cassette may also contain an ATG sequence that is cloned in 5' to such sequence so that it can be expressed correctly with a starting methionine. This additional amino acid may be then either maintained in the resulting recombinant protein, or eliminated by means of an enzyme, such as methionine aminopeptidase, according to methods disclosed in the literature (Van Valkenburgh H A and Kahn R A, 2002).

This vector may allow the expression of the proteins of the Invention not only in the condition of tissue culture but also in vivo, for either experimental or therapeutic reasons. For example, cells over-expressing the protein of the Invention can be transferred (e.g. encapsulated) in an animal model to check the physiological effects of the constant administration of the protein, and eventually before applying the cells to humans. Alternatively, the vector can be used for retrovirus-mediated gene transfer, or any other technology allowing the introduction and the expression of a vector or of the isolated DNA coding sequence in animal under the control of an endogenous promoter. This approach allows the generation of transgenic non-human animals in which the proteins of the Invention are expressed constitutively or in a regulated manner (e.g. in specific tissues and/or following the induction with specific compounds). Similar approaches were applied to other non-mammalian chemokine-binding protein, showing various developmental and pathological effects (Jensen K K et al., 2003).

Another aspect of the Invention are host cells transformed or transfected with a cloning or expression vector above indicated. These vectors can be used in a process of preparation of the polypeptides of the Invention. In this respect, an aspect of the Invention is a method of preparing an evasin-4 polypeptide as defined above, comprising culturing recombinant cells as defined above under conditions allowing or promoting expression and recovering the evasin-4 polypeptide. When the vector expresses the polypeptide as a protein secreted in the extracellular space, the protein can be more easily collected and purified from cultured cells in view of further processing.

Many books and reviews provide teachings on how to clone and produce recombinant proteins using vectors and Prokaryotic or Eukaryotic host cells, such as some titles in the series "A Practical Approach" published by Oxford University Press ("DNA Cloning 2: Expression Systems", 1995; "DNA Cloning 4: Mammalian Systems", 1996; "Protein Expression", 1999; "Protein Purification Techniques", 2001). In particular, the examples show how, that once the DNA sequence encoding for evasin-4 has been identified by screening the *Rhipicephalus sanguineus* cDNA library, the ORF can be adapted, modified, and inserted into expression vectors for obtaining the corresponding recombinant protein.

In general, the vectors can be episomal or non-/homologously integrating vectors, which can be introduced in the appropriate host cells by any suitable means (transformation, transfection, conjugation, protoplast fusion, electroporation, calcium phosphate-precipitation, direct microinjection, etc.) to transform them. Factors of importance in selecting a particular plasmid, viral, or retroviral vector include: the ease with which recipient cells that contain the vector, may be recognized and selected from those recipient cells which do not contain the vector; the number of copies of the vector which are desired in a particular host; and whether it is desirable to be able to "shuttle" the vector between host cells of different species. The vectors should allow the expression of the isolated proteins of the invention, or the fusion proteins comprising them in the prokaryotic or eukaryotic host cell under the control of appropriate transcriptional initiation/termination regulatory sequences, which are chosen to be constitutively active or inducible in said cell. A cell line substantially enriched in such cells can be then isolated to provide a stable cell line (as shown in the example with HEK293 and TN5 cell lines).

For eukaryotic host cells (e.g. yeasts, insect or mammalian cells), different transcriptional and translational regulatory sequences may be employed, depending on the nature of the host. They may be derived form viral sources, such as adenovirus, bovine papilloma virus, Simian virus or the like, where the regulatory signals are associated with a particular gene which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. The cells, which have been stably transformed by the introduced DNA, can be selected by also introducing one or more markers, which allow for selection of host cells, which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Host cells for recombinant production may be either prokaryotic or eukaryotic cells. Particularly suitable prokaryotic cells include bacteria (such as *Bacillus subtilis* or *E. coli*) transformed with a recombinant bacteriophage, plasmid or cosmid DNA expression vectors. Preferred are eukaryotic host cells, e.g. mammalian cells, such as human, monkey, mouse, and Chinese hamster ovary (CHO) cells, because they provide post-translational modifications to protein molecules, including correct folding or glycosylation at correct sites. Alternative eukaryotic host cells are yeast cells transformed with yeast expression vectors. Also yeast cells can carry out post-translational peptide modifications including glycosylation. A number of recombinant DNA strategies exist which utilize strong promoter sequences and high copy number of plasmids that can be utilized for production of the desired proteins in yeast. Yeast recognizes leader sequences in cloned mammalian gene products and secretes peptides bearing leader sequences (i.e., pre-peptides).

For long-term, high-yield production of a recombinant polypeptide, stable expression is preferred. For example, cell lines, which stably express the polypeptide of interest, may be transformed using expression vectors which may contain viral origins of replication and/or endogenous expression elements and a selectable marker gene on the same or on a separate vector. Following the introduction of the vector, cells may be allowed to grow for 1-2 days in an enriched media before they are switched to selective media. The purpose of the selectable marker is to confer resistance to selection, and its presence allows growth and recovery of cells that successfully express the introduced sequences. Resistant clones of stably transformed cells may be proliferated using tissue culture techniques appropriate to the cell type. A cell line substantially enriched in such cells can be then isolated to provide a stable cell line.

A particularly preferred method of high-yield production of a recombinant polypeptide of the present invention is through the use of dihydrofolate reductase (DHFR) amplification in DHFR-deficient CHO cells, by the use of successively increasing levels of methotrexate as described in U.S. Pat. No. 4,889,803. The polypeptide obtained may be in a glycosylated form.

Mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells and a number of other cell lines. In the baculovirus system, the materials for baculovirus/insect cell expression systems are commercially available in kit form from, inter alia, Invitrogen.

Alternatively, the polypeptides of this invention may be prepared by artificial synthesis. In this regard, examples of chemical synthesis technologies are solid phase synthesis and liquid phase synthesis. As a solid phase synthesis, for example, the amino acid corresponding to the carboxy-terminus of the peptide to be synthetised is bound to a support which is insoluble in organic solvents, and by alternate repetition of reactions, one wherein amino acids with their amino groups and side chain functional groups protected with appropriate protective groups are condensed one by one in order from the carboxy-terminus to the amino-terminus, and one where the amino acids bound to the resin or the protective group of the amino groups of the peptides are released, the peptide chain is thus extended in this manner. Solid phase synthesis methods are largely classified by the tBoc method and the Fmoc method, depending on the type of protective group used. Typically used protective groups include tBoc (t-butoxycarbonyl), Cl-Z (2-chlorobenzyloxycarbonyl), Br-Z (2-bromobenzyloxycarbonyl), Bzl (benzyl), Fmoc (9-fluorenylmethoxycarbonyl), Mbh (4,4'-dimethoxydibenzhydryl), Mtr (4-methoxy-2,3,6-trimethylbenzenesulphonyl), Trt (trityl), Tos (tosyl), Z (benzyloxycarbonyl) and Cl2-Bzl (2,6-dichlorobenzyl) for the amino groups; NO2 (nitro) and Pmc (2,2,5,7,8-pentamethylchromane-6-sulphonyl) for the guanidino groups); and tBu (t-butyl) for the hydroxyl groups). After synthesis of the desired polypeptide, it is subjected to the de-protection reaction and cut off from the solid support. Such peptide cutting reaction may be carried with hydrogen fluoride or trifluoromethane sulfonic acid for the Boc method, and with TFA for the Fmoc method. Totally synthetic proteins of size comparable to that of evasin-4 are disclosed in the literature (Brown A et al., 1996).

The polypeptides of the present invention can be produced, formulated, administered, or generically used in other alternative forms that can be preferred according to the desired method of use and/or production. The protein of the invention can be post-translationally modified, for example by glycosylation as shown in the examples.

In general the protein of the invention can be provided in the form of active fractions, precursors, salts, derivatives, conjugates or complexes.

As indicated above, the term "active" or "biologically active" means that such alternative compounds should maintain, or even potentiate, the CC-chemokine binding and/or immuno-modulatory properties of evasin-4.

The term "fraction" refers to any fragment of the polypeptidic chain of the compound itself, alone or in combination with related molecules or residues bound to it, for example residues of sugars or phosphates. Such molecules can result also from other modifications that do not normally alter primary sequence, for example in vitro chemical derivatization of peptides (acetylation or carboxylation), and those made by modifying the protein post-translationally, such as by phosphorylation (introduction of phosphotyrosine, phosphoserine, or phosphothreonine residues) or by glycosylation (by exposing the peptide to enzymes which affect glycosylation e.g., mammalian glycosylating or deglycosylating enzymes) during its synthesis and/or in further processing steps. In particular, evasin-4 has been characterized in tick saliva as being glycosylated. This modification may be performed in vitro, by using the appropriate modifying enzyme, or in vitro, by choosing the appropriate host cells for recombinant production.

The "precursors" are compounds which can be converted into the compounds of present invention by metabolic and enzymatic processing prior or after the administration to the cells or to the body.

The term "salts" herein refers to both salts of carboxyl groups and to acid addition salts of amino groups of the peptides, polypeptides, or analogs thereof, of the present invention. Salts of a carboxyl group may be formed by means known in the art and include inorganic salts, for example, sodium, calcium, ammonium, ferric or zinc salts, and the like, and salts with organic bases as those formed, for example, with amines, such as triethanolamine, arginine or lysine, piperidine, procaine and the like. Acid addition salts include, for example, salts with mineral acids such as, for example, hydrochloric acid or sulfuric acid, and salts with organic acids such as, for example, acetic acid or oxalic acid. Any of such salts should have substantially similar activity to the peptides and polypeptides of the invention or their analogs.

The term "derivatives" as used herein refers to derivatives that can be prepared from the functional groups present on the lateral chains of the amino acid moieties or on the amino-/or carboxy-terminal groups according to known methods. Such derivatives include for example esters or aliphatic amides of the carboxyl-groups and N-acyl derivatives of free amino groups or O-acyl derivatives of free hydroxyl-groups and are formed with acyl-groups as for example alcanoyl- or aroyl-groups.

The proteins of the Invention can be in the form of an active conjugate or complex with a molecule chosen amongst radioactive labels, biotin, fluorescent labels, cytotoxic agents, and drug delivery agents. Useful conjugates or complexes can be generated, using molecules and methods known in the art, for various reasons, for example for allowing the detection of the interaction with CC-chemokines or other proteins (radioactive or fluorescent labels, biotin), therapeutic efficacy (cytotoxic agents), or improving the agents in terms of drug delivery efficacy, such as polyethylene glycol and other natural or synthetic polymers (Harris J M and Chess R B, 2003; Pillai O and Panchagnula R, 2001). In this regard, the present invention contemplates chemically modified polypeptides and proteins as disclosed herein, in which the polypeptide or the protein is linked with a polymer. Typically, the polymer is water soluble so that the conjugate does not precipitate in an aqueous environment, such as a physiological environment. An example of a suitable polymer is one that has been modified to have a single reactive group, such as an active ester for acylation, or an aldehyde for alkylation. In this way, the degree of polymerization can be controlled. An example of a reactive aldehyde is polyethylene glycol propionaldehyde, ormono-(C1-C10) alkoxy, or aryloxy derivatives thereof (see, for example, U.S. Pat. No. 5,252,714). The polymer may be branched or un-branched. Moreover, a mixture of polymers can be used to produce the conjugates. The conjugates used for therapy can comprise pharmaceutically acceptable water-soluble polymer moieties. Suitable water-soluble polymers include polyethylene glycol (PEG), monomethoxy-PEG, mono-(C1-C10) alkoxy-PEG, aryloxy-PEG, poly-(N-vinyl pyrrolidone) PEG, tresyl monomethoxy PEG, PEG propionaldehyde, bis-succinimidyl carbonate PEG, propylene glycol homopolymers, a polypropyleneoxide/ethylene oxide co-polymer, polyoxyethylated polyols (e.g., glycerol), polyvinyl alcohol, dextran, cellulose, or other carbohydrate-based polymers. Suitable PEG may have a molecular weight from about 600 to about 60,000, including, for example, 5,000, 12,000, 20,000 and 25,000. A conjugate can also comprise a mixture of such water-soluble polymers. As an illustration, the evasin-4 polypeptide or variant of the present invention can be modified with PEG, a process known as "PEGylation." PEGylation can be carried out by any of the PEGylation reactions known in the art (see, for example, EP 0 154 316). For example, PEGylation can be performed by an acylation reaction or by an alkylation reaction with a reactive polyethylene glycol molecule. In an alternative approach, conjugates are formed by condensing activated PEG, in which a terminal hydroxy or amino group of PEG has been replaced by an activated linker (see, for example, U.S. Pat. No. 5,382,657). The PEG may be linear or branched. It stabilizes the protein, may increase the half-life and improve the bioactivity.

These evasin-4-derived compounds may be produced following site-directed modification of an appropriate residue, in an internal or terminal position. Residues can be used for attachment, provided they have a side-chain amenable for polymer attachment (i.e., the side chain of an amino acid bearing a functional group, e.g., lysine, aspartic acid, glutamic acid, cysteine, histidine, etc.). Alternatively, a residue at these sites can be replaced with a different amino acid having a side chain amenable for polymer attachment.

For example, an additional cysteine allowing direct PEGylation can be added at the N- or C-terminus of the mature protein sequence by recombinant DNA technologies or enzymatically. Alternatively, the cysteine may be included in the protein by the substitution of a residue, for example in correspondence of a glycosylation site.

In another aspect the present invention relates to antibodies that selectively bind the proteins of the invention.

The term "antibody" as used herein encompasses monoclonal and polyclonal antibodies, chimeric, humanized, fully human, bispecific or multispecific antibodies as well as fragments thereof such as single chain antibodies (scFv) or domain antibodies, as further explained below.

Within the context of this invention, the term "selective" binding indicates that the antibodies preferentially bind the target polypeptide or epitope, i.e., with a higher affinity than any binding to any other antigen or epitope. In other words, binding to the target polypeptide can be discriminated from non-specific binding to other antigens. It is preferred that the antibodies according to the present invention exhibit binding affinity (Ka) to the target polypeptide or epitope of $10^6$ M$^{-1}$ or greater, preferably $10^7$ M$^{-1}$ or greater, more preferably $10^8$ M$^{-1}$ or greater and most preferably $10^9$ M$^{-1}$ or greater. The binding affinity of an antibody can be readily determined by one of ordinary skill in the art, for example, by Scatchard analysis (Scatchard G., 1949).

Antibodies of this invention may be monoclonal or polyclonal antibodies, or fragments or derivative thereof having substantially the same antigen specificity.

Methods of preparing polyclonal antibodies from various species, including rodents, primates and horses, have been described for instance in Vaitukaitis et al (1971). Polyclonal antibodies can be raised in a mammal, for example, by one or more injections of an immunizing agent and, if desired, an adjuvant. Typically, the immunizing agent and/or adjuvant will be injected in the mammal by multiple subcutaneous or intraperitoneal injections. The immunizing agent may include the polypeptide of SEQ ID NO 5, 6 or a variant as described hereabove or a fusion protein thereof. It may be useful to conjugate the immunizing agent to a protein known to be immunogenic in the mammal being immunized. Examples of such immunogenic proteins include but are not limited to keyhole limpet hemocyanin, serum albumin, bovine thyroglobulin, and soybean trypsin inhibitor. Examples of adjuvants which may be employed include Freund's complete adjuvant and MPL-TDM adjuvant (monophosphoryl Lipid A, synthetic trehalose dicorynomycolate). Repeated injections may be performed. Blood samples are collected and immunoglobulins or serum are separated.

The antibodies may, alternatively, be monoclonal antibodies. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. The modifier "monoclonal" indicates the character of the antibody as being obtained from a substantially homogeneous population of antibodies, and is not to be construed as requiring production of the antibody by any particular method.

Methods of producing monoclonal antibodies may be found, for instance, in Kohler et al (Nature 256 (1975) 495), incorporated therein by reference.

In a hybridoma method, a mouse, hamster, or other appropriate host animal, is typically immunized with an immunizing agent (the immunizing agent will typically include the polypeptide of SEQ ID NO: 5, 6, or a variant as described hereabove or a fusion protein thereof) to elicit lymphocytes that produce or are capable of producing antibodies that will specifically bind to the immunizing agent. Alternatively, the lymphocytes may be immunized in vitro. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding 1986). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells. Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies.

The culture medium in which the hybridoma cells are cultured can then be assayed for the presence of monoclonal antibodies directed against the immunizing peptide. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art.

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640 medium. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies may also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA may be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells.

The "monoclonal antibodies" may also be isolated from phage antibody libraries using the techniques described in Clackson et al., 1991.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain cross-linking. Alternatively, the relevant cysteine residues are substituted with another amino acid residue or are deleted so as to prevent cross-linking.

In vitro methods are also suitable for preparing monovalent antibodies. Digestion of antibodies to produce fragments thereof, particularly, Fab fragments, can be accomplished using routine techniques known in the art.

Antibodies may also be produced by selection of combinatorial libraries of immunoglobulins, as disclosed for instance in Ward et al (1989).

The antibodies of the invention may further comprise humanized antibodies or human antibodies. Humanized forms of non-human (e.g., murine) antibodies are chimeric immunoglobulins, immunoglobulin chains or fragments thereof (such as Fv, Fab, Fab', F(ab')2 or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of non-human species (donor antibody) such as mouse, rat or rabbit having the desired specificity, affinity and capacity. In some instances, Fv framework residues of the human immunoglobulin are replaced by corresponding non-human residues.

Methods for humanizing non-human antibodies are well known in the art. Humanization can be essentially performed following the method of Winter and coworkers (Jones et al., Nature, 321:522-525 (1986)), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species.

Human antibodies can also be produced using various techniques known in the art, including phage display libraries (Hoogenboom and Winter, (1991). Similarly, human antibodies can be made by the introducing of human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016

The invention also pertains to immunoconjugates comprising an antibody conjugated to heterologous moieties, such as cytotoxic agents, labels, drugs or other therapeutic agents, covalently bound or not, either directly or through the use of coupling agents or linkers. Cytotoxic agent include chemotherapeutic agent, toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re.

In another embodiment, the antibody may be conjugated to a "receptor" (such as streptavidin) for utilization in tumor pretargeting wherein the antibody-receptor conjugate is administered to the patient, followed by removal of unbound conjugate from the circulation using a clearing agent and then administration of a "ligand" (e.g., avidin) that is conjugated to a cytotoxic agent (e.g., a radionucleotide).

Moreover, antibodies or antibody fragments of the present invention can be PEGylated using methods in the art and described herein. The antibodies disclosed herein may also be formulated as immunoliposomes. Liposomes with enhanced circulation time are disclosed in U.S. Pat. No. 5,013,556.

The invention also pertains to "Antibody fragments" which comprise a portion of an intact antibody, preferably the antigen binding or variable region of the intact antibody. Examples of antibody fragments include Fab, Fab', F(ab')2, and Fv fragments; diabodies; linear antibodies; single-chain antibody molecules; monobodies; diabodies; camelized monobodies; domain antibodies and multispecific antibodies formed from antibody fragments.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the VH-VL dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab fragments differ from Fab' fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments which have hinge cysteines between them. Other chemical couplings of antibody fragments are also known. The "light chains" of antibodies (immunoglobulins) from any vertebrate species can be assigned to one of two clearly distinct types, called kappa and lambda, based on the amino acid sequences of their constant domains.

"Single-chain antibody molecules" are fragments of an antibody comprising the VH and VL domains of said antibody, wherein these domains are present in a single polypeptide chain. Preferably, the Fv polypeptide further comprises a polypeptide linker between the VH and VL domains which enables the single-chain antibody molecule to form the desired structure for antigen binding.

The term "diabodies" refers to small antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161.

The term "monobody" as used herein, refers to an antigen binding molecule with a heavy chain variable domain and no light chain variable domain. A monobody can bind to an antigen in the absence of light chains and typically has three CDR regions designated CDRH1, CDRH2 and CDRH3. A heavy chain IgG monobody has two heavy chain antigen binding molecules connected by a disulfide bond. The heavy chain variable domain comprises one or more CDR regions, preferably a CDRH3 region.

A "camelized monobody" refers to a monobody or antigen binding portion thereof obtained from a source animal of the camelid family, including animals with feet with two toes and leathery soles. Animals in the camelid family include camels, llamas, and alpacas. It has been reported that camels (*Camelus dromedaries* and *Camelus bactrianus*) often lack variable light chain domains when IgG-like material from their serum is analyzed, suggesting that sufficient antibody specificity and affinity can be derived from VH domains (three CDR loops) alone.

Also included into the invention are single domain antibodies. Single domain antibodies, also called domain antibodies or dAbs, are the smallest functional binding units of antibodies, corresponding to the variable regions of either the heavy (VH) or light (VL) chains of human antibodies. Domain antibodies have a molecular weight of approximately 13 kDa, or less than one-tenth the size of a full antibody. In contrast to conventional antibodies, domain antibodies are well expressed in bacterial, yeast, and mammalian cell systems. In addition, many domain antibodies are highly stable and retain activity even after being subjected to harsh conditions, such as freeze-drying or heat denaturation which makes them amenable to a wide range of pharmaceutical formulation conditions and manufacture processes.

The proteins of the invention can be provided in more or less purified forms.

In particular, purification of the natural, synthetic or recombinant antagonists of the invention can be carried out by any one of the methods known for this purpose, i.e. any conventional procedure involving extraction, precipitation, chromatography, electrophoresis, or the like. A further purification procedure that may be used in preference for purifying the protein of the invention is affinity chromatography using monoclonal antibodies or affinity groups, which bind the target protein and which are produced and immobilized on a gel matrix contained within a column. Impure preparations containing the proteins are passed through the column. The protein will be bound to the column by heparin or by the specific antibody while the impurities will pass through. After washing, the protein is eluted from the gel by a change in pH or ionic strength. Alternatively, HPLC (high performance liquid chromatography) can be used. The elution can be carried using a water-acetonitrile-based solvent commonly employed for protein purification. Purified preparations of the proteins of the Invention, as used herein, refers to the preparations which are at least 1% (by dry weight), and preferably at least 5%, of said proteins.

Another aspect of the present invention is a pharmaceutical composition comprising an evasin-4 polypeptide as defined above (in the form of proteins and their alternative forms described above) as active ingredient, and a suitable diluent or carrier.

Another aspect of the present invention is a pharmaceutical composition comprising a nucleic acid molecule encoding an evasin-4 polypeptide as defined above, or a corresponding vector or recombinant host cell, and a suitable diluent or carrier.

A further aspect of this invention relates to the use of an evasin-4 polypeptide as defined above, or a nucleic acid encoding the same, for the manufacture of a medicament for use in regulating an immune response in a subject.

These compositions can be used as medicaments, in particular, for regulating an immune or inflammatory response in a mammal, and more particularly as anti-inflammatory compounds.

In general, given the involvement of CC-chemokines in many human and veterinary disorders, the CC-chemokine binding proteins of the invention can be used as antagonists of CC-chemokines for the treatment or prevention of CC-chemokine-related disorders in animals. A non-exhaustive list of CC-chemokine-related disorders includes: inflammatory diseases, autoimmune diseases, immune diseases, infections, allergic diseases, cardiovascular diseases, metabolic diseases, gastrointestinal diseases, neurological diseases, sepsis, diseases related to transplant rejection, or fibrotic diseases. Non-limiting examples of these diseases are the following: arthritis, rheumatoid arthritis (RA), psoriatic arthritis, psoriasis, rheumatoid arthritis, restenosis, sepsis, osteoarthritis, systemic lupus erythematosus (SLE), systemic sclerosis, scleroderma, polymyositis, glomerulonephritis, fibrosis, allergic or hypersensitivity diseases, dermatitis, asthma, chronic obstructive pulmonary disease (COPD), inflammatory bowel disease (IBD), Crohn's disease, fibromas, ulcerative colitis, multiple sclerosis, septic shock, viral infection, cancer, endometriosis, transplantation, graft-versus-host disease (GVHD) cardiac and renal reperfusion injury, and atherosclerosis.

The proteins of the invention, or specific fragments, can be used as active ingredients in the manufacture of pharmaceutical compositions for regulating an immune or inflammatory response in a mammal, for example of anti-inflammatory compositions. Alternatively, the proteins of the invention, or specific fragments, can be used as active ingredients in the manufacture of pharmaceutical compositions for the vaccination of a mammal against parasites, virus, or bacteria. The process for the preparation of such pharmaceutical compositions comprises combining evasin-4 together with a pharmaceutically acceptable diluent or carrier.

A pharmaceutical composition containing a protein of the invention as active ingredient can be used for binding a CC-chemokine in vivo, blocking the binding of a CC-chemokine to a corresponding cell surface receptor and consequently producing a potentially therapeutic effect, such as an anti-inflammatory effect. A pharmaceutical composition containing a protein of the invention as active ingredient, can be used also for binding to CC-chemokine analogues present in viruses, bacteria, or parasites to block entry of said virus, bacteria, or parasite into cells. Pharmaceutical compositions for vaccination of a mammal against a parasite, a virus or a bacteria, can comprise a fragment of the protein of the invention as active ingredient. The compositions above indicated can further comprise an additional immunosuppressant or anti-inflammatory substance.

The pharmaceutical compositions may contain, in combination with the proteins of the invention as active ingredient, suitable pharmaceutically acceptable diluents, carriers, biologically compatible vehicles and additives which are suitable for administration to an animal (for example, physiological saline solution) and eventually comprising auxiliaries (like excipients, stabilizers, or adjuvants) which facilitate the processing of the active compounds into preparations which can be used pharmaceutically. The pharmaceutical compositions may be formulated in any acceptable way to meet the needs of the mode of administration. For example, the use of biomaterials and other polymers for drug delivery, as well the different techniques and models to validate a specific mode of administration, are disclosed in literature (Luo B and Prestwich G D, 2001).

"Pharmaceutically acceptable" is meant to encompass any carrier, which does not interfere with the effectiveness of the biological activity of the active ingredient and that is not toxic to the host to which is administered. For example, for parenteral administration, the above active ingredients may be formulated in unit dosage form for injection in vehicles such as saline, dextrose solution, serum albumin and Ringer's solution. Carriers can be selected also from starch, cellulose, talc, glucose, lactose, sucrose, gelatin, malt, rice, flour, chalk, silica gel, magnesium stearate, sodium stearate, glycerol monostearate, sodium chloride, dried skim milk, glycerol, propylene glycol, water, ethanol, and the various oils, including those of petroleum, animal, vegetable or synthetic origin (peanut oil, soybean oil, mineral oil, sesame oil).

Any accepted mode of administration can be used and determined by those skilled in the art to establish the desired blood levels of the active ingredients. For example, administration may be by various parenteral routes such as subcutaneous, intravenous, intradermal, intramuscular, intraperitoneal, intranasal, transdermal, rectal, oral, or buccal routes. The pharmaceutical compositions of the present invention can also be administered in sustained or controlled release dosage forms, including depot injections, osmotic pumps, and the like, for the prolonged administration of the polypeptide at a predetermined rate, preferably in unit dosage forms suitable for single administration of precise dosages.

Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyl oleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99.99 percent, preferably from about 20 to 75 percent of active compound together with the excipient.

It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredient is comprised between 0.01 to 100 milligrams per kilogram of body weight per day. Ordinarily 1 to 40 milligrams per kilogram per day given in divided doses or in sustained release form is effective to obtain the desired results. Second or subsequent administrations can be performed at a dosage, which is the same, less than, or greater than the initial or previous dose administered to the individual.

Another aspect of the invention is the use of a protein encoded by a DNA of the Invention as a medicament, in particular in the preparation of a composition for regulating an immune or inflammatory response in a mammal.

Further aspects of the Invention are methods for immunising an animal against a blood-feeding ectoparasite, or for regulating an immune or inflammatory response in an animal in need thereof, comprising administering to said animal with a protein of the Invention said animal for a time and under conditions sufficient to regulate said immune response.

Another aspect of the invention is a method for treating or preventing CC-chemokine-related diseases comprising the administration of an effective amount of the compounds of the present invention.

An "effective amount" refers to an amount of the active ingredients that is sufficient to affect the course and the severity of the disease, leading to the reduction or remission of such pathology. The effective amount will depend on the route of administration and the condition of the patient.

The wording "CC-chemokine-related diseases" indicates any disease due to an excessive or uncontrolled CC-chemokine production, leading to a massive monocyte/macrophage/neutrophil/T-cell/eosinophil infiltration, and wherein the administration of evasin-4 may provide a beneficial effect. A non-exhaustive list of such chronic, acute, or inherited diseases is provided above.

The therapeutic applications of the CC-chemokine antagonists of the invention and of the related reagents can be evaluated (in terms or safety, pharmacokinetics and efficacy) by the means of in vivo or in vitro assays making use of mammalian cells, tissues and models. A non-exhaustive list of assays includes: calcium mobilisation, degranulation, upregulation of pro-inflammatory cytokines, upregulation of proteases, inhibition of cellular recruitment in vitro and in vivo.

Further aspects of the invention are test kits containing any of the compound disclosed in association to the CC-chemokine binding proteins of the invention. For example, a kit for detecting a CC-chemokine or an analogue, a CC-chemokine binding protein or a receptor, the interaction of CC-chemokine and a CC-chemokine binding protein, or antagonists or agonists of said interaction, comprising a detecting reagent and at least a compound selected from the group consisting of:

a) A nucleic acid molecule (e.g., a DNA);

b) An oligonucleotide;

c) A protein; and d) An antibody;

derived from the CC-chemokine binding protein of the Invention.

These kits can be used in methods applicable in vitro or in vivo in which a sample is contacted by one of these compounds, which can be labeled or immobilized on a solid support.

The present invention has been described with reference to the specific embodiments, but the content of the description comprises all modifications and substitutions, which can be brought by a person skilled in the art without extending beyond the meaning and purpose of the claims.

The invention will now be described by means of the following Examples, which should not be construed as in any way limiting the present invention. The Examples will refer to the Figures specified here below.

EXAMPLES

Example 1

Screening of the *Rhipicephalus sanguineus* cDNA Library for CC-Chemokine Binding Activities and Cloning of Evasin-4

Materials and Methods a. Construction of the *Rhipicephalus sanguineus* cDNA Library and of the Control Plasmid Expressing Evasin-3

Salivary glands were harvested from 100 adult ticks (*Rhipicephalus sanguineus*) and were immediately stored in ice-cold RNAlater™ solution (Ambion) until further use. Total RNA was extracted using the TRIzol™ method (Invitrogen) according to the manufacturer's instructions. The cDNA library was constructed in the phagemid vector λTriplEX2 using the SMART cDNA library construction kit (Clontech). The cDNAs were size-fractionated with a ChromaSpin 400 column (Clontech) according to the manufacturer's instructions before ligation to the vector. The size of the cloned cDNA inserts in the library ranged from about 0.6 kb to 1.5 kb and the frequency of inserts was approximately 80%.

The cDNA inserts from the *Rhipicephalus sanguineus* salivary gland cDNA library in pTriplEX2 were excised with restriction enzyme Sfi I, and subcloned into the Sfi I site of the mammalian cell expression vector pEXP-lib (Clontech). The pEXP-Lib vector contains an expression cassette comprising the human cytomegalovirus (CMV) major immediate early promoter/enhancer followed by a multiple cloning site; an internal ribosome entry site (IRES) of the encephalomyocarditis virus (ECMV); a gene encoding puromycin resistance (puromycin-N-acetyl-transferase); and the polyadenylation signal of the bovine growth hormone. The multiple cloning site contains two distinct Sfi I sites (Sfi IA and Sfi IB, that differ in their interpalindromic sequences), which allows the directional subcloning of cDNA inserts from the pTriplEX2 vector to pEXPII.

The control protein evasin-3 (SEQ ID NO: 1) was expressed by cloning the cDNA encoding the protein (SEQ ID NO: 2) into pEXP-lib as described above to generate pEXP-lib evasin-3.

b. cDNA Library Screening

Human embryonic kidney 293 cells (HEK293 cells; ATCC Cat. No. CRC-1573) were maintained in DMEM-F12 Nut Mix, 10% heat-inactivated fetal calf serum, 2 mM L-Glutamine, 100 units/ml penicillin-streptomycin solution (Invitrogen). Cells were plated in 96 well format cell culture plates at approximately 50% confluence 24 hours before transfection.

The *Rhipicephalus sanguineus* salivary gland cDNA library in pEXP lib was fractionated into 100 pools containing approx 270 cDNA clones. Plasmid mini prep DNA was isolated from small scale cultures (5 ml) of the pools, and transfected into HEK293 cells using a GenePorter2 transfection kit (Gene Therapy Systems) according to the manufacturer's protocol. The pEXP-lib plasmid containing the cDNA encoding evasin-3 was transfected into HEK293 in the same manner.

Culture medium from transfected HEK293 cells was harvested three days after the transfection. The conditioned medium was centrifuged to remove cell debris, and the supernatant tested in a cross-linking assay.

For cross-linking experiments, 20 μl of conditioned media samples were transferred to a 96-well plate (Costar). Radio-labeled CC-chemokines either $^{125}$I-CCL5/RANTES or $^{125}$I-CCL11/eotaxin were added to a final concentration of 0.23 nM to each well and incubated with shaking for 1 hour at room temperature. $^{125}$I-CXCL8/IL-8 was added to duplicate 20 μl aliquots of the sample containing the positive control (evasin-3). 3 μl of BS3 cross-linking reagent (25 mM) were added to each sample but to only one duplicate of the evasin-3 supernatant, and further incubated for 1 hour with shaking. After this time 5 μl of 10× sample buffer (125 mM Tris base, pH 6.8, containing 10% SDS, 5 mM EDTA, 20% glycerol, 0.2% w/w bromophenol blue, 1 M DTT) were added to each well to stop the cross-linking reaction. The samples were then boiled for 5 minutes and electrophoresed on a 10% Bis-Tris SDS-polyacrylamide gel (Invitrogen NuPAGE, catalog no. NP0301BOX). After electrophoresis the gel was sealed in Saran Wrap™ and directly exposed to a K-type storage phospho-imaging screen (Biorad) for 3 to 16 hours. Imaging screens were scanned at a resolution of 100 μm using a Biorad Personal FX phosphoimager.

Results

The saliva of the tick *Rhipicephalus sanguineus* has been shown to contain immuno-modulating activities, such as suppression of immunoglobulin and cytokine production (Matsumoto K et al., 2003) or T cell proliferation (Ferreira B R and Silva J S, 1998), but not activities directed specifically to CC- or CXC-chemokines. However chemokine binding activity has been detected in the saliva of other tick species (Hajnicka et al., 2005)

In order to identify the CC-chemokine binding activity in *Rhipicephalus sanguineus* at the cDNA/protein sequence level a cDNA library was generated from *Rhipicephalus sanguineus* salivary glands. Pools of cDNAs from this library were used to transfect HEK293 cells In this system, cDNAs which encode secreted proteins, are expressed by the HEK293 cells and secreted into the culture medium. The supernatants can be tested directly, in a cross-linking assay for binding to a radio-labeled CC-chemokine ($^{125}$I-CCL5/RANTES or $^{125}$I-CCL11/eotaxin). The addition of the cross-linking reagent to the radio-labeled CC-chemokine/CC-chemokine binding protein stabilizes the protein complex by linking the two molecules covalently. The resulting complex can be identified as a band shift from the molecular weight of the native chemokine to the molecular weight of the complex visualized by SDS-polyacrylamide gel electrophoresis (SDS-PAGE) and subsequent autoradiography. This cross-linking method is highly sensitive as nanogram amounts of protein can be detected (FIG. 2).

As a positive control, conditioned medium from HEK cells transfected with evasin-3 which is known to bind specifically to CXCL8, was tested in parallel. As a negative control, conditioned medium from mock transfected HEK 293 cells was used. cDNA pools which gave rise to a positive signal in the cross-linking assay were subjected to successive rounds of screening and deconvolution until a single transfected cDNA responsible for the CC-chemokine binding activity could be identified. The resultant cDNA was called evasin-4 (FIG. 1).

The full-length cDNA of evasin-4 (SEQ ID NO: 3, FIG. 1) contains an open reading frame (ORF; SEQ ID NO: 4) encoding a protein of 127 amino acids (SEQ ID NO: 5). The protein sequence is predicted to contain a signal peptide sequence (amino acids 1-17), which when cleaved, generates a mature protein of 110 amino acids (SEQ ID NO: 6). Evasin-4 has no significant homology to any other known protein. Further features of evasin-4 are 7 potential N-linked glycosylation sites and 9 cysteine residues.

Example 2

Purification of a Truncated, 6HIS Tagged Version of Evasin-4 (Δ6 Evasin-4) from the Culture Supernatants of Transfected HEK293 EBNA Cells Materials and Methods a. Subcloning of Δ6 Evasin-4 cDNA with a 6 Histidine (6His) Tag at the N Terminus into Expression Vectors pDEST8 and pEAK12d using the Gateway™ Cloning Process The full length amino acid sequence of evasin-4 contains a predicted 17 amino acid signal peptide which is theoretically cleaved to produce a mature protein of 110 amino acids. In order to produce recombinant evasin-4 for biochemical characterization, a cDNA construct was generated by a series of PCR reactions in which the signal peptide of uPA (SEQ ID NO: 7) was fused to a five amino acid flexible linker sequence (GSPNS) followed by a 6 histidine tag sequence, separated from the sequence encoding amino acids 24-127 of full length evasin-4 by a second flexible linker (GSPNS) and caspase 8 cleavage site (LETD). The signal peptide of UPA flanked at the 3' end by the sequence encoding the 5 amino acid linker sequence and first 3 histidines of the 6 HIS tag was generated in a PCR reaction (PCR1) containing 2 µl (50 ng) of plasmid pEAK12d-PAC_upa-SP-hIL18BP-6His (FIG. 4), 3 µl dNTPs (5 mM), 10 µl of 10× Pfx polymerase buffer, 1 µl MgSO$_4$ (50 mM), 1.5 µl each of gene specific primer (10 µM) spUPA PCR1F (SEQ ID NO:12) and spUPA-GSPNS R (SEQ ID NO: 13), and 0.5 µl Platinum Pfx DNA polymerase (Invitrogen) in a final volume of 50 µl. The amplification conditions were an initial denaturing step of 94° C. for 4 min; 9 cycles of 94° C. for 30 seconds, 48° C. for 30 seconds and 68° C. for 1 min; 20 cycles of 94° C. for 30 seconds, 52° C. for 30 seconds, and 68° C. for 1 min; a cycle at 68° C. for 10 min and a holding cycle at 4° C. The resultant PCR products were visualized on a 1.5% agarose gel in 1×TAE buffer (Invitrogen) and amplification products were purified using the QIAquick PCR Purification Kit (QIAGEN). The PCR product (product 1, SEQ ID NO: 8) was eluted in 30 µl EB Buffer (10 mM Tris-HCl, pH 8.5)

In PCR 2, the mature evasin-4 coding sequence (encoding amino acids 24-127) flanked at the 5' end by the linker sequence SPNS and caspase 8 cleavage site sequence LETD was generated in a 50 ul PCR reaction mix containing 2 µl pEXP-Lib-Evasin-4 (FIG. 5) (50 ng), 3 µl dNTPs (5 mM), 10 µl of 10× Pfx polymerase buffer, 1 µl MgSO$_4$ (50 mM), 1.5 µl each of gene specific primer (10 µM) SPNS-LEDT-Evasin-4F (SEQ ID NO: 14) and Evasin-4 PCR1R (SEQ ID NO: 15), and 0.5 µl Platinum Pfx DNA polymerase (Invitrogen). The amplification conditions were the same as described for PCR 1. The resultant PCR product (Product 2, SEQ ID NO: 9) was visualized on a 1.5% agarose gel in 1×TAE buffer (Invitrogen) and amplification products were purified using the QIAquick PCR Purification Kit (QIAGEN) eluted with 50 µl EB buffer according to the manufacturer's instructions.

In PCR 3, a 5' 6HIS tag sequence was added to the 5' end of PCR product 2 to generate a cDNA encoding evasin-4 (amino acids 24-127) flanked at the 5' end by a 6HIS tag sequence fused to a 5 amino acid linker and caspase 8 cleavage site sequence. The reaction mixture, in a final volume of 50 µl contained 10 µl of product 2, 3 µl dNTPs (5 mM), 10 µl of 10× Pfx polymerase buffer, 1 µl MgSO$_4$ (50 mM), 1.5 µl each of gene specific primer (10 µM) 6H-GSPNS-Evasin-4F (SEQ ID NO: 16) and Evasin-4 PCR1R (SEQ ID NO: 15), and 0.5 µl Platinum Pfx DNA polymerase (Invitrogen). PCR3 amplification conditions were an initial denaturing step of 94° C. for 4 min; 9 cycles of 94° C. for 30 seconds, 48° C. for 30 seconds and 68° C. for 1 min; 20 cycles of 94° C. for 30 seconds, 52° C. for 30 seconds, and 68° C. for 1 min; a cycle at 68° C. for 10 min and a holding cycle at 4° C. The resultant PCR product (product 3, SEQ ID NO: 10) was visualized on a 1.5% agarose gel in 1×TAE buffer (Invitrogen), was purified using the QIAquick PCR Purification Kit (QIAGEN) as described above and was eluted in 30 µl EB Buffer (10 mM Tris-HCl, pH 8.5).

In PCR 4, the PCR products from PCR1 and PCR 3 were annealed and amplified to generate evasin-4 (amino acids 24-127) coding sequence flanked at the 5' the Gateway attB1 sequence, in frame uPA signal peptide, linker, 6HIS tag, linker and caspase 8 cleavage site and flanked at the 3' end by a stop codon and Gateway attB2 sequence (FIG. 3). The reaction mixture (in a final volume of 50 µl) contained 9 µl of PCR product 1, 3 µl of PCR product 3, 3 µl dNTPs (5 mM), 10 µl of 10× Pfx polymerase buffer, 1 µl MgSO$_4$ (50 mM), 1.5 µl of each Gateway conversion primer (10 µM) evasin-4 PCR2F (SEQ ID NO: 17) and evasin-4 PCR2R (SEQ ID NO: 18) and 0.5 µl of Platinum Pfx DNA polymerase. The conditions for PCR4 reaction were: 94° C. for 4 min; 9 cycles of 94° C. for 30 seconds, 48° C. for 30 seconds and 68° C. for 1 min; 20 cycles of 94° C. for 30 seconds, 52° C. for 30 seconds, and 68° C. for 1 min, a cycle at 68° C. for 10 min and a holding cycle at 4° C. The resultant PCR product (PCR product 4, SEQ ID NO: 11) was visualized on a 1.5% agarose gel in 1×TAE buffer (Invitrogen) and a band migrating at the predicted molecular mass was purified from the gel using the QIAquick Gel Extraction Kit (QIAGEN) and eluted in 50 µl EB Buffer according to the manufacturer's instructions.

The second stage of the Gateway cloning process involves subcloning of the Gateway modified PCR product into the Gateway entry vector pDONR221. Five ill of purified PCR product 4 were incubated with 1.5 µl pDONR221 vector (0.1 µg/µl), 2 µl BP buffer and 1.5 µl of BP clonase enzyme mix (Invitrogen) in a final volume of 10 µl at room temperature for 1 hour. The reaction was stopped by addition of proteinase K 1 µl (2 µg/µl) and incubated at 37° C. for a further 10 min. An aliquot of this reaction (1 µl) was used to transform *E. coli* DH10B cells by electroporation as follows: a 20 µl aliquot of DH10B electrocompetent cells (Invitrogen) was thawed on ice and 1 µl of the BP reaction mix was added. The mixture was transferred to a chilled 0.1 cm electroporation cuvette and the cells electroporated using a BioRad Gene-Pulser™ according to the manufacturer's protocol. SOC medium (1 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 µl and 100 µl) were then plated on L-broth (LB) plates containing kanamycin (40 µg/ml) and incubated overnight at 37° C.

Plasmid mini-prep DNA was prepared from 5 ml cultures from 6 of the resultant kanamycin resistant colonies using a Qiaprep Turbo 9600 robotic system (Qiagen). Plasmid DNA (200-500 ng) was subjected to DNA sequencing with 21M13 and M13Rev primers (SEQ ID NO: 19, SEQ ID NO: 20) using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 DNA sequencer.

Plasmid eluate (1.5 µl or approx. 100 ng) from one of the clones, which contained the correct sequence (pDONR221-spUPA-6H-Evasin-4, FIG. 6) was then used in a recombination reaction containing either 1.5 µl of pDEST8 vector or 1.5 µl of pEAK12d vector (0.1 µg/µl), 2 µl LR buffer and 1.5 µl of LR clonase (Invitrogen) in a final volume of 10 µl. The mixtures were incubated at room temperature for 1 hour. The reactions were stopped by addition of Proteinase K (2 µg) and incubated at 37° C. for a further 10 minutes. An aliquot of each reaction (1 µl) was used to transform *E. coli* DH10B cells by electroporation as follows: a 20 µl aliquot of DH10B electrocompetent cells (Invitrogen) was thawed on ice and 1 µl of the LR reaction mix was added. The mixture was transferred to a chilled 0.1 cm electroporation cuvette and the cells electroporated using a BioRad Gene-Pulser™ according to the manufacturer's recommended protocol. SOC media (1 ml), which had been pre-warmed to room temperature, was added immediately after electroporation. The mixture was transferred to a 15 ml snap-cap tube and incubated, with shaking (220 rpm) for 1 hour at 37° C. Aliquots of the transformation mixture (10 µl and 100 µl) were then plated on L-broth (LB) plates containing ampicillin (100 µg/ml) and incubated overnight at 37° C.

Three colonies from each transformation were suspended in 50 µl sterile water. A 25 µl aliquot was then subjected to PCR amplification in a 50 µl reaction mixture containing 2 µl dNTPs (5 mM), 5 µl of 10× AmpliTaq polymerase buffer containing 15 mM MgSO$_4$, 2.5 µl each of vector specific primer (10 µM) pEAK12F (SEQ ID NO: 21 and pEAK12R (SEQ ID NO: 22) for the pEAK12d vector and pDEST8F (SEQ ID NO: 23) and pDEST8R (SEQ ID NO: 24) for the pDEST8 vector), and 0.5 µl AmpliTaq DNA polymerase (Invitrogen). The PCR reaction was performed using an initial denaturing step of 96° C. for 2 min; 35 cycles of 94° C. for 30 seconds, 55° C. for 30 seconds and 72° C. for 30 second. The resultant PCR product was visualized on a 1.5% agarose gel in 1×TAE buffer (Invitrogen) and one colony containing the correct insert size for each construct was chosen for DNA purification. Plasmid mini-prep DNA was prepared from 5 ml overnight cultures inoculated with 5 µl of the suspended colony Qiaprep Bio Robot 8000 (Qiagen). Plasmid DNA (200-500 ng) in pEAK12d vector (FIG. 7) was subjected to DNA sequencing with pEAK12F (SEQ ID NO: 21) and pEAK12R primers (SEQ ID NO:22). Plasmid DNA (200-500 ng) in the pDEST8 vector (FIG. 8) was subjected to DNA sequencing with pDEST8F (SEQ ID NO: 23) and pDEST8R primers (SEQ ID NO: 24) as described above.

Plasmid maxi-prep DNA was prepared from a 500 ml culture of a sequence verified pEAK12d_Evasin-4-HIS clone using Qiagen Plasmid MEGA Kit (QIAGEN) according to the manufacturer's instructions. Plasmid DNA was resuspended at a concentration of 1 µg/µl in sterile water (or 10 mM Tris-HCl pH 8.5) and stored at −20° C. Plasmid mini-prep DNA was prepared from a 5 ml culture of a sequence verified pDEST8-Evasin-4-HIS clone using a Qiaprep Turbo 9600 robotic system (Qiagen) as described above.

c. Purification of Recombinant Δ6 Evasin-4 Expressed in HEK293 Cells

Cell culture supernatant (500 ml) from HEK293-EBNA cells was harvested 6 days after transfection with pEAK12d-spUPA-6His-Evasin-4 (FIG. 7) and diluted with 2 volumes of 50 mM sodium phosphate buffer pH 7.5 containing 0.6 M NaCl and 8.7% (vol/vol) glycerol. The sample was filtered through a 0.22 µm membrane filter, then loaded at 2 ml/min at 4° C. onto a metal chelate affinity column HiTrap Chelating of 5 ml (Amersham) loaded with Ni$^{2+}$ ions with a solution of 100 mM Ni(II)SO$_4$ (Fluka, ref 72280) using an Akta Purifier system (Amersham). Non-specifically bound material was removed by washing the column at 5 ml/min with 5 column volumes (CVs) of 50 mM sodium phosphate buffer pH 7.5 containing 0.6 M NaCl, 8.7% glycerol (Catalogue No: 49781; Fluka) and 20 mM imidazole (Fluka, ref 56749), The column was eluted in 5 ml fractions with 2 CVs of 50 mM sodium phosphate buffer, pH 7.5, containing 0.6 M NaCl, 8.7% glycerol and 400 mM imidazole (Catalogue No: 56749; Fluka) at 5.0 ml/min. The eluted protein peak was desalted by dialysis against 5 liters of 50 mM ammonium bicarbonate pH 8.0 for 16 h, lyophilized using a Freeze-dryer mobile 12EL (Virtis) and stored at −20° C.

d. Western Blot and SDS-PAGE Analysis of Recombinant Δ6 Evasin-4

For Western blot analysis the column eluate was diluted 1:3 with 4× sample buffer (bromophenol Blue with 125 mM Tris-HCl pH 6.8 containing 20% Glycerol, 10% SDS, 5 mM EDTA and 100 mM DTT) and boiled at 95° C. for 5 minutes. The samples and a His-tagged molecular weight standard (Catalogue No: LC5606; Invitrogen) were electrophoresed on a 10% Bis-Tris gel run in MES-buffer at 200 V for 35 minutes. The electrophoresed proteins were electro-transferred onto a 0.45 µm nitrocellulose membrane (Catalogue No: LC2001; Invitrogen) in transfer buffer (39 mM glycine, 48 mM Tris base, and 20% methanol, pH 8.3) for 1 hour at room temperature, using a constant current of 290 mA. The membrane was blocked by incubating in 20 ml blocking solution (0.1% Tween 20, 5% milk powder in PBS), for 1 hour at room temperature on a rocker platform. The membrane was then incubated in 15 ml of the solution containing the primary anti-histidine tag antibody (diluted 1:1000 in 0.1% Tween 20, 2.5% milk powder in PBS) for 2 hours at room temperature with shaking. The primary antibodies used were His-probe H-15 (sc-803; Santa Cruz Biotechnology) or His-probe G-18 (sc-804; Santa Cruz Biotechnology). The membrane was rinsed with wash buffer (0.1% Tween 20 in PBS) and washed with 3 changes of wash buffer (10 minutesutes each). The membrane was then incubated in HRP-conjugated secondary antibody (diluted 1:3000 in PBS with 0.1% Tween 20, 2.5% milk powder) for 2 hours at room temperature with shaking. The membrane was washed again as described previously. Finally, the membrane was blotted dry, and antibody staining was visualized using the ECL™ Western Blotting Detection Reagents kit (Catalogue No: RPN2106; Amersham Pharmacia), according to manufacturer's instructions.

For SDS-PAGE analysis, the column eluates were diluted 1:1 with 2× sample buffer (Invitrogen) containing 100 mM DTT and boiled for 5 minutes. The samples and a molecular weight standard (Benchmark Protein Ladder; Invitrogen) were electrophoresed on a 10% Bis-Tris gel run in MES-buffer at 200 V for 35 minutes. The electrophoresed proteins were stained using Simply Blue SafeStain (Invitrogen) according to the manufacturer's instructions: the gel was rinsed three times with distilled water for 5 minutes, stained for 1 hour at room temperature and washed with water for 1 hour.

Results

In order to produce recombinant Δ6 evasin-4, amino acids 24-127 of the predicted mature protein sequence were subcloned with a 6H is tag sequence at the 5' end of the ORF, in-frame with the signal peptide sequence of urokinase plasminogen activator (uPA) (FIG. 3) which replaced the natural predicted signal peptide sequence of evasin-4, into the mammalian cell expression vector pEAK12d or the insect cell expression vector (pDEST8). Recombinant Δ6 evasin-4 was purified from pEAK12d-spUPA-6His-Evasin-4 (FIG. 7) transfected HEK293 EBNA cell supernatants using $Ni^{2+}$-affinity chromatography. The Coomassie blue staining of an SDS-PAGE gel in which the purified protein was analyzed indicated that Δ6 evasin-4 was expressed and purified as a mixture of differentially post-translationally modified forms, possibly by glycosylation as shown for another tick protein expressed in insect cells (Alarcon-Chaidez F J et al., 2003). In fact, the protein appears as a smeared band, with an average molecular weight of around 30-40 Kd for the recombinant protein expressed in HEK293 (FIG. 9). The presence of recombinant Δ6 evasin-4 during the different purification steps from HEK293 was followed by Western blot analysis and by followed by Coomassie blue staining. The N-terminal of the purified, mature protein was sequenced, confirming that the sequence GSPNSHHH forms the N-terminus.

Example 3

Characterization of Recombinant Δ6 Evasin-4 Inhibitory Activity on CC-Chemokines In Vitro and In Vivo Materials and Methods
  a. Receptor Binding Assay.
  An equilibrium competition receptor binding assay was used to determine the inhibitory properties of recombinant Δ6 evasin-4 on the chemokine/chemokine receptor interaction. The binding experiments were performed using membranes prepared from CHO (Chinese hamster ovary cells) transfectants stably expressing the human CCR1 or CCR5 (CHO/CCR1 or CHO/CCR5). Recombinant Δ6 evasin-4, purified from HEK293 cells, was suspended at 0.1 mg/ml in 50 mM Tris/HCl pH 7.5 buffer containing 1 mM $CaCl_2$, 5 mM $MgCl_2$ and 0.5% BSA and eleven serial, 4-fold dilutions were prepared in a 96 well plate (F96 certified maxisort immunoplate, NUNC). Wheatgerm scintillation proximity assay beads (Amersham) stored at 50 mg/ml in 1×PBS at 4° C. were diluted to 10 mg/ml in the medium described above and membranes were diluted to 80 μg/ml in the same medium. 2 μg/well of CHO/CCR1 or CCR5 membranes, 250 μg/well beads, 0.1 nM [$^{125}$I]-RANTES (Amersham catalogue no: IM249) and 25 μl of the serial dilutions of recombinant Δ6 evasin-4 were added to each well of a 96 well clear, flat bottom plate (Corning) in a final volume of 100 μl to achieve a final concentration range of the recombinant protein from 350 μM to 0.08 μM. The mixture was then incubated 3 hours at room temperature with shaking and radioactivity was counted using α-scintillation counter (Wallac). See Results and FIG. 10.
  b. Binding Analysis by Surface Plasmon Resonance (SPR).
  Surface Plasmon Resonance (SPR) was used to measure the affinity and kinetics of chemokine binding by recombinant Δ6 evasin-4. Δ6 evasin-4 was suspended at 50 μg/ml in 10 mM sodium acetate buffer pH 4 (Biacore), and was directly immobilized on a CM4 chip (Biacore) by a standard amine coupling chemistry with the Biacore Amine coupling kit (Biacore), to achieve a level of 800 response units (RU) using a Biacore3000 system. A blank cell was prepared as a control with the chemical coupling reaction in the absence of protein. Experiments were performed at 25° C. and 30 μl/minute using HBS-P running buffer (0.01 M HEPES pH7.4, 0.15 M NaCl and 0.005% surfactant P20) (Biacore). For all binding experiments, chemokines were suspended at 0.1 μg/ml in running buffer and filtered through a 0.22 μm filter. The injection time was 3 minutes followed by a dissociation time of 2.5 minutes after injection. The chip was regenerated using 50 mM glycine buffer, pH 2.5 for 30 seconds. For each experiment, chemokines were injected in triplicate, in random order.

Figure 11:
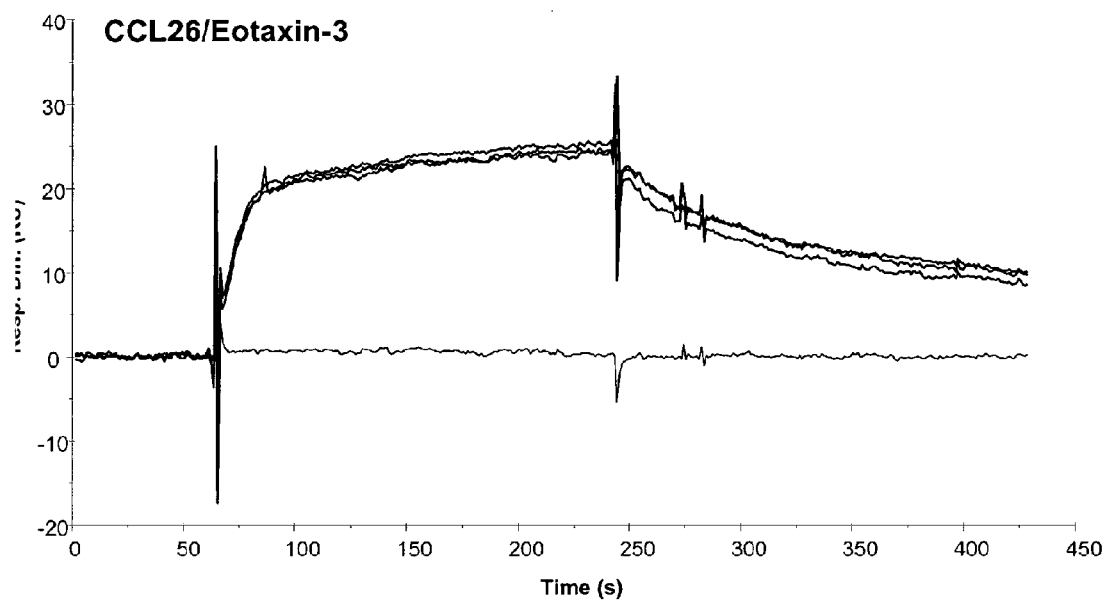
FIG. 11: Surface plasmon resonance (SPR) analysis of chemokine binding to Δ6 evasin-4 immobilized on a CM4 chip. A) CCL26/Eotaxin-3; B) E66A-CCL5/RANTES; C) CCL7/MCP-3; D) CXCL9/MIG; E) CCL18/PARC; F) CCL1/I-309; G) CCL3/MIP-1α; H) murine CCL3/MIP-1α; I) CCL22/MDC; J) CXCL11/I-TAC; K) CCL16/HCC-4; L) superimposed sensograms obtained for chemokines which do not appear to bind to Δ6 evasin-4:CCL4/MIP-1β, CCL2/MCP-1, CCL13/MCP-4, XCL1/lymphotactin, CCL17/TARC, CCL21/SLC, CCL15/HCC-2, CXCL12/SDF1α, CXCL8/IL8, CXCL1/Gro-α and CX$_3$CL1/fractalkine.
Figure 11:
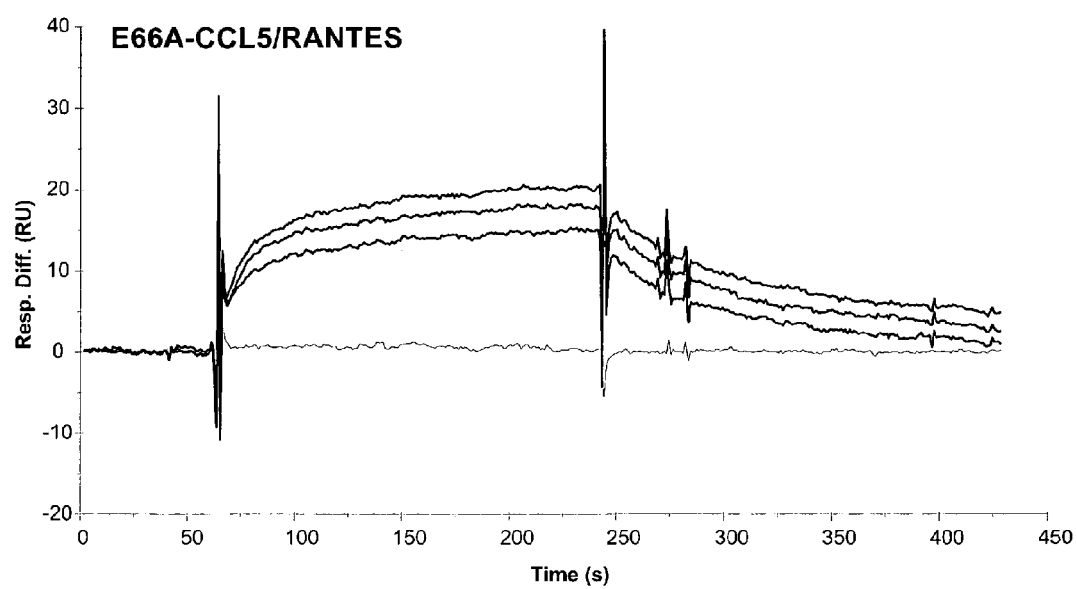
Figure 11:
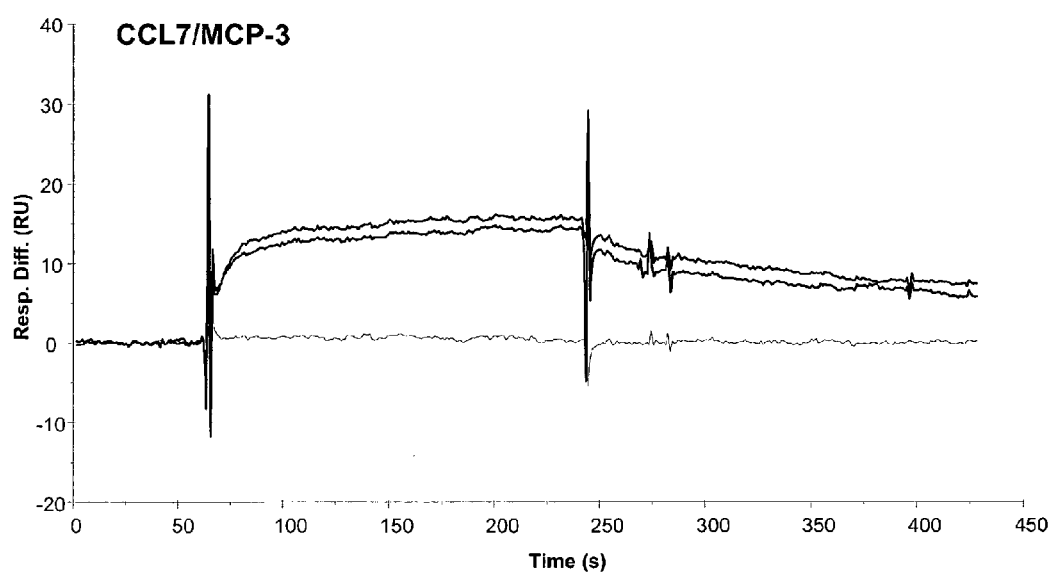
Figure 11:
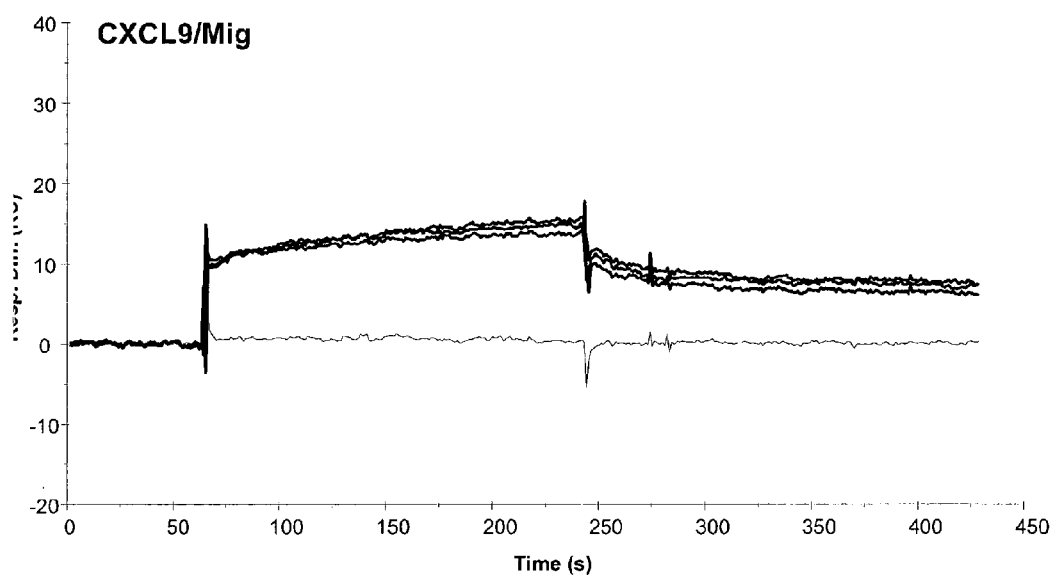
Figure 11:
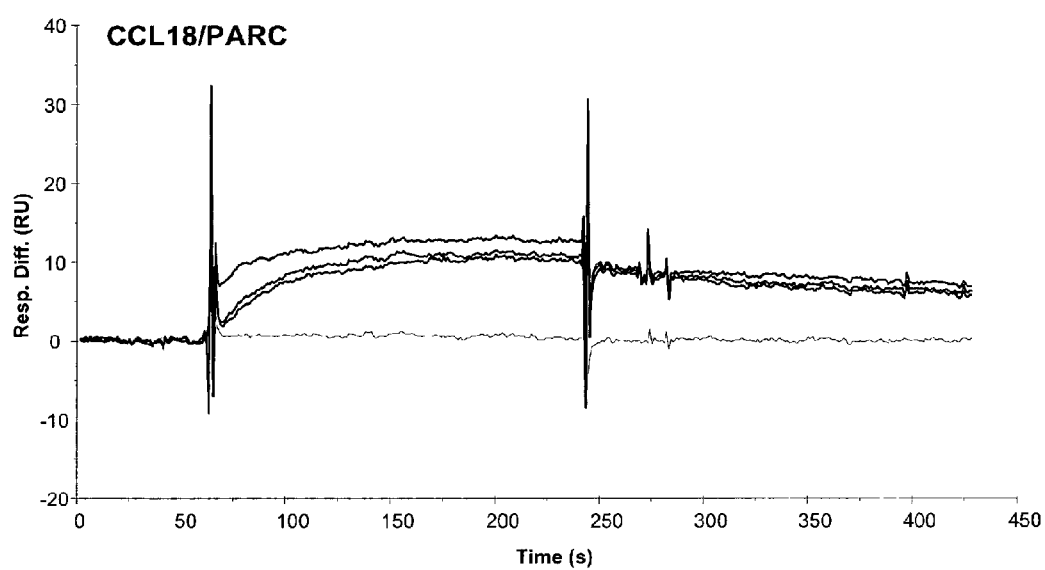
Figure 11:
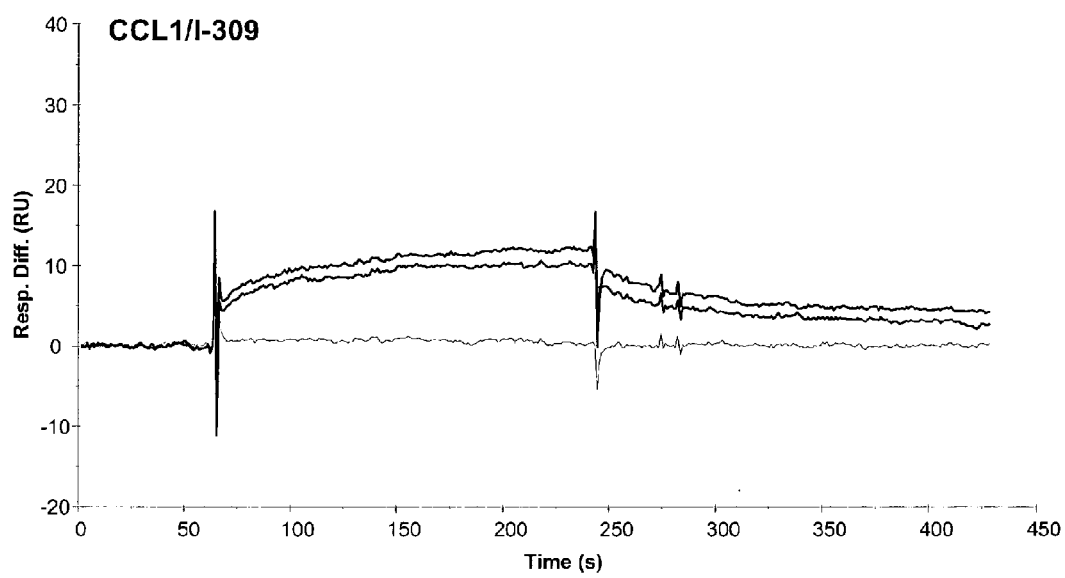
Figure 11:
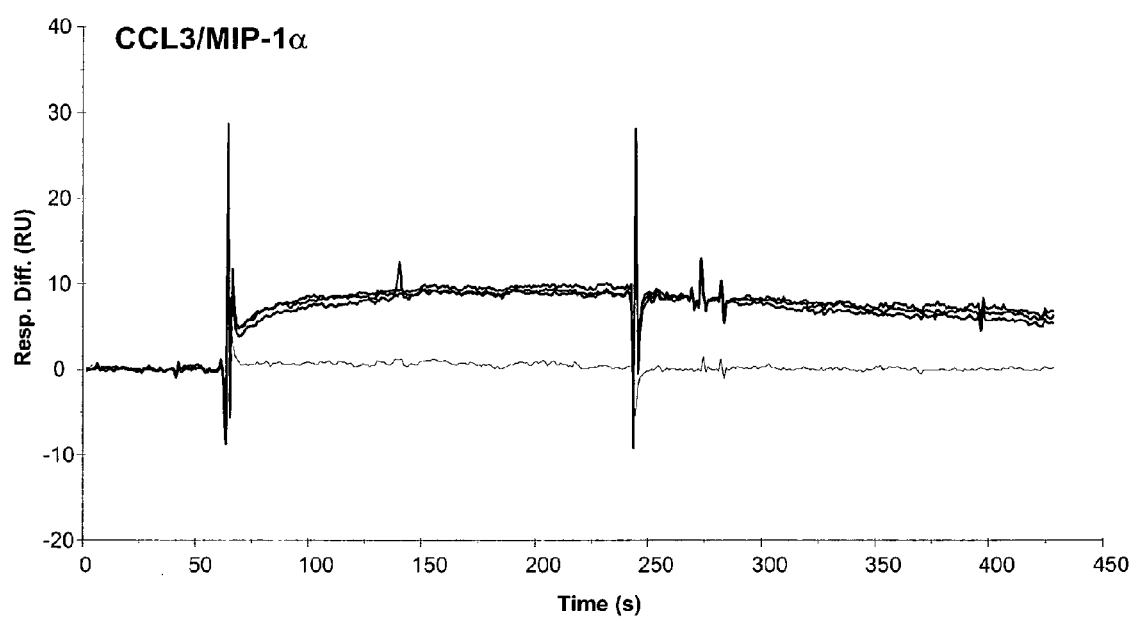
Figure 11:
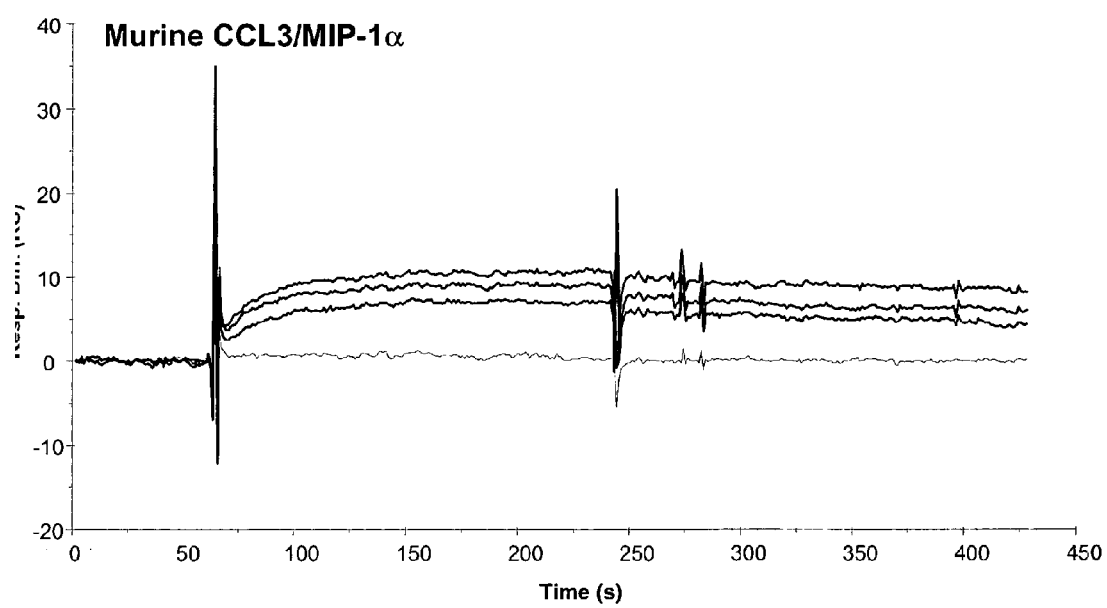
Figure 11:
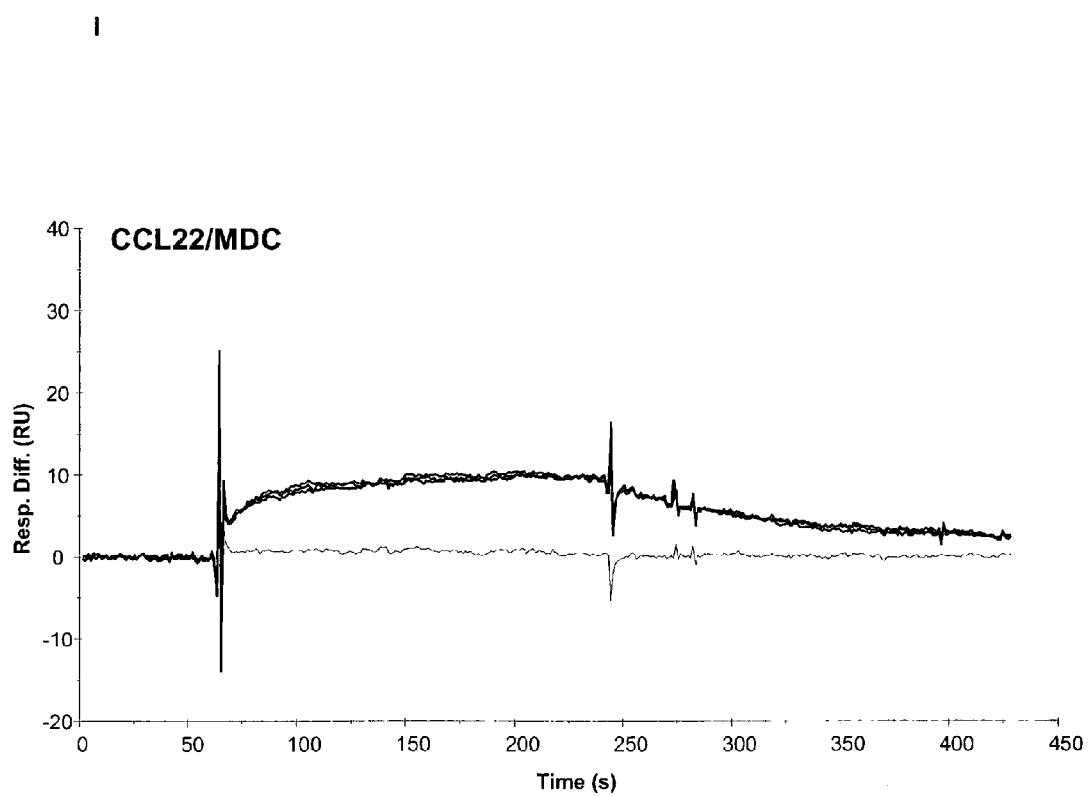
Figure 11:
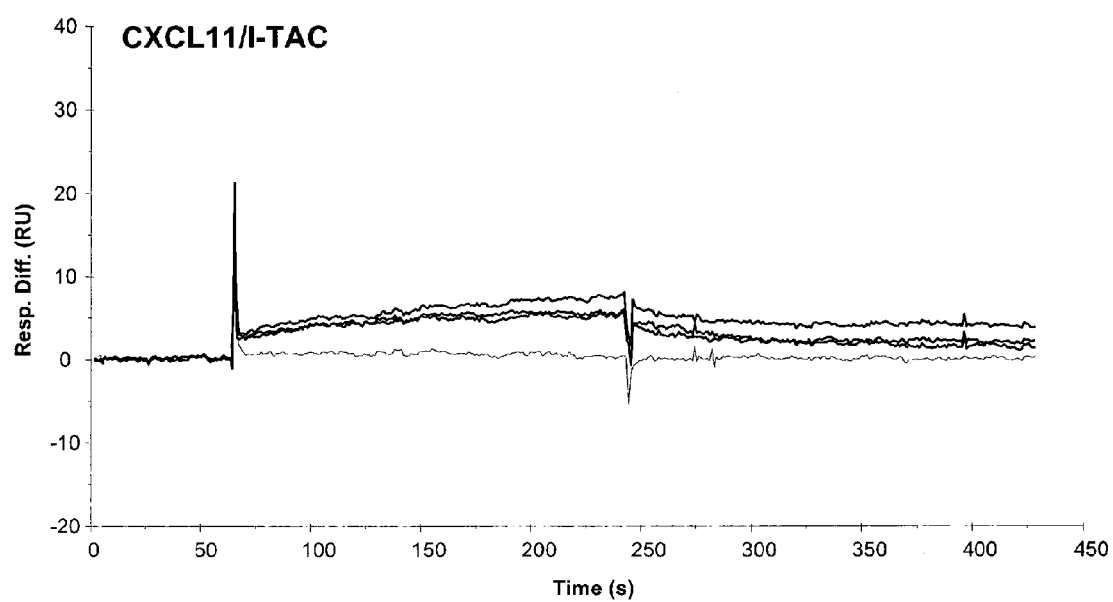
Figure 11:
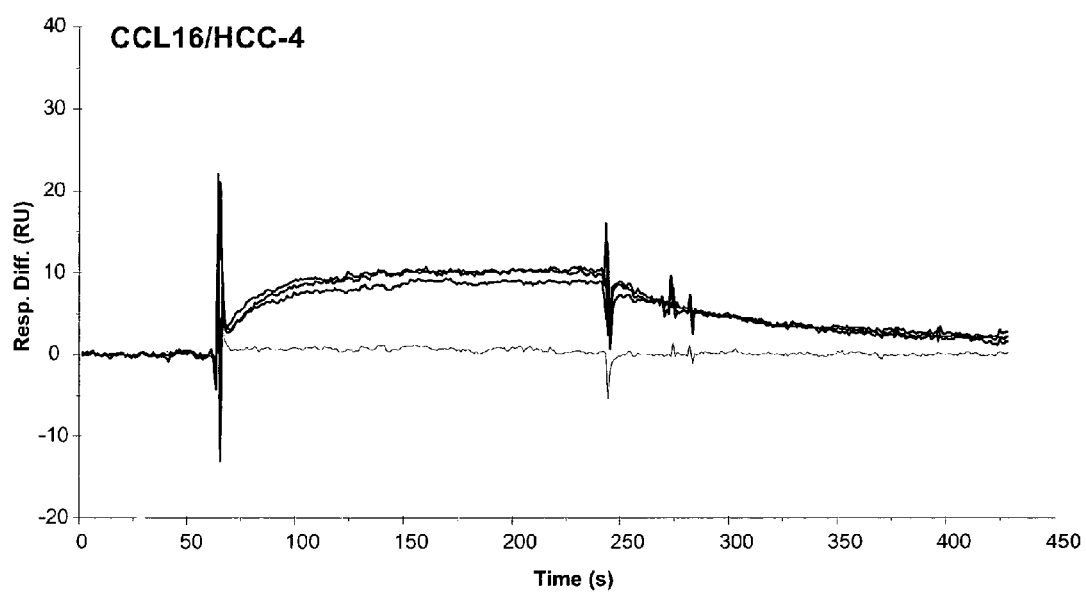
Figure 11:
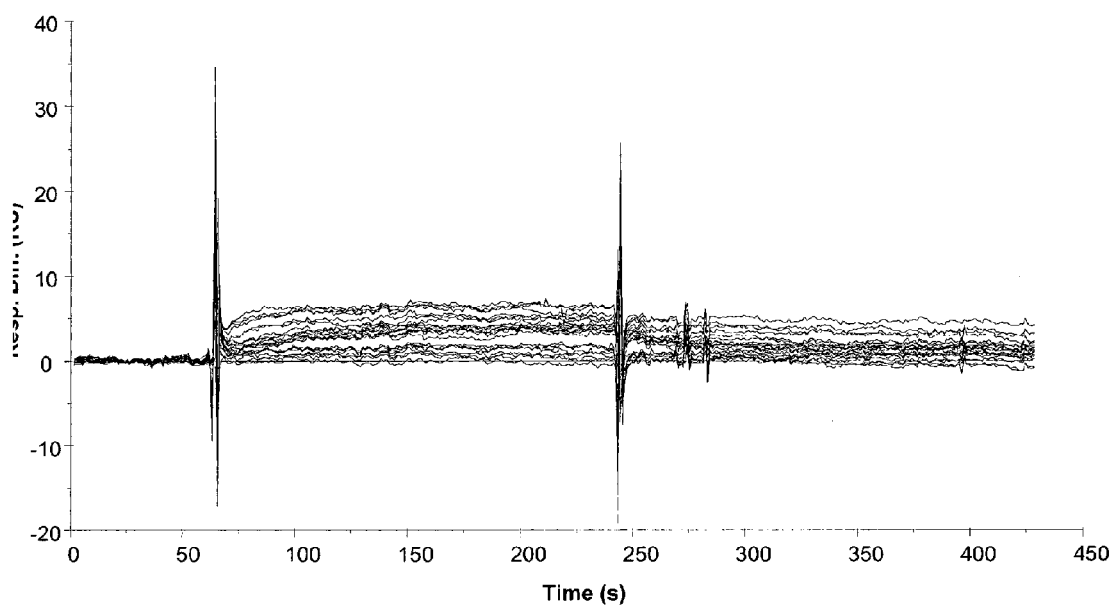

For the analysis, the sensograms from the blank cell, in addition to the sensograms obtained with the running buffer alone were subtracted from the binding to remove the noise from the system. See Results and FIG. 11.
  c. Inhibition of Chemokine Mediated Leukocyte Recruitment In Vivo
  Mice were given vehicle (saline) or evasin-4 at 1 and 10 μg/mouse subcutaneuously (s.c.) 45 minutes prior to the administration of 100 ng CC11/eotaxin into the pleural cavity of C57BI6 mice. After 24 hours, mice were killed and the total number of infiltrating leukocytes counted using a Neubauer chamber. Differential counts were performed on stained cytospin slides. There were 3-4 animals in each experimental group. See Results and FIG. 12.

Figure 12:
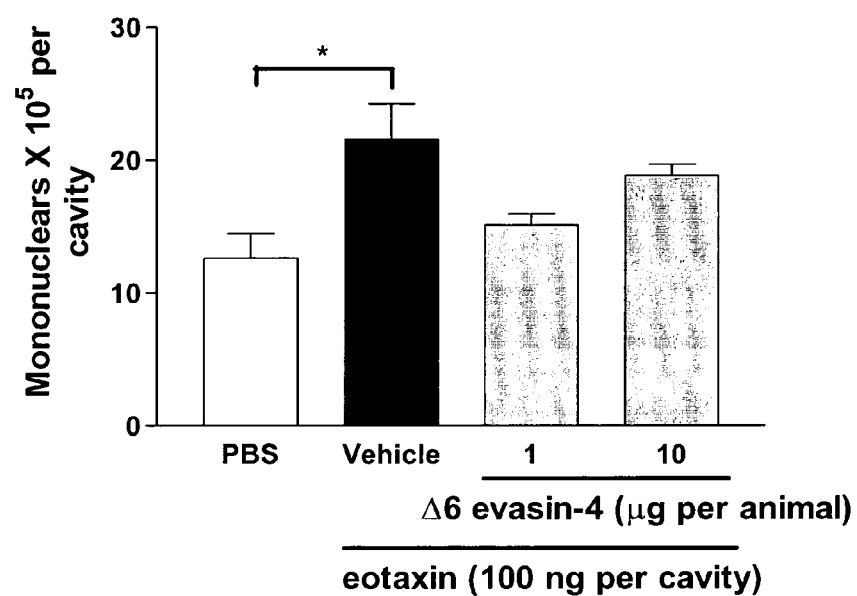
FIG. 12: Inhibition of cellular recruitment in vivo. Δ6 evasin-4 was administered into the pleural cavity of mice 45 minutes prior to the administration of CCL11/eotaxin. Cellular recruitment was measured 24 hours later. A, the number of total cells recruited; B, the number of eosinophils recruited; C, the number of mononuclear cells recruited by CCL11/eotaxin as shown in black bars, and the inhibition by 1 or 10 μg Δ6 evasin-4 is shown in hatched bars.

Results
  The chemokine binding properties of Δ6 evasin-4 were studied in a receptor binding assay and by Surface Plasmon Resonance.
  The receptor binding assay demonstrated that Δ6 evasin-4 expressed in mammalian cells (HEK293 cells) was able to inhibit the binding of iodinated RANTES to CCR1 and CCR5, with $IC_{50}$ values of 7 and 3 nM respectively (FIGS. 10 A and B). SPR analysis showed that Δ6 evasin-4 is able to bind several members of the chemokine family. (FIG. 11A to L).
  The inhibitory activity of Δ6 evasin-4 was further demonstrated by its ability to inhibit the recruitment of leukocytes induced by the administration of the eotaxin/CCL11 into the pleural cavity at doses of 1 and 10 μg/mouse (FIG. 12). There was a reduction of the number of total cells recruited (FIG. 12A), and after enumeration of the different cell types, a significant reduction in the number of eosinophils was observed (FIG. 12B), with a smaller reduction in the number of mononuclear cells recruited (FIG. 12C)

Example 4

Generation of an Expression Construct Containing the Full Length Mature Amino Acid Sequence of Evasin-4 with an N-Terminal 6 HIS Tag for Expression in HEK293/EBNA Cells Site directed mutagenesis was performed on plasmid pDONR221-spUPA-6H-Evasin-4 (FIG. 6) to restore the sequence encoding amino acids 18-23 (WLSTKC) of the full length evasin-4 sequence. The PCR reaction (in a final volume of 50 μl) was performed in quadruplicate and contains: 2 μl (20 ng) of plasmid pDONR221-spUPA-6His-Evasin-4, 1 μl dNTP mix, 5 μl of 10× reaction buffer, 2 μl each of gene specific primer (62.5 μM) 6His-WLSTKC-Evasin-4F and 6His-WLSTKC-Evasin-4R (SEQ ID NO: 26 and 27), and 1 μl Pfu Ultra HF DNA polymerase according to the manufacturer's instructions. The PCR reaction was performed using an initial denaturing step of 95° C. for 30 s, followed by 18 cycles of 95° C. for 30 s; 55° C. for 1 minute and 68° C. for 4 min; a cycle of 68° C. for 7 min and a holding cycle of 4° C.
  The second stage of the site directed mutagenesis process involves the treatment of the PCR product with Dpn1 endonuclease, specific for methylated and hemimethylated DNA, to digest the parental methylated plasmid DNA in order to select for newly synthesized DNA which contains the mutation (insertion). The PCR product was incubated with 1 μl Dpn1 restriction enzyme (10 U/μl) at 37° C. for 1 hour, according to manufacturer's instructions.

An aliquot of Dpn 1 digestion reaction (1 μl) was used to transform *E. Coli* XL-10 blue cells by heat shock as follows: a 50 μl aliquot of XL-1blue competent cells (Stratagene) was thawed on ice and 1 μl of the Dpn 1 reaction mix was added. The mixture was incubated on ice for 30 minutes and cells were heat-shocked at 42° C. for 45 seconds. The cells were then transferred to an ice bath for 2 minutes. NZY medium (0.5 ml), pre-warmed to 42° C., was then added. The mixture was transferred to a 15 ml snap-cap tube and incubated, with shaking (220 rpm) for 1 hour at 37° C. Aliquots of the transformation mixture (250 μl) were then plated on L-broth (LB) plates containing ampicillin (100 μg/ml) and incubated overnight at 37° C.

Plasmid mini-prep DNA was prepared from 5 ml cultures from 60 of the resultant colonies using a Qiaprep Turbo 9600 robotic system (Qiagen). Plasmid DNA (200-500 ng) was subjected to DNA sequencing with 21M13 and M13Rev primers using the BigDyeTerminator system (Applied Biosystems cat. no. 4336919) according to the manufacturer's instructions. Sequencing reactions were purified using Montage SEQ 96 cleanup plates (Millipore cat. no. LSKS09624) then analyzed on an Applied Biosystems 3700 DNA sequencer.

The mutated ORF (FIG. 13) from one a plasmid which contained the correct insert sequence (pDONR221-spUPA-Evasin-4FL, FIG. 14) was then transferred into pEAK12d or pDEST in a recombination reaction containing 1.5 μl or approx. 100 ng of plasmid eluate, 1.5 μl of either pDEST8 vector or pEAK12d vector (0.1 μg/μl), 2 μl LR buffer and 1.5 μl of LR clonase (Invitrogen) in a final volume of 10 μl. The reaction mixtures were incubated at room temperature for 1 hour then stopped by addition of Proteinase K (2 μg) and incubated at 37° C. for a further 10 minutes. An aliquot of each reaction (1 μl) was used to transform *E. coli* DH10B cells by electroporation as follows: a 20 μl aliquot of DH10B electrocompetent cells (Invitrogen) was thawed on ice and 1 μl of the LR reaction mix was added. The mixture was transferred to a chilled 0.1 cm electroporation cuvette and the cells electroporated using a BioRad Gene-Pulser™ according to the manufacturer's recommended protocol. SOC media (1 ml), pre-warmed to room temperature, was added immediately after electroporation. The mixture was transferred to a 15 ml snap-cap tube and incubated, with shaking (220 rpm) for 1 hour at 37° C. Aliquots of the transformation mixture (10 μl and 100 μl) were then plated on L-broth (LB) plates containing ampicillin (100 μg/ml) and incubated overnight at 37° C.

Five colonies per transformation were then analysed by colony PCR. The colonies are suspended in 50 μl of sterile water and a 25 ul aliquot was subjected to PCR (in a final volume of 50 μl) containing 2 μl dNTPs (5 mM), 5 μl of 10× AmpliTaq polymerase buffer containing 15 mM $MgSO_4$, 2.5 μl each of vector specific primer (10 μM) (pEAK12F and pEAK12R for the pEAK12d vector and pDEST8F and pDEST8R for the pDEST8 vector), and 0.5 μl AmpliTaq DNA polymerase (Invitrogen). The PCR reaction was performed using an initial denaturing step of 96° C. for 2 min; 35 cycles of 94° C. for 30 seconds, 55° C. for 30 seconds and 72° C. for 30 second. The resultant PCR product was visualized on a 1.5% agarose gel in 1×TAE buffer (Invitrogen) and one colony containing the correct insert was chosen for DNA purification. Plasmid mini-prep DNA was prepared from 5 ml cultures inoculated with 5 μl of the suspended colony sub-cloned into each vector using a Qiaprep Bio Robot 8000 (Qiagen) and stored at −20° C.

The sequences of primers used in the different sub-/cloning steps are listed in Table III.

Results

Figure 14:
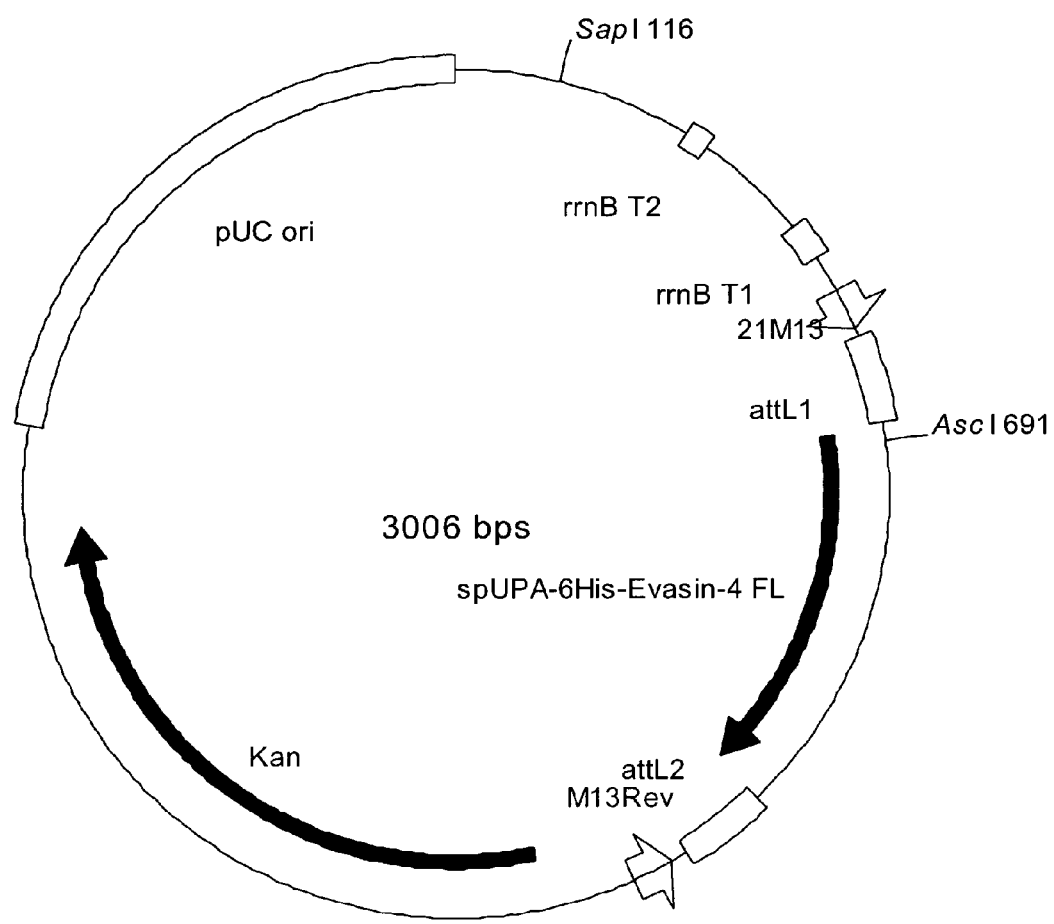
FIG. 14: Map of pDONR221-spUPA-6His-Evasin-4 FL vector. Gateway entry vector.
Figure 15:
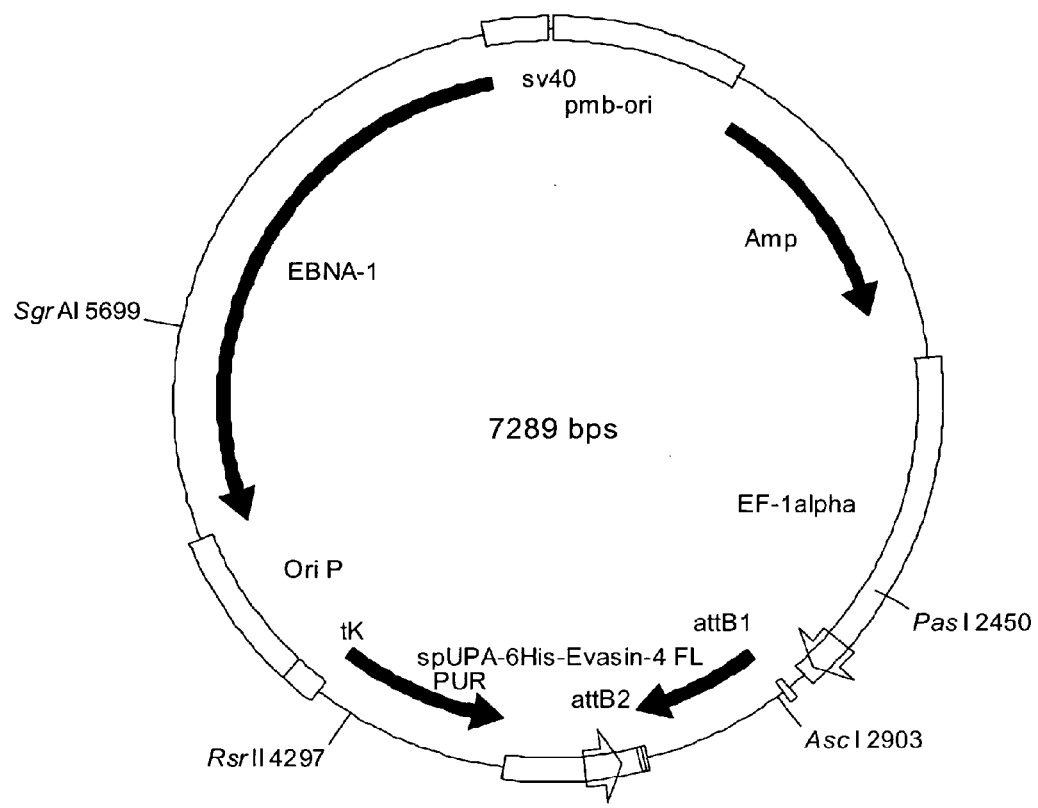
FIG. 15: Map of pEAK12d-spUPA-6His-Evasin-4 FL. Gateway expression vector for expression in human embryonic kidney cells HEK293/EBNA cells.
Figure 16:
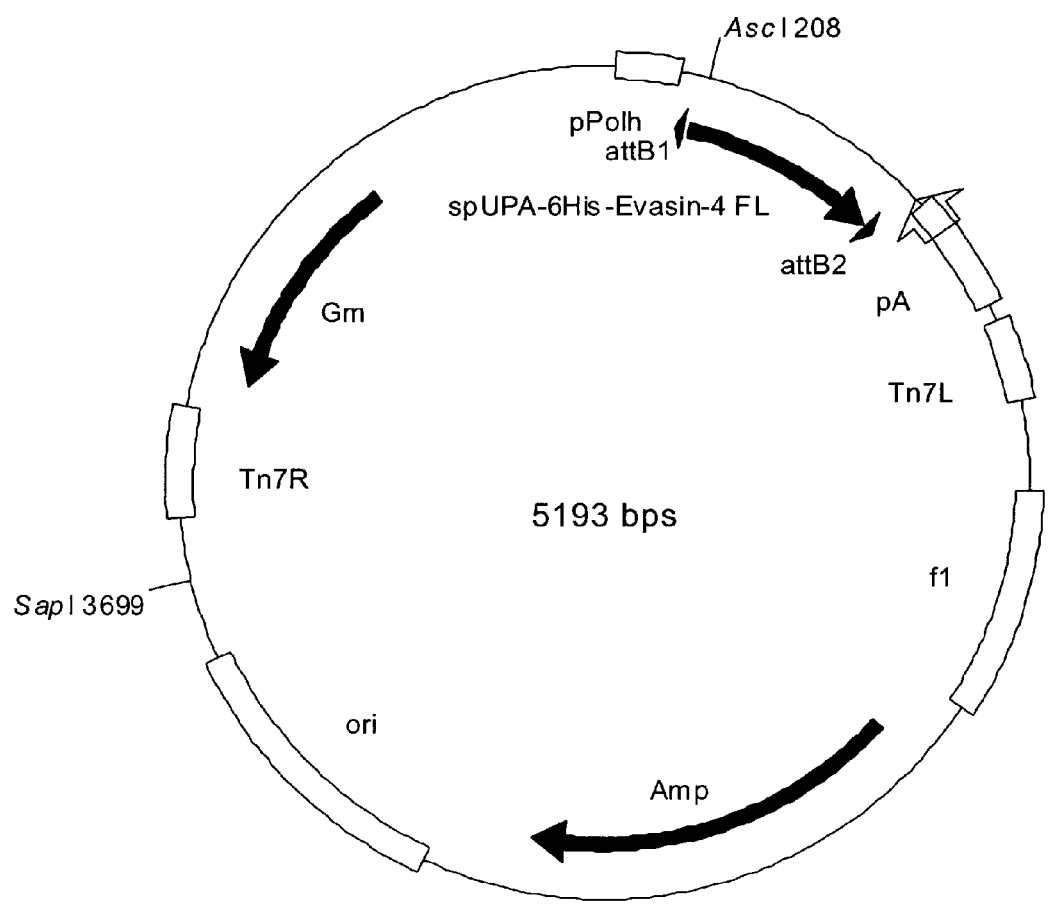
FIG. 16: Map of pDEST8-spUPA-6His-Evasin-4 FL Gateway expression vector for expression in TN5 (insect) cells.

In order to produce recombinant evasin-4 FL, site directed mutagenesis was performed on plasmid pDONR221-spUPA-6H-Evasin-4 (FIG. 6) to restore the sequence encoding amino acids 18-23 (WLSTKC) of the full length evasin-4 sequence (FIG. 14). The resultant cDNA sequence, containing in order, from the 5' end, the signal peptide sequence of uPA fused to a five amino acid flexible linker sequence (GSPNS) followed by a 6 histidine tag sequence, a second flexible linker (GSPNS) and caspase 8 cleavage site (LETD) sequence followed by the cDNA sequence encoding amino acids 18-127 of evasin-4 (SEQ ID NO: 25) was then subcloned into the mammalian cell expression vector, pEAK12d, (FIG. 15) or the insect cell expression vector, pDEST8, (FIG. 16) by recombination using the Gateway cloning system.

CONCLUSIONS

Therefore, it can be concluded that evasin-4 is a novel protein having CC-chemokine binding properties, which is able to inhibit the action of chemokines. This protein can be usefully applied in human medicine as an anti-inflammatory compound, as well as in medical and veterinary indications related to the parasitic effects of ticks, including tick-borne infectious agents. Molecules based on the proteins of the invention and interfering with the function of such proteins, might disrupt the tick life-cycle, control ectoparasites and their pathogens, or reduce tick's ability to transmit disease-causing organisms

TABLE I

| Amino Acid | Synonymous Group | More Preferred Synonymous Groups |
|---|---|---|
| Ser | Gly, Ala, Ser, Thr, Pro | Thr, Ser |
| Arg | Asn, Lys, Gln, Arg, His | Arg, Lys, His |
| Leu | Phe, Ile, Val, Leu, Met | Ile, Val, Leu, Met |
| Pro | Gly, Ala, Ser, Thr, Pro | Pro |
| Thr | Gly, Ala, Ser, Thr, Pro | Thr, Ser |
| Ala | Gly, Thr, Pro, Ala, Ser | Gly, Ala |
| Val | Met, Phe, Ile, Leu, Val | Met, Ile, Val, Leu |
| Gly | Ala, Thr, Pro, Ser, Gly | Gly, Ala |
| Ile | Phe, Ile, Val, Leu, Met | Ile, Val, Leu, Met |
| Phe | Trp, Phe, Tyr | Tyr, Phe |
| Tyr | Trp, Phe, Tyr | Phe, Tyr |
| Cys | Ser, Thr, Cys | Cys |
| His | Asn, Lys, Gln, Arg, His | Arg, Lys, His |
| Gln | Glu, Asn, Asp, Gln | Asn, Gln |
| Asn | Glu, Asn, Asp, Gln | Asn, Gln |
| Lys | Asn, Lys, Gln, Arg, His | Arg, Lys, His |
| Asp | Glu, Asn, Asp, Gln | Asp, Glu |
| Glu | Glu, Asn, Asp, Gln | Asp, Glu |
| Met | Phe, Ile, Val, Leu, Met | Ile, Val, Leu, Met |
| Trp | Trp, Phe, Tyr | Trp |

TABLE II

| Amino Acid | Synonymous Group |
|---|---|
| Ser | D-Ser, Thr, D-Thr, allo-Thr, Met, D-Met, Met(O), D-Met(O), L-Cys, D-Cys |
| Arg | D-Arg, Lys, D-Lys, homo-Arg, D-homo-Arg, Met, Ile, D-.Met, D-Ile, Orn, D-Orn |

TABLE II-continued

| Amino Acid | Synonymous Group |
|---|---|
| Leu | D-Leu, Val, D-Val, AdaA, AdaG, Leu, D-Leu, Met, D-Met |
| Pro | D-Pro, L-I-thioazolidine-4-carboxylic acid, D-or L-1-oxazolidine-4-carboxylic acid |
| Thr | D-Thr, Ser, D-Ser, allo-Thr, Met, D-Met, Met(O), D-Met(O), Val, D-Val |
| Ala | D-Ala, Gly, Aib, B-Ala, Acp, L-Cys, D-Cys |
| Val | D-Val, Leu, D-Leu, Ile, D-Ile, Met, D-Met, AdaA, AdaG |
| Gly | Ala, D-Ala, Pro, D-Pro, Aib, .beta.-Ala, Acp |
| Ile | D-Ile, Val, D-Val, AdaA, AdaG, Leu, D-Leu, Met, D-Met |
| Phe | D-Phe, Tyr, D-Thr, L-Dopa, His, D-His, Trp, D-Trp, Trans-3,4, or 5-phenylproline, AdaA, AdaG, cis-3,4, or 5-phenylproline, Bpa, D-Bpa |
| Tyr | D-Tyr, Phe, D-Phe, L-Dopa, His, D-His |
| Cys | D-Cys, S--Me--Cys, Met, D-Met, Thr, D-Thr |
| Gln | D-Gln, Asn, D-Asn, Glu, D-Glu, Asp, D-Asp |
| Asn | D-Asn, Asp, D-Asp, Glu, D-Glu, Gln, D-Gln |
| Lys | D-Lys, Arg, D-Arg, homo-Arg, D-homo-Arg, Met, D-Met, Ile, D-Ile, Orn, D-Orn |
| Asp | D-Asp, D-Asn, Asn, Glu, D-Glu, Gln, D-Gln |
| Glu | D-Glu, D-Asp, Asp, Asn, D-Asn, Gln, D-Gln |
| Met | D-Met, S--Me--Cys, Ile, D-Ile, Leu, D-Leu, Val, D-Val |

REFERENCES

Aijamali M N et al., Insect Mol Biol, 12: 299-305, 2003.
Baggiolini M et al., Annu Rev Immunol, 15: 675-705, 1997.
Baggiolini M, J Intern Med, 250: 91-104, 2001.
Brown A et al., J Pept Sci, 2:40-46, 1996.
Chuang V T et al., Pharm Res., 19: 569-577, 2002.
Clackson et al., Nature, 352:624-628, 1991.
Dougherty D A, Curr Opin Chem Biol, 4: 645-52, 2000.
Ferreira B R and Silva J S, Vet Immunol Immunopathol, 64: 279-293, 1998.
Gendel S M, Ann NY Acad SCI, 964: 87-98, 2002.
Gillespie R D et al., J Immunol, 166: 4319-4326, 2001.
Goding, Monoclonal Antibodies: Principles and Practice, Academic Press, (1986) pp. 59-103
Hajnicka, V., et al., Parasitology 130:333-342, 2005.
Harris J M and Chess R B, Nat Rev Drug Discov, 2: 214-221, 2003.
Hill C A and Gutierrez J A, Med Vet Entomol, 17: 224-227, 2003.
Hoogenboom and Winter, J. Mol. Biol, 227:381, 1991.
Hruby V J and Balse P M, Curr Med Chem, 7: 945-970, 2000.
Jensen K K et al., J Virol, 77: 624-630, 2003.

TABLE III

| Primer | Sequence (5'-3') |
|---|---|
| spUPA PCR1F | GCAGGCTTC<u>GCCACC</u>ATGAGAGCCCTGCTGGCGCG |
| spupa-GSPNS R | *GATGGTGATGGG*AATTCGGGGATCCGCCTTTACTGTCGCTCACG |
| SPNS-LETD_Evasin-4F | ATCCCCGAATTCCCTGGAGACCGATGAAGTGCCACAAATGAC |
| Evasin-4 PCR1R | GTACAAGAAAGCTGGGTTTCACCAGCACTGAGCGTGTCGA |
| 6H-GSPNS-Evasin-4F | ATTCC*CATCACCATCACCATCAC*GGATCCCCGAATTCCCTGGAGAC |
| Evasin-4 PCR2F | GGGGACAAGTTTGTACAAAAAAGCAGGCTTC<u>GCCACC</u> |
| Evasin-4 PCR2R | GGGGACCACTTTGTACAAGAAAGCTGGGTT |
| 21M13 | TGTAAAACGACGGCCAGT |
| M13Rev | CAGGAAACAGCTATGACC |
| pEAK12F | GCCAGCTTGGCACTTGATGT |
| pEAK12R | GATGGAGGTGGACGTGTCAG |
| pDEST8F | TCTTCTACGGCAAGGTGCTG |
| pDEST8R | AAGCAAGTAAAACCTCTACA |
| 6His-WLSTKC-Evasin-4_F | CCTGGAGACCGATTGGCTCAGCACTAAATGCGAAGTGCCACAAATG |
| 6His-WLSTKC-Evasin-4_R | CATTTGTGGCACTTCGCATTTAGTGCTGAGCCAATCGGTCTCCAGG |

<u>Underlined</u> sequence = Kozak sequence
Bold = Start codon/Stop codon
*Italic* sequence = His tag Jones et al., Nature, 321:522-525, 1986.
Kohler et al, Nature 256: 495, 1975
Luo B and Prestwich G D, Exp Opin Ther Patents, 11: 1395-1410, 2001.
Madden R D et al., Exp Appl Acarol, 32: 77-87, 2004.
Marshall S A et al., Drug Disc Today, 8: 212-221, 2003.
Mulenga A et al., Microbes Infect, 2: 1353-1361, 2000.
Murphy L R et al., Protein Eng, 13:149-152, 2000.
Murrell A et al., Mol Phylogenet Evol, 21: 244-258, 2001.
Nilsson J et al., Protein Expr Purif, 11: 1-16, 1997.
Pearson W R, Methods Mol. Biol., 132:185-219, 2000.
Pillai O and Panchagnula R, Cur Opin Chem Biol, 5: 447-451, 2001.
Rapoport T A et al., Annu Rev Biochem., 65:271-303, 1996.
Rogov S I and Nekrasov A N, Protein Eng, 14: 459-463, 2001.
Scatchard G., Ann NY Acad. Sci. 51: 660-672, 1949
Schellekens H, Nat Rev Drug Disc, 1: 457-462, 2002.
Ullmann A J et al., Exp Appl Acarol, 28: 107-126, 2002.
Vaitukaitis et al. J Clin Endocrinol Metab. 33, p. 988, 1971
Valenzuela J G, Am J Trop Med Hyg, 66: 223-224, 2002.
Vasserot A P et al., Drug Disc Today, 8: 118-126, 2003.
Van Valkenburgh H A and Kahn R A, Methods Enzymol., 344:186-193, 2002.
Villain M et al., Chem Biol, 8: 673-679, 2001.
Wang H et al., Exp Appl Acarol 1999, 23: 969-975, 1999.
Ward et al., Nature 341:544, 1989

The invention claimed is:

1. An isolated polypeptide that:
   a) comprises SEQ ID NO: 5;
   b) comprises SEQ ID NO: 6; or
   c) a fusion protein comprising any one of a) or b) operably linked to a heterologous sequence selected from an extracellular domain of a membrane-bound protein, an immunoglobulin constant region, a multimerization domain, a heterodimeric protein hormone, a signal peptide, an export signal, or a tag sequence.

2. The isolated polypeptide of claim 1, wherein said polypeptide is post-translationally modified.

3. The isolated polypeptide of claim 2, wherein said polypeptide is glycosylated.

4. The isolated polypeptide of claim 2, wherein said polypeptide is PEGylated or coupled to a label or agent.

5. The isolated polypeptide of claim 1, wherein said polypeptide binds to a CC-chemokine selected from CCL5 or CCL11.

6. The isolated polypeptide of claim 1, wherein said polypeptide comprises SEQ ID NO: 5.

7. The isolated polypeptide of claim 1, wherein said polypeptide consists of SEQ ID NO: 5.

8. The isolated polypeptide of claim 1, wherein said polypeptide comprises SEQ ID NO: 6.

9. The isolated polypeptide of claim 1, wherein said polypeptide consists of SEQ ID NO: 6.

10. The isolated polypeptide of claim 1, wherein said polypeptide is a fusion protein comprising SEQ ID NO: 5 operably linked to a heterologous sequence selected from an extracellular domain of a membrane-bound protein, an immunoglobulin constant region, a multimerization domain, a heterodimeric protein hormone, a signal peptide, an export signal, or a tag sequence.

11. The isolated polypeptide of claim 1, wherein said polypeptide is a fusion protein comprising SEQ ID NO: 6 operably linked to a heterologous sequence selected from an extracellular domain of a membrane-bound protein, an immunoglobulin constant region, a multimerization domain, a heterodimeric protein hormone, a signal peptide, an export signal, or a tag sequence.

12. An isolated nucleic acid molecule encoding a polypeptide according to claim 1.

13. The isolated nucleic acid of claim 12, wherein said nucleic acid encodes a polypeptide comprising SEQ ID NO: 5.

14. The isolated nucleic acid of claim 12, wherein said nucleic acid encodes a polypeptide consisting of SEQ ID NO: 5.

15. The isolated nucleic acid of claim 12, wherein said nucleic acid encodes a polypeptide comprising SEQ ID NO: 6.

16. The isolated nucleic acid of claim 12, wherein said nucleic acid encodes a polypeptide consisting of SEQ ID NO: 6.

17. The isolated nucleic acid of claim 12, wherein said nucleic acid encodes a fusion protein comprising SEQ ID NO: 5 operably linked to a heterologous sequence selected from an extracellular domain of a membrane-bound protein, an immunoglobulin constant region, a multimerization domain, a heterodimeric protein hormone, a signal peptide, an export signal, or a tag sequence.

18. The isolated nucleic acid of claim 12, wherein said nucleic acid encodes a fusion protein comprising SEQ ID NO: 6 operably linked to a heterologous sequence selected from an extracellular domain of a membrane-bound protein, an immunoglobulin constant region, a multimerization domain, a heterodimeric protein hormone, a signal peptide, an export signal, or a tag sequence.

19. The nucleic acid molecule of claim 12, wherein said nucleic acid is a cDNA molecule.

20. The nucleic acid molecule of claim 12, wherein said nucleic acid comprises SEQ ID NO: 3.

21. The nucleic acid molecule of claim 12, wherein said nucleic acid comprises SEQ ID NO: 4.

22. An isolated oligonucleotide that comprises a fragment of at least 30 nucleotides of a nucleic acid molecule encoding a polypeptide of claim 1.

23. The isolated oligonucleotide of claim 22, wherein said oligonucleotide has a length of at least 50 nucleotides.

24. A cloning or expression vector comprising a nucleic acid molecule encoding a polypeptide of claim 1.

25. The expression vector of claim 24, wherein said nucleic acid molecule is operably associated with a promoter.

26. An isolated transformed host cell comprising a cloning or expression vector comprising a nucleic acid molecule encoding a polypeptide of claim 1.

27. A process for preparing a polypeptide comprising culturing a host cell of claim 26 under conditions allowing or promoting expression of said polypeptide.

28. The process of claim 27, further comprising purifying the protein.

29. The process of claim 27, further comprising formulating the polypeptide into a pharmaceutical composition.

30. A pharmaceutical composition comprising a polypeptide of claim 1.

31. A method for immunizing an animal against a blood-feeding ectoparasite, comprising administering to said animal a polypeptide of claim 1 in an amount sufficient to induce an immune response.

\* \* \* \* \*

UNITED STATES PATENT AND TRADEMARK OFFICE
CERTIFICATE OF CORRECTION

PATENT NO. : 7,611,867 B2
APPLICATION NO. : 12/096107
DATED : November 3, 2009
INVENTOR(S) : Proudfoot et al.

It is certified that error appears in the above-identified patent and that said Letters Patent is hereby corrected as shown below:

Column 3,
Lines 46-47, "(SEQ ID NO: 25) and translation (SEQ ID NO: 29) 8)" should read
--(SEQ ID NO: 11) and translation (SEQ ID NO: 28)--.

Column 4,
Line 10, "anti-6H is" should read --anti-6His--.
Line 22, "CCL1/1-309" should read --CCL1/I-309--.
Line 41, "(amino acids 1 20)" should read --(amino acids 1-20)--.

Column 9,
Line 17, "allows the formation or" should read --allows the formation of--.
Line 20, "proteins such hCG" should read --proteins such as hCG--.

Column 13,
Line 44, "derived form viral sources" should read --derived from viral sources--.

Column 23,
Lines 42-44, "for example, sesame oil, or synthetic fatty acid esters, for example, sesame
oil, or synthetic fatty acid esters, for example, ethyl" should read
--for example, sesame oil, or synthetic fatty acid esters, for example, ethyl--.

Column 27,
Line 27, "peptide of UPA" should read --peptide of uPA--.

Column 28,
Line 40, "Five ill of" should read --Five µl of--.

Column 30,
Line 40, "(10 minutesutes each)." should read --(10 minutes each).--.
Line 64, "a 6H is tag" should read --a 6His tag--.

Column 31,
Line 16, "and by followed by Coomassie" should read --and Coomassie--.
Line 40, "to 0.08 µM" should read --to 0.08 pM--.
Line 52, "using α-scintillation counter" should read --using a β-scintillation counter--.

CERTIFICATE OF CORRECTION (continued)
U.S. Pat. No. 7,611,867 B2

Column 33,
Line 28, "from one a plasmid" should read --from a plasmid--.
Line 63, "for 30 second." should read --for 30 seconds.--.

Column 49,
Line 53, "polypeptide hinds" should read --polypeptide binds--.

Signed and Sealed this

Second Day of February, 2010

David J. Kappos
*Director of the United States Patent and Trademark Office*

SEQUENCE LISTING

<160> NUMBER OF SEQ ID NOS: 27

<210> SEQ ID NO 1
<211> LENGTH: 92
<212> TYPE: PRT
<213> ORGANISM: Rhipicephalus sanguineus

<400> SEQUENCE: 1

```
Met Val Ser Met Lys Thr Thr His His Val Leu Phe Leu Leu Val Ala
1               5                   10                  15

Leu Glu Ser Met Arg Pro Tyr Thr Thr Ala Leu Val Ser Thr Ile Glu
            20                  25                  30

Ser Arg Thr Ser Gly Asp Gly Ala Asp Asn Phe Asp Val Val Ser Cys
        35                  40                  45

Asn Lys Asn Cys Thr Ser Gly Gln Asn Glu Cys Pro Glu Gly Cys Phe
    50                  55                  60

Cys Gly Leu Leu Gly Gln Asn Lys Lys Gly His Cys Tyr Lys Ile Ile
65                  70                  75                  80

Gly Asn Leu Ser Gly Glu Pro Pro Val Val Arg Arg
            85                  90
```

<210> SEQ ID NO 2
<211> LENGTH: 491
<212> TYPE: DNA
<213> ORGANISM: Rhipicephalus sanguineus
<220> FEATURE:
<221> NAME/KEY: misc_feature
<222> LOCATION: (468)..(468)
<223> OTHER INFORMATION: n is a, c, g, or t

<400> SEQUENCE: 2

```
cggccggggg agcaaacatc gcagttgctg aacggttgcg ctcgtcttat aagcaggagt      60
aataccggtg atcagagggc gtataacggt aaggaaggta gtgagcttat tcctttgtac     120
gagacattgt gcatcgcagg tatggtgtcg atgaagacaa cgcatcatgt cctatttctg     180
ctagttgctt tggaatcaat gcgaccctac acgactgctc ttgtttcaac tattgagtca     240
agaacgagtg gagatggcgc agataacttt gatgtagtat cttgtaataa gaattgcact     300
tcaggtcaaa acgaatgccc tgaaggctgt ttttgcggct tgttgggcca gaacaaaaaa     360
ggtcattgct acaaaattat agggaacctt tctggagaac caccagttgt aaggcgttaa     420
ggagatgacc tacagctcag atgaataata aaaaaaatta agactaanaa aaaaaaaaa     480 aaaaaaaaa a                                                            491
```

<210> SEQ ID NO 3

<211> LENGTH: 554
<212> TYPE: DNA
<213> ORGANISM: Rhipicephalus sanguineus

<400> SEQUENCE: 3

```
cggccgggga ctatactgat cagttgagtg caactgggca ggtatatcc aatggctttt      60
aaatattggt tcgttttgc ggccgtcctg tatgctcgac aatggctcag cactaaatgc     120
gaagtgccac aaatgacttc gtcctccgcg ccggatcttg aagaggagga cgattacaca    180
gcatatgcac cgctgacgtg ctattttaca aattccacgc ttggtctgct ggccccccca    240
aattgctccg tgctttgcaa cagtaccaca acttggttta tgaaacttc gccaaacaat     300
gcttcgtgtt tgctgactgt ggattttctt acacaggacg ccattctaca gaaaaaccaa    360
ccgtacaact gcagtgtggg acactgtgat aatgggactt cgccgggcc cctcgacac     420
gctcagtgct ggtagaggac acggaaccag gaatgatgca cctcgcagct gctcacacta    480
tgtatgaata aaaatggagc attttgagcc gaaaaaaaaa aaaaaaaaa aaaaaaaaa     540
catgtcggcc gcct                                                     554
```

<210> SEQ ID NO 4
<211> LENGTH: 381
<212> TYPE: DNA
<213> ORGANISM: Rhipicephalus sanguineus

<400> SEQUENCE: 4

```
atggcttta aatattggtt cgttttgcg gccgtcctgt atgctcgaca atggctcagc      60
actaaatgcg aagtgccaca aatgacttcg tcctccgcgc cggatcttga agaggaggac    120
gattacacag catatgcacc gctgacgtgc tattttacaa attccacgct tggtctgctg    180
gcccccccaa attgctccgt gctttgcaac agtaccacaa cttggtttaa tgaaacttcg    240
ccaaacaatg cttcgtgttt gctgactgtg gattttctta cacaggacgc cattctacaa    300
gaaaaccaac cgtacaactg cagtgtggga cactgtgata atgggacttg cgccgggccc    360
cctcgacacg ctcagtgctg g                                             381
```

<210> SEQ ID NO 5
<211> LENGTH: 127
<212> TYPE: PRT
<213> ORGANISM: Rhipicephalus sanguineus

<400> SEQUENCE: 5

```
Met Ala Phe Lys Tyr Trp Phe Val Phe Ala Ala Val Leu Tyr Ala Arg
 1               5                  10                  15

Gln Trp Leu Ser Thr Lys Cys Glu Val Pro Gln Met Thr Ser Ser Ser
            20                  25                  30

Ala Pro Asp Leu Glu Glu Asp Asp Tyr Thr Ala Tyr Ala Pro Leu
        35                  40                  45

Thr Cys Tyr Phe Thr Asn Ser Thr Leu Gly Leu Leu Ala Pro Pro Asn
    50                  55                  60

Cys Ser Val Leu Cys Asn Ser Thr Thr Thr Trp Phe Asn Glu Thr Ser
65                  70                  75                  80

Pro Asn Asn Ala Ser Cys Leu Leu Thr Val Asp Phe Leu Thr Gln Asp
                85                  90                  95

Ala Ile Leu Gln Glu Asn Gln Pro Tyr Asn Cys Ser Val Gly His Cys
            100                 105                 110

Asp Asn Gly Thr Cys Ala Gly Pro Pro Arg His Ala Gln Cys Trp
        115                 120                 125
```

<210> SEQ ID NO 6
<211> LENGTH: 110
<212> TYPE: PRT
<213> ORGANISM: Rhipicephalus sanguineus

<400> SEQUENCE: 6

Trp Leu Ser Thr Lys Cys Glu Val Pro Gln Met Thr Ser Ser Ala
1               5                   10                  15

Pro Asp Leu Glu Glu Asp Asp Tyr Thr Ala Tyr Ala Pro Leu Thr
            20                  25                  30

Cys Tyr Phe Thr Asn Ser Thr Leu Gly Leu Leu Ala Pro Pro Asn Cys
 35              40                  45

Ser Val Leu Cys Asn Ser Thr Thr Thr Trp Phe Asn Glu Thr Ser Pro
 50                  55                  60

Asn Asn Ala Ser Cys Leu Leu Thr Val Asp Phe Leu Thr Gln Asp Ala
 65                  70                  75                  80

Ile Leu Gln Glu Asn Gln Pro Tyr Asn Cys Ser Val Gly His Cys Asp
             85                  90                  95

Asn Gly Thr Cys Ala Gly Pro Pro Arg His Ala Gln Cys Trp
            100                 105                 110

<210> SEQ ID NO 7
<211> LENGTH: 375
<212> TYPE: DNA
<213> ORGANISM: Artificial sequence
<220> FEATURE:
<223> OTHER INFORMATION: DNA coding for signal peptide of uPA

<400> SEQUENCE: 7
atgagagccc tgctggcgcg cctgcttctc tgcgtcctgg tcgtgagcga cagtaaaggc      60
gaagtgccac aaatgacttc gtcctccgcg ccggatcttg aagaggagga cgattacaca     120
gcatatgcac cgctgacgtg ctattttaca aattccacgc ttggtctgct ggccccccca     180
aattgctccg tgctttgcaa cagtaccaca acttggttta atgaaacttc gccaaacaat     240
gcttcgtgtt tgctgactgt ggattttctt acacaggacg ccattctaca gaaaaaccaa     300
ccgtacaact gcagtgtggg acactgtgat aatgggactt gcgccgggcc ccctcgacac     360
gctcagtgct ggtag                                                      375

<210> SEQ ID NO 8
<211> LENGTH: 100
<212> TYPE: DNA
<213> ORGANISM: Artificial sequence
<220> FEATURE:
<223> OTHER INFORMATION: PCR product

<400> SEQUENCE: 8
gcaggcttcg ccaccatgag agccctgctg gcgcgcctgc ttctctgcgt cctggtcgtg      60
agcgacagta aaggcggatc cccgaattcc catcaccatc                           100

<210> SEQ ID NO 9
<211> LENGTH: 358
<212> TYPE: DNA
<213> ORGANISM: Artificial sequence
<220> FEATURE:
<223> OTHER INFORMATION: PCR product

<400> SEQUENCE: 9
atccccgaat tcctgggaga ccgatgaagt gccacaaatg acttcgtcct ccgcgccgga      60

```
tcttgaagag gaggacgatt acacagcata tgcaccgctg acgtgctatt ttacaaattc    120
cacgcttggt ctgctggccc ccccaaattg ctccgtgctt tgcaacagta ccacaacttg    180
gtttaatgaa acttcgccaa acaatgcttc gtgtttgctg actgtggatt ttcttacaca    240
ggacgccatt ctacaagaaa accaaccgta caactgcagt gtgggacact gtgataatgg    300
gacttgcgcc gggccccctc gacacgctca gtgctggtga acccagctt tcttgtac     358

<210> SEQ ID NO 10
<211> LENGTH: 468
<212> TYPE: DNA
<213> ORGANISM: Artificial sequence
<220> FEATURE:
<223> OTHER INFORMATION: PCR product

<400> SEQUENCE: 10
gcaggcttcg ccaccatgag agccctgctg gcgcgcctgc ttctctgcgt cctggtcgtg     60
agcgacagta aaggcggatc cccgaattcc catcaccatc accatcacgg atccccgaat    120
tccctggaga ccgatgaagt gccacaaatg acttcgtcct ccgcgccgga tcttgaagag    180
gaggacgatt acacagcata tgcaccgctg acgtgctatt ttacaaattc cacgcttggt    240
ctgctggccc ccccaaattg ctccgtgctt tgcaacagta ccacaacttg gtttaatgaa    300
acttcgccaa acaatgcttc gtgtttgctg actgtggatt ttcttacaca ggacgccatt    360
ctacaagaaa accaaccgta caactgcagt gtgggacact gtgataatgg gacttgcgcc    420
gggccccctc gacacgctca gtgctggtga acccagctt tcttgtac              468

<210> SEQ ID NO 11
<211> LENGTH: 502
<212> TYPE: DNA
<213> ORGANISM: Artificial sequence
<220> FEATURE:
<223> OTHER INFORMATION: PCR product

<400> SEQUENCE: 11
ggggacaagt ttgtacaaaa aagcaggctt cgccaccatg agagccctgc tggcgcgcct     60
gcttctctgc gtcctggtcg tgagcgacag taaaggcgga tccccgaatt cccatcacca    120
tcaccatcac ggatccccga attccctgga gaccgatgaa gtgccacaaa tgacttcgtc    180
ctccgcgccg gatcttgaag aggaggacga ttacacagca tatgcaccgc tgacgtgcta    240
ttttacaaat tccacgcttg gtctgctggc cccccaaat tgctccgtgc tttgcaacag    300
taccacaact tggtttaatg aaacttcgcc aaacaatgct tcgtgtttgc tgactgtgga    360
ttttcttaca caggacgcca ttctacaaga aaaccaaccg tacaactgca gtgtgggaca    420
ctgtgataat gggacttgcg ccgggccccc tcgacacgct cagtgctggt gaaacccagc    480
tttcttgtac aaagtggtcc cc                                            502

<210> SEQ ID NO 12
<211> LENGTH: 35
<212> TYPE: DNA
<213> ORGANISM: Artificial sequence
<220> FEATURE:
<223> OTHER INFORMATION: PCR primer

<400> SEQUENCE: 12
gcaggcttcg ccaccatgag agccctgctg gcgcg                               35

<210> SEQ ID NO 13
```

```
<211> LENGTH: 44
<212> TYPE: DNA
<213> ORGANISM: Artificial sequence
<220> FEATURE:
<223> OTHER INFORMATION: PCR primer

<400> SEQUENCE: 13
gatggtgatg ggaattcggg gatccgcctt tactgtcgct cacg            44

<210> SEQ ID NO 14
<211> LENGTH: 42
<212> TYPE: DNA
<213> ORGANISM: Artificial sequence
<220> FEATURE:
<223> OTHER INFORMATION: PCR primer

<400> SEQUENCE: 14
atccccgaat tccctggaga ccgatgaagt gccacaaatg ac              42

<210> SEQ ID NO 15
<211> LENGTH: 40
<212> TYPE: DNA
<213> ORGANISM: Artificial sequence
<220> FEATURE:
<223> OTHER INFORMATION: PCR primer

<400> SEQUENCE: 15
gtacaagaaa gctgggtttc accagcactg agcgtgtcga                 40

<210> SEQ ID NO 16
<211> LENGTH: 46
<212> TYPE: DNA
<213> ORGANISM: Artificial sequence
<220> FEATURE:
<223> OTHER INFORMATION: PCR primer

<400> SEQUENCE: 16
attcccatca ccatcaccat cacggatccc cgaattccct ggagac          46

<210> SEQ ID NO 17
<211> LENGTH: 37
<212> TYPE: DNA
<213> ORGANISM: Artificial sequence
<220> FEATURE:
<223> OTHER INFORMATION: PCR primer

<400> SEQUENCE: 17
ggggacaagt ttgtacaaaa aagcaggctt cgccacc                    37

<210> SEQ ID NO 18
<211> LENGTH: 30
<212> TYPE: DNA
<213> ORGANISM: Artificial sequence
<220> FEATURE:
<223> OTHER INFORMATION: PCR primer

<400> SEQUENCE: 18
ggggaccact ttgtacaaga aagctgggtt                            30

<210> SEQ ID NO 19
<211> LENGTH: 18
<212> TYPE: DNA
<213> ORGANISM: Artificial sequence
<220> FEATURE:
<223> OTHER INFORMATION: PCR primer

<400> SEQUENCE: 19
```

```
tgtaaaacga cggccagt                                                    18

<210> SEQ ID NO 20
<211> LENGTH: 18
<212> TYPE: DNA
<213> ORGANISM: Artificial sequence
<220> FEATURE:
<223> OTHER INFORMATION: PCR primer

<400> SEQUENCE: 20
caggaaacag ctatgacc                                                    18

<210> SEQ ID NO 21
<211> LENGTH: 20
<212> TYPE: DNA
<213> ORGANISM: Artificial sequence
<220> FEATURE:
<223> OTHER INFORMATION: PCR primer

<400> SEQUENCE: 21
gccagcttgg cacttgatgt                                                  20

<210> SEQ ID NO 22
<211> LENGTH: 20
<212> TYPE: DNA
<213> ORGANISM: Artificial sequence
<220> FEATURE:
<223> OTHER INFORMATION: PCR primer

<400> SEQUENCE: 22
gatggaggtg gacgtgtcag                                                  20

<210> SEQ ID NO 23
<211> LENGTH: 20
<212> TYPE: DNA
<213> ORGANISM: Artificial sequence
<220> FEATURE:
<223> OTHER INFORMATION: PCR primer

<400> SEQUENCE: 23
tcttctacgg caaggtgctg                                                  20

<210> SEQ ID NO 24
<211> LENGTH: 20
<212> TYPE: DNA
<213> ORGANISM: Artificial sequence
<220> FEATURE:
<223> OTHER INFORMATION: PCR primer

<400> SEQUENCE: 24
aagcaagtaa aacctctaca                                                  20

<210> SEQ ID NO 25
<211> LENGTH: 450
<212> TYPE: DNA
<213> ORGANISM: Artificial sequence
<220> FEATURE:
<223> OTHER INFORMATION: cDNA sequence, containing from 5' end, the
      signal peptide sequence of uPA, five amino acid linker (GSPNS), a
      6 histidine tag sequence, a second linker (GSPNS) and caspase 8
      cleavage site(LETD), followed by cDNA encoding amino acids
      18-127 of evasin-4.

<400> SEQUENCE: 25
atgagagccc tgctggcgcg cctgcttctc tgcgtcctgg tcgtgagcga cagtaaaggc      60
```

-continued

```
ggatccccga attcccatca ccatcaccat cacggatccc cgaattccct ggagaccgat      120
tggctcagca ctaaatgcga agtgccacaa atgacttcgt cctccgcgcc ggatcttgaa      180
gaggaggacg attacacagc atatgcaccg ctgacgtgct attttacaaa ttccacgctt      240
ggtctgctgg ccccccaaa ttgctccgtg ctttgcaaca gtaccacaac ttggtttaat       300
gaaacttcgc caaacaatgc ttcgtgtttg ctgactgtgg attttcttac acaggacgcc      360
attctacaag aaaaccaacc gtacaactgc agtgtgggac actgtgataa tgggacttgc      420
gccgggcccc ctcgacacgc tcagtgctgg                                      450

<210> SEQ ID NO 26
<211> LENGTH: 46
<212> TYPE: DNA
<213> ORGANISM: Artificial sequence
<220> FEATURE:
<223> OTHER INFORMATION: PCR primer

<400> SEQUENCE: 26
cctggagacc gattggctca gcactaaatg cgaagtgcca caaatg                    46

<210> SEQ ID NO 27
<211> LENGTH: 46
<212> TYPE: DNA
<213> ORGANISM: Artificial sequence
<220> FEATURE:
<223> OTHER INFORMATION: PCR primer

<400> SEQUENCE: 27
catttgtggc acttcgcatt tagtgctgag ccaatcggtc tccagg                    46
```